(12) United States Patent
Edelman et al.

(10) Patent No.: US 11,197,618 B2
(45) Date of Patent: *Dec. 14, 2021

(54) CARDIOVASCULAR ASSIST SYSTEM THAT QUANTIFIES HEART FUNCTION AND FACILITATES HEART RECOVERY

(71) Applicants: Abiomed, Inc., Danvers, MA (US); Massachusetts Institute of Technology, Cambridge, MA (US)

(72) Inventors: Elazer Edelman, Cambridge, MA (US); Brian Chang, Cambridge, MA (US); Noam Joesphy, Danvers, MA (US); Sonya Sanat Bhavsar, Danvers, MA (US)

(73) Assignees: ABIOMED, INC., Danvers, MA (US); Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/455,835

(22) Filed: Jun. 28, 2019

(65) Prior Publication Data

US 2020/0060559 A1 Feb. 27, 2020

Related U.S. Application Data

(63) Continuation of application No. 15/709,080, filed on Sep. 19, 2017, now Pat. No. 10,376,162.

(Continued)

(51) Int. Cl.
*A61B 5/021* (2006.01)
*A61B 5/02* (2006.01)
(Continued)

(52) U.S. Cl.
CPC ........ *A61B 5/02141* (2013.01); *A61B 5/0205* (2013.01); *A61B 5/029* (2013.01);
(Continued)

(58) Field of Classification Search
CPC .. A61M 1/122; A61M 1/1031; A61M 1/1096; A61M 1/12; A61M 2205/3334;
(Continued)

(56) References Cited

U.S. PATENT DOCUMENTS 3,677,092 A 7/1972 Guarino
4,468,219 A 8/1984 George et al.
(Continued)

FOREIGN PATENT DOCUMENTS

JP 2000512191 A 9/2000
JP 2003508161 A 3/2003
(Continued)

OTHER PUBLICATIONS

International Search Report and Written Opinion PCT/US2017/052259, dated Dec. 19, 2017 (13 pages).
(Continued)

*Primary Examiner* — Jon Eric C Morales
(74) *Attorney, Agent, or Firm* — Botos Churchill IP Law LLP

(57) ABSTRACT

The systems, devices, and methods presented herein use a heart pump to obtain measurements of cardiovascular function. The heart pumps described herein can operate in parallel with and unload the heart. The system can quantify the functioning of the native heart by measuring certain parameters/signals such as pressure or motor current, then calculate and display one or more metrics of cardiovascular function. These metrics, such as left ventricular end diastolic pressure (LVEDP), left ventricular pressure, and contractility, provide valuable information to a user regarding a patient's state of heart function and recovery.

19 Claims, 23 Drawing Sheets

Related U.S. Application Data

(60) Provisional application No. 62/396,628, filed on Sep. 19, 2016.

(51) Int. Cl.
| | | |
|---|---|---|
| *A61B 5/0205* | (2006.01) | |
| *A61B 5/0215* | (2006.01) | |
| *A61B 5/029* | (2006.01) | |
| *A61B 5/00* | (2006.01) | |
| *A61B 5/352* | (2021.01) | |
| *A61M 60/50* | (2021.01) | |
| *A61M 60/135* | (2021.01) | |
| *A61B 5/024* | (2006.01) | |
| *A61B 5/026* | (2006.01) | |

(52) U.S. Cl.
CPC ........ *A61B 5/0215* (2013.01); *A61B 5/02028* (2013.01); *A61B 5/02158* (2013.01); *A61B 5/352* (2021.01); *A61B 5/4848* (2013.01); *A61B 5/7275* (2013.01); *A61M 60/135* (2021.01); *A61M 60/50* (2021.01); *A61B 5/026* (2013.01); *A61B 5/02405* (2013.01); *A61B 2505/09* (2013.01)

(58) Field of Classification Search
CPC .............. A61B 5/02028; A61B 5/0205; A61B 5/02141; A61B 5/0215; A61B 5/02405; A61B 5/026; A61B 5/029; A61B 5/0456; A61B 2017/00243; A61B 2017/00252
See application file for complete search history.

(56) References Cited

U.S. PATENT DOCUMENTS

| | | |
|---|---|---|
| 4,598,579 A | 7/1986 | Cummings et al. |
| 5,437,284 A | 8/1995 | Trimble |
| 5,964,694 A | 10/1999 | Siess et al. |
| 6,129,660 A | 10/2000 | Nakazeki et al. |
| 6,159,160 A | 12/2000 | Hsei et al. |
| 6,176,822 B1 | 1/2001 | Nix et al. |
| 6,234,759 B1 | 5/2001 | Hennel et al. |
| 6,623,420 B2 | 9/2003 | Reich et al. |
| 7,010,954 B2 | 3/2006 | Siess et al. |
| 7,022,100 B1 | 4/2006 | Aboul-Hosn et al. |
| 10,376,162 B2 * | 8/2019 | Edelman ............ A61B 5/02141 |
| 2003/0139643 A1 | 7/2003 | Smith et al. |
| 2004/0106874 A1 | 6/2004 | Eigler et al. |
| 2015/0283027 A1 | 10/2015 | Lampe et al. |
| 2016/0367740 A1 | 12/2016 | Aboul-Hosn et al. |
| 2017/0136164 A1 | 5/2017 | Yeatts |

FOREIGN PATENT DOCUMENTS

| | | |
|---|---|---|
| WO | 9749439 A1 | 12/1997 |
| WO | 9819624 A2 | 5/1998 |
| WO | 9843688 A1 | 10/1998 |
| WO | 0117581 A2 | 3/2001 |
| WO | 2014062911 A2 | 4/2014 |
| WO | 2018036927 A1 | 3/2018 |
| WO | 2018073150 A1 | 4/2018 |
| WO | 2018146045 A1 | 8/2018 |

OTHER PUBLICATIONS

International Search Report PCT/US2017/052259, dated Dec. 19, 2017 (4 pages).

Stolinski, et al., "The heart-pump interaction: effects of a microaxial blood pump", International Journal of Artificial Organs, vol. 25, No. 11, pp. 1082-1088 (2002).

Office Action for Chinese Application No. 201780071777.9 dated Apr. 6, 2021 (17 pages).

Notice of Reasons for Rejection received in JP Patent Application No. 2019-515324, dated Sep. 8, 2021.

* cited by examiner

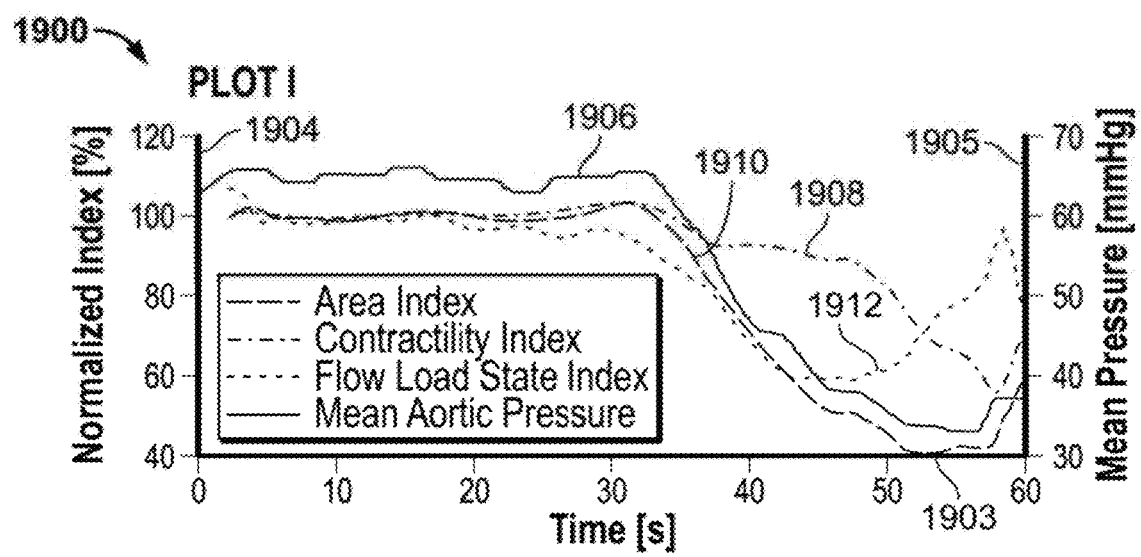
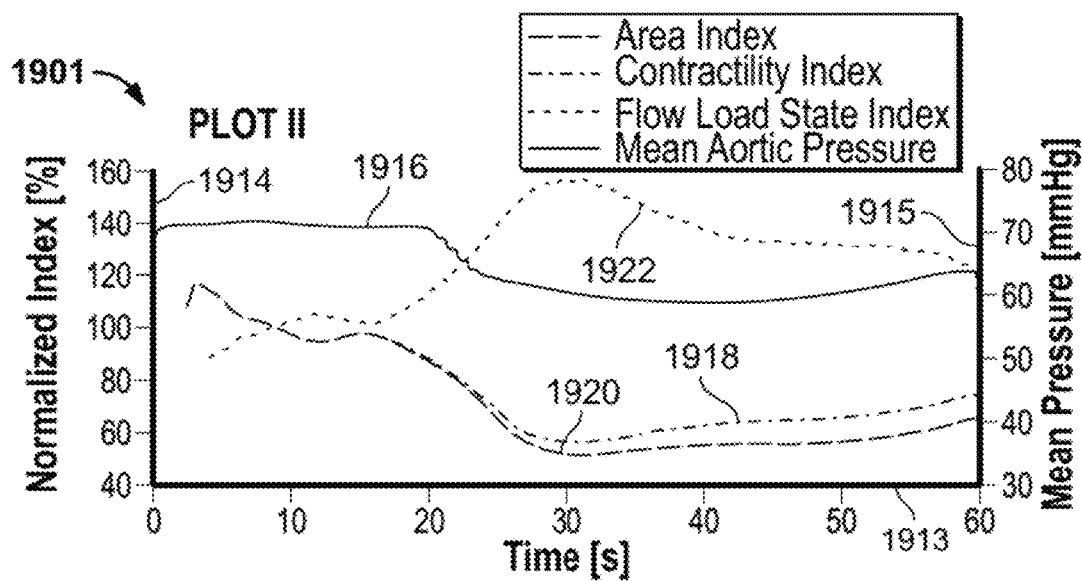
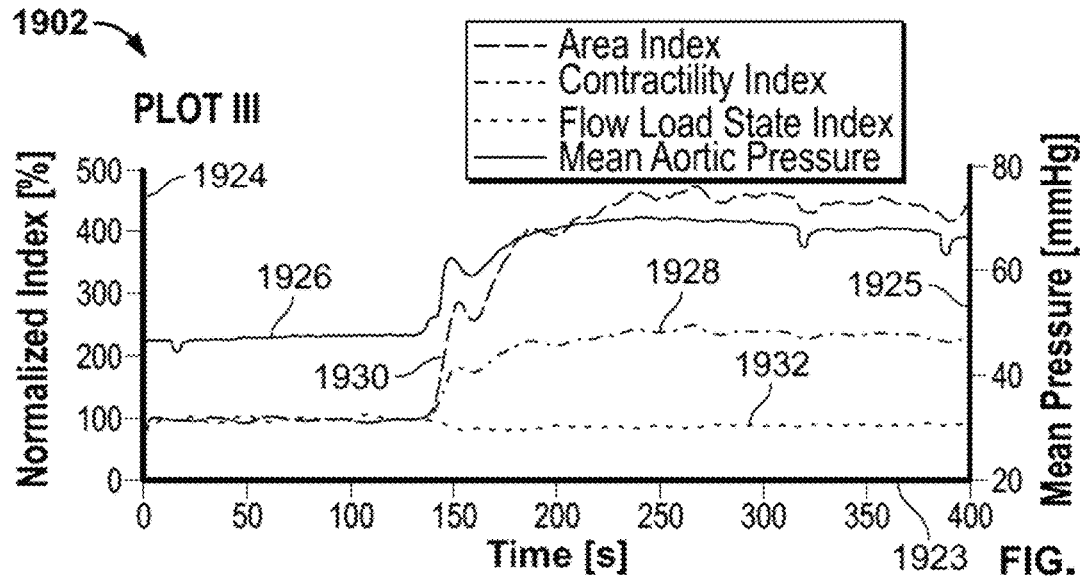
FIG. 19

CARDIOVASCULAR ASSIST SYSTEM THAT QUANTIFIES HEART FUNCTION AND FACILITATES HEART RECOVERY

CROSS-REFERENCE TO RELATED APPLICATIONS

This application is a continuation of U.S. application Ser. No. 15/709,080, filed Sep. 19, 2017 (now U.S. Pat. No. 10,376,162), which claims priority to U.S. Provisional Application No. 62/396,628, filed Sep. 19, 2016. The specifications of each of the foregoing applications are incorporated herein by reference in their entirety.

BACKGROUND

Cardiovascular (CV) diseases are a leading cause of morbidity, mortality, and burden on healthcare around the world, with about 7 million cases of heart failure and many more cases of myocardial infarction in the United States alone. Acute and chronic CV conditions reduce quality of life and life expectancy. A variety of treatment modalities have been developed for CV disease, ranging from pharmaceuticals to mechanical devices and finally transplantation. Temporary cardiac support devices, such as ventricular assist devices, provide hemodynamic support, and facilitate heart recovery.

There are many types of temporary cardiac assist devices with varying degrees of support and invasiveness, from intra-aortic balloon pumps (IABP) to extracorporeal membrane oxygenation (ECMO) devices to left ventricular assist devices (LVAD) implanted surgically. These devices commonly reside outside the ventricle or bypass the ventricle, and do not work in parallel with or directly support heart function. They also do not provide clinicians with quantifiable metrics that can guide the level of cardiac support that is required for a particular patient. Some ventricular assist devices are percutaneously inserted into the heart and can run in parallel with the native heart to supplement cardiac output, such as the IMPELLA® family of devices (Abiomed, Inc., Danvers Mass.).

The amount of support (e.g., volumetric flow rate of blood delivered by the pumping device) and/or the duration of support each patient needs can vary. It has been suggested that variations in the motor current required to maintain a rotor speed can be utilized to understand placement of the pump or pump function, but these proposals have fallen short of usefully processing the motor current data to measure cardiac function. For example, U.S. Pat. No. 6,176,822 describes measuring motor current to aid in proper positioning of the pump, and U.S. Pat. No. 7,022,100 mentions calculating blood pressure based on the relationship between the torque and motor current of a motor used to drive the rotor. However, the motor current alone provides only limited insights into a patient's overall cardiac function, and existing measures such as aortic pressure do not correlate to a patient's overall cardiac function. Accordingly, there is a need to more directly and quantitatively estimate metrics of cardiac function to aid clinicians in determining how much support a device should deliver or when to terminate use of a cardiac assist device.

SUMMARY

The systems, devices, and methods described herein enable a support device residing within an organ to assess that organ's function. In particular, the systems, devices, and methods enable cardiac assist devices, such as percutaneous ventricular assist devices, to be used to assess the function of the heart based on a measurement of device performance and measurement of one or more hemodynamic parameters. Assessing the function of the heart using a cardiac assist device can allow the degree of/level of support provided by the assist device (e.g., flow rate of blood pumped by a pumping device) to be tailored to a particular patient's needs. For example, changes in device performance (or absolute performance of the device) can be detected and the detected performance used to determine whether and the extent to which a patient's heart is deteriorating or improving. Based on the detected performance, the degree of support is adjusted. For example, the degree of support can be increased when a patient's heart function is deteriorating, or the degree of support can be decreased when a patient's heart function is recovering and returning to a baseline of normal heart function. This allows the clinician to respond to changes in heart function to promote heart recovery, which can allow the patient to be gradually weaned off of the therapy. Furthermore, assessment of the heart function for greater understanding of cardiac function can indicate when it is appropriate to terminate use of the cardiac assist device. Although some embodiments presented herein are directed to cardiovascular assist devices implanted across the aortic valve and residing partially in the left ventricle, the concepts can be applied to devices in other regions of the heart, the cardiovascular system, or the body.

Moreover, the cardiac assist devices herein can continuously or nearly continuously monitor and assess cardiac function while the device is in the patient. This can be advantageous over methods that only estimate cardiac function at specific intervals of time. For example, continuous monitoring may allow real time detection of cardiac deterioration, which is more rapid than prior art methods. The cardiac devices can be inserted without destruction of injury of organs using minimally invasive procedures. Additionally, if the cardiac assist device is already in the patient, the cardiac function can be measured without having to introduce an additional catheter into a patient.

The systems, devices, and methods presented herein determine heart function parameters indicative of native heart function from measurements of intravascular pressure and pump parameters (a "parameter" can represent a signal and/or operating state of the cardiovascular system and/or the heart pump). Cardiac function can be quantified in several different ways using the devices and techniques presented herein, including one or more of left ventricular end diastolic pressure (LVEDP), contractility, stroke volume, ejection fraction, chamber pressure, stroke work, cardiac output, cardiac power output, preload state, afterload state, heart rate, heart recovery, flow load state, variable volume load state, and/or cardiac cycle flow state. In some applications, such heart parameters are determined based in part on hysteresis between pressure measurements (e.g., differential pressure between aortic pressure and left ventricular pressure, or the aortic pressure, or other pressure measured in the vasculature or within a device inserted within the vasculature) and motor current measurements that allow the detection of the phase of the cardiac cycle corresponding to a given pair of pressure and current measurements. From these measurements a user can determine important information about heart function, and in some cases information about the cardiac assist device performance, including the occurrence of suction events.

In one aspect, a heart pump system includes a catheter, a motor, a rotor operatively coupled to the motor, and a pump housing at least partially surrounding the rotor so that actuating the motor drives the rotor and pumps blood through the pump housing. The heart pump system also includes a sensor which detects a hemodynamic parameter over time, and a controller. The controller detects a motor parameter over time, receives an input from the sensor of the detected hemodynamic parameter over time, and determines a relationship between the detected hemodynamic parameter and the motor parameter, such as the relationship between the hemodynamic parameter measured over time and the motor parameter measured over time. For example, the controller may store the detected motor parameter and hemodynamic parameters in a memory and may associate the motor parameter and hemodynamic parameter data so that they are matched in time. The controller characterizes the relationship between the detected hemodynamic parameter and the motor parameter using a polynomial best fit algorithm, and stores the characterized relationship in a memory. For example, the controller may characterize the relationship by fitting all or a portion of the data (e.g., a portion of the hemodynamic parameter data, such as pressure measurements, and a portion of the motor parameter data, such as motor current measurements) to an appropriate equation, such as an elliptical fit, a polynomial equation, or Euler's equation.

In some implementations, the motor parameter is current delivered to the motor, power delivered to the motor, or motor speed. In some implementations, the controller determines at least one cardiovascular metric by extracting an inflection point, a local slope change, or a curvature change from the characterized relationship between the detected hemodynamic parameter and the motor parameter. In some implementations, the at least one cardiovascular metric is at least one of contractility, stroke volume, ejection fraction, chamber pressure, stroke work, cardiac output, cardiac power output, left ventricular pressure, preload state, afterload state, heart rate, heart recovery, flow load state, variable volume load state, cardiac cycle volume load state, or cardiac cycle flow state. In some implementations, the at least one cardiovascular metric is the left ventricular end diastolic pressure (LVEDP).

In some implementations, the hemodynamic parameter is aortic pressure and the motor parameter is current, and characterizing the relationship includes fitting an equation to at least a portion of data representing the measured current and a pressure head calculated from the measured current and aortic pressure. In some implementations, the controller determines an LVEDP point from the equation fit to at least a portion of the current and pressure head data, and accesses a look-up table to determine an actual LVEDP value from the LVEDP point in the pressure head data. In some implementations, determining an LVEDP point includes identifying an inflection point, a local slope change, or a curvature change in the equation fit to at least a portion of the current and pressure head data.

In some implementations, the controller determines a cardiac cycle phase from the relationship between the detected hemodynamic parameter and the motor parameter. In some implementations, the controller describes a hysteresis curve based on the relationship between the detected hemodynamic parameter and the motor parameter, and selects a sample time on the hysteresis curve corresponding to the cardiac cycle phase.

In some implementations, determining the cardiac cycle phase includes detecting that the cardiac cycle phase is in diastolic relaxation when the sample time corresponds to a segment of the hysteresis curve corresponding to an increasing pressure head, detecting that the cardiac cycle phase is in diastolic filling when the sample time corresponds to a segment of the hysteresis curve corresponding to a decreasing pressure head following diastolic relaxation to appoint distinguished by a rapid change in slope or curvature, or identification of the inflection point, or detecting that the cardiac cycle phase is in systole when the sample time corresponds to a segment of the hysteresis curve having a decreasing pressure head from the inflection point to a minimum pressure head.

In some implementations, the motor parameter and hemodynamic parameter are detected over a portion of a cardiac cycle. In other implementations, the motor parameter and hemodynamic parameter are detected over one or more cardiac cycles. In some implementations, the motor maintains a substantially constant speed of the rotor during actuation of the rotor. In some implementations, the controller stores the at least one cardiovascular metric in a memory with a previously determined at least one cardiovascular metric. In some implementations, the heart pump system also includes an integrated motor positioned near the distal end of the catheter proximate the heart pump.

In another aspect, a heart pump system includes a catheter, a motor, a rotor operatively coupled to the motor, and a pump housing at least partially surrounding the rotor so that actuating the motor drives the rotor and pumps blood through the pump housing. The heart pump system also includes a pressure sensor which detects an aortic pressure over time, and a controller. The controller detects a motor parameter over time, receives the aortic pressure over time from the sensor, stores a relationship between the motor parameter and the aortic pressure in the memory, determines a time period in which an inflection point indicative of LVEDP can be found, and identifies the inflection point in the aortic pressure based on the determined time period.

In some implementations, determining a time period in which an inflection point indicative of the LVEDP can be found includes identifying a time period in which the received motor parameter changes. In some implementations, the controller also determines the LVEDP from a dynamic curve look-up table stored in the memory based on the inflection point in the aortic pressure. In some implementations, the controller receives an ECG signal, and determining a time period in which an inflection point indicative of LVEDP can be found includes identifying a time period in which the ECG signal indicates an end cycle of diastole.

In some implementations, the motor parameter is one of motor current, change in motor current, variability of motor current, and a net integrated area of motor current and pressure. In some implementations, the controller also determines a cardiac cycle phase from the relationship between the motor parameter and the aortic pressure, and the cardiac cycle phase is determined using one or more of ECG data, a hemodynamic parameter, the motor parameter and a motor speed, and/or a slope of the aortic pressure. In some implementations, the motor is configured to maintain a substantially constant rotor speed during actuation of the rotor. In some implementations, the heart pump further comprises an integrated motor sized and configured for insertion into a patient's vasculature.

In another aspect, a heart pump system includes a heart pump and an electronic controller. The heart pump includes a motor, a rotor operatively coupled to the motor, and a sensor of hemodynamic parameters. The controller is configured to measure a motor parameter, for example current delivered to the motor, power delivered to the motor, or motor speed, and to measure the hemodynamic parameter over time using the sensor. The controller is configured to determine and describe a hysteresis curve based on inputs representative of the motor parameter and inputs representative of the hemodynamic parameter over time, determined according to a best fit algorithm or other suitable processing algorithm, and to scale the fitted hysteresis curve based on a measured patient cardiac parameter, for example aortic pressure, to determine a left ventricular pressure.

In some implementations, the controller is configured to determine at least one cardiovascular metric by extracting an inflection point value from a scaled hysteresis curve. In some adaptations, the at least one cardiovascular metric is the left ventricular end diastolic pressure. In some implementations, determining or characterizing the hysteresis curve includes selecting a polynomial expression to fit the hysteresis curve and using the controller to process data representative of motor parameter and hemodynamic parameter (e.g., from sensor measurements) to calculate the curve. For example, data indicative of motor parameters and measured hemodynamic parameter may be stored in the controller as arrays of data in tables within a database in a memory or in a server, and the controller may access such data tables to obtain such data to calculate the hysteresis curve. The stored data can be accessed by the controller or by a user at a later time.

In some implementations, the hemodynamic parameter is pressure head. In some implementations, the at least one cardiovascular metric is at least one of contractility, stroke volume, ejection fraction, chamber pressure, stroke work, cardiac output, cardiac power output, left ventricular end diastolic pressure, preload state, afterload state, heart rate, heart recovery, flow load state, variable volume load state, cardiac cycle volume load state, and/or cardiac cycle flow state. In some implementations, the motor maintains a constant speed of the rotor during the measurement of the motor parameter.

In some implementations, the controller is further configured to determine, from the hysteresis curve, a heart phase. In some implementations, the heart phase is determined using one or more of ECG data, pressure measured at the pressure sensor, the motor parameter and motor speed, the aortic pressure slope, and a respiratory variation. In some implementations, determining the heart phase includes selecting, based on the measurement of the motor parameter and a pressure head at a sample time, a segment of the hysteresis curve to which the sample time corresponds, the segment corresponding to one of relaxation, contraction, ejection, and filling. In some implementations, determining the heart phase further includes detecting that the heart phase is diastole when the sample time corresponds to a segment of the hysteresis curve having a high pressure, and detecting that the heart phase is systole when the sample time corresponds to a segment of the hysteresis curve having a low pressure.

In another aspect, a heart pump system includes a motor, a rotor operatively coupled to the motor, a pressure sensor, and a controller. The controller is configured to measure a motor parameter, measure pressure head over time, using the pressure sensor, describe a hysteresis curve based on hysteresis between the motor parameter and the pressure head over time according to a best fit algorithm, scale the fitted hysteresis curve based on a measured aortic pressure to determine a left ventricular pressure, determine at least one cardiovascular metric by extracting an inflection point from the scaled hysteresis curve, and display the at least one cardiovascular metric on a display screen of the controller.

In some implementations, the at least one cardiovascular metric is the left ventricular end diastolic pressure. In some implementations, describing the hysteresis curve includes choosing a polynomial expression to fit the hysteresis curve. In some implementations, the at least one cardiovascular metric is at least one of contractility, stroke volume, ejection fraction, chamber pressure, stroke work, cardiac output, cardiac power output, left ventricular end diastolic pressure, preload state, afterload state, heart rate, heart recovery, flow load state, variable volume load state, cardiac cycle volume load state, and/or cardiac cycle flow state. In some implementations, the motor parameter is motor current, change in motor current, variability of motor current, or the net integrated area of motor current and pressure. In some implementations, the motor maintains a constant rotor speed during the measurement of the motor parameter.

In some implementations, the controller is further configured to determine a heart phase from the hysteresis curve. In some implementations, the heart phase is determined using one or more of ECG data, pressure measured at the pressure sensor, the motor parameter and motor speed, the aortic pressure slope, and a respiratory variation. In some implementations, determining the heart phase includes accessing the hysteresis curve, selecting, based on the measurement of the motor parameter and the pressure head and a sample time, a segment of the curve to which the sample time corresponds, and determining, based on the segment, a corresponding heart phase of relaxation, contraction, ejection, or filling.

In some implementations, the motor has a diameter of less than about 21 French. In some implementations, the at least one heart metric is at least one of contractility, stroke volume, ejection fraction, chamber pressure, stroke work, cardiac output, cardiac power output, left ventricular end diastolic pressure, preload state, afterload state, heart rate, heart recovery, flow load state, variable volume load state, cardiac cycle volume load state, and/or cardiac cycle flow state. In some implementations, the controller is configured to automatically adjust a level of support provided by the heart pump when the at least one heart metric indicates changes in a patient's heart state, wherein the patient's heart state is defined by at least one of changes in contractility, changes in volume load, changes in preload, changes in afterload, changes in heart rate, and changes in pulse pressure. In some implementations, the controller is configured to automate a level or method of support provided by the heart pump to augment and improve native heart functions, wherein automating the level or method of support comprises at least one of changing a volume flow of blood delivered by the heart pump, changing a frequency and/or amplitude of automated blood flow pulsation, and changing a rotational speed of the rotor. In some implementations, the motor maintains a constant motor speed during the measurement of the motor parameter.

In some implementations, determining the heart phase includes accessing a plot of the pressure as a function of the motor parameter wherein the plot forms a hysteresis loop, and using the measurement of the motor parameter and the pressure at the sample time to identify a segment of the hysteresis loop to which a sample time corresponds, wherein each segment corresponds to a heart phase. In some implementations, the heart phase is determined using ECG data. In some implementations, the heart phase is determined using the pressure measured at the pressure sensor. In some implementations, determining the heart phase also includes detecting that the heart phase is diastole if the sample time corresponds to a segment of the hysteresis loop having high pressure, and detecting that the heart phase is systole if the sample time corresponds to a segment of the hysteresis loop having low pressure.

In some implementations, the controller is configured to generate a plot of the pressure and motor parameter measurements, wherein the motor parameter is a first coordinate of the plot and the pressure is a second coordinate of the plot, or to monitor the relationship of a motor parameter and pressure system. In some implementations, the blood pump is percutaneous. In some implementations, the motor is implantable. In some implementations, the heart pump system is configured such that the pressure sensor is positioned within the aorta when the rotor is placed in the aorta. In some implementations, the heart pump system is an intravascular heart pump system.

In another aspect, a heart pump system includes a heart pump and a controller. The heart pump includes a motor, a rotor operatively coupled to the motor, and a sensor for a hemodynamic parameter, for example a pressure sensor. The controller is configured to measure a motor parameter and measure hemodynamic parameter by the sensor, determine a heart phase, determine at least one heart metric indicative of cardiac function and display the at least one heart metric on a display screen of the controller. For example, the controller may be configured to measure the motor parameter of current delivered to the motor or power delivered to the motor, measure the pressure at a pressure sensor, determine a heart phase, determine at least one heart metric indicative of cardiac function and display the at least one heart metric on a display screen of the controller. The heart metric indicative of cardiac function may be determined using a predetermined pressure-motor curve, and the determination of the at least one heart metric may be based on hysteresis between the motor parameter and the pressure.

In some implementations, the measured pressure is one of aortic pressure, or a difference in pressure between aortic pressure and left ventricular pressure. In some implementations, the at least one heart metric is at least one of contractility, stroke volume, ejection fraction, chamber pressure, stroke work, cardiac output, cardiac power output, left ventricular end diastolic pressure, preload state, afterload state, heart rate, heart recovery, flow load state, variable volume load state, cardiac cycle volume load state, and/or cardiac cycle flow state. In some implementations, the controller is configured to automatically adjust a level of support provided by the heart pump when the at least one heart metric indicates changes in a patient's heart state, wherein the patient's heart state is defined by at least one of changes in contractility, changes in volume load, changes in preload, changes in afterload, changes in heart rate, and changes in pulse pressure. In some implementations, the controller is configured to automate a level or method of support provided by the heart pump to augment and improve native heart functions, wherein automating the level or method of support comprises at least one of changing a volume flow of blood delivered by the heart pump, changing a frequency and/or amplitude of automated blood flow pulsation, and changing a rotational speed of the rotor. In some implementations, the motor maintains a constant motor speed during the measurement of the motor parameter.

In some implementations, determining the heart phase includes accessing a plot of the pressure as a function of the motor parameter wherein the plot forms a hysteresis loop, and using the measurement of the motor parameter and the pressure at the sample time to determine a segment of the hysteresis loop to which a sample time corresponds, wherein each segment corresponds to a heart phase. In some implementations, the heart phase is determined using ECG data. In some implementations, the heart phase is determined using the pressure measured at the pressure sensor. In some implementations, determining the heart phase also includes detecting that the heart phase is diastole if the sample time corresponds to a segment of the hysteresis loop having high pressure, and detecting that the heart phase is systole if the sample time corresponds to a segment of the hysteresis loop having low pressure.

In some implementations, the controller is configured to generate a plot of the pressure and motor parameter measurements, wherein the motor parameter is a first coordinate of the plot and the pressure is a second coordinate of the plot, or to monitor the relationship of a motor parameter and pressure system. In some implementations, the blood pump is percutaneous. In some implementations, the motor is implantable. In some implementations, the heart pump system is configured such that the pressure sensor is positioned within the aorta when the rotor is placed in the aorta. In some implementations, the motor parameter is one of motor current, change in motor current, variability of motor current, and the net integrated area of motor current and pressure. In some implementations, the heart pump system is an intravascular heart pump system.

In another aspect, a heart pump system includes a heart pump and a controller. The heart pump includes a motor, a rotor operatively coupled to the motor, and a pressure sensor. The controller is configured to measure a motor parameter where the motor parameter is current delivered to the motor or power delivered to the motor, measure the pressure at the pressure sensor, determine a heart phase, determine at least one heart metric indicative of cardiac function, determine at least one recommendation of a change for operating a heart pump based on the at least one heart metric, and display the at least one recommendation on a display screen of the controller. The heart metric indicative of cardiac function is determined using a predetermined pressure-motor curve, and the determination of the at least one heart metric is based on hysteresis between the motor parameter and the pressure.

In some implementations, at least one recommendation includes changing a rotational speed of the rotor, changing power delivered to the motor, and/or removing the heart pump from a patient. In some implementations, the at least one heart metric is at least one of contractility, stroke volume, ejection fraction, chamber distention, chamber hypertrophy, chamber pressure, stroke work, cardiac output, cardiac power output, left ventricular end diastolic pressure, preload state, afterload state, heart rate, and heart recovery. In some implementations, the controller is configured to automatically adjust a level of support provided by the heart pump when the at least one heart metric indicates changes in a patient's heart state, wherein the patient's heart state is defined by at least one of changes in contractility, changes in volume load, changes in preload, changes in afterload, changes in heart rate, and changes in pulse pressure. In some implementations, the controller is configured to automate a level or method of support provided by the heart pump to augment and improve native heart functions, wherein automating the level or method of support comprises at least one of changing a volume flow of blood delivered by the heart pump, changing a frequency and/or amplitude of automated blood flow pulsation, and changing a rotational speed of the rotor. In some implementations, the motor maintains a constant motor speed during the measurement of the motor parameter.

In some implementations, determining the heart phase includes accessing a plot of the pressure as a function of the motor parameter wherein the plot forms a hysteresis loop, and using the measurement of the motor parameter and the pressure at the sample time to identify a segment of the hysteresis loop to which a sample time corresponds, wherein each segment corresponds to a heart phase. In some implementations, the heart phase is determined using ECG data. In some implementations, the heart phase is determined using the pressure measured at the pressure sensor. In some implementations, determining the heart phase also includes detecting that the heart phase is diastole if the sample time corresponds to a segment of the hysteresis loop having high pressure, and detecting that the heart phase is systole if the sample time corresponds to a segment of the hysteresis loop having low pressure.

In some implementations, the controller is configured to generate a plot of the pressure and motor parameter measurements, wherein the motor parameter is a first coordinate of the plot and the pressure is a second coordinate of the plot, or to monitor the relationship of a motor parameter and pressure system. In some implementations, the blood pump is percutaneous. In some implementations, the motor is implantable. In some implementations, the heart pump system is configured such that the pressure sensor is positioned within the aorta when the rotor is placed in the aorta. In some implementations, the motor parameter is one of motor current, change in motor current, variability of motor current, and the net integrated area of motor current and pressure. In some implementations, the heart pump system is an intravascular heart pump system.

In another aspect, a heart pump system includes a heart pump and a controller. The heart pump includes a rotor, a motor coupled to the rotor, a blood inlet, and a pressure sensor. The controller is in communication with the motor and the pressure sensor. The controller is configured to measure a motor parameter at a sample time, measure pressure at the pressure sensor at the sample time, and determine whether the blood inlet is occluded based on the measurement of the motor parameter and the pressure at the sample time, wherein occlusion of the blood inlet is determined using hysteresis in the measurement of the motor parameter and the pressure at the pressure sensor. In some implementations, the controller is configured to display a warning parameter in response to determining that the blood inlet is occluded.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 19 shows a series of plots of mock loop data with varied contractility under a constant load;

DETAILED DESCRIPTION

Figure 1:
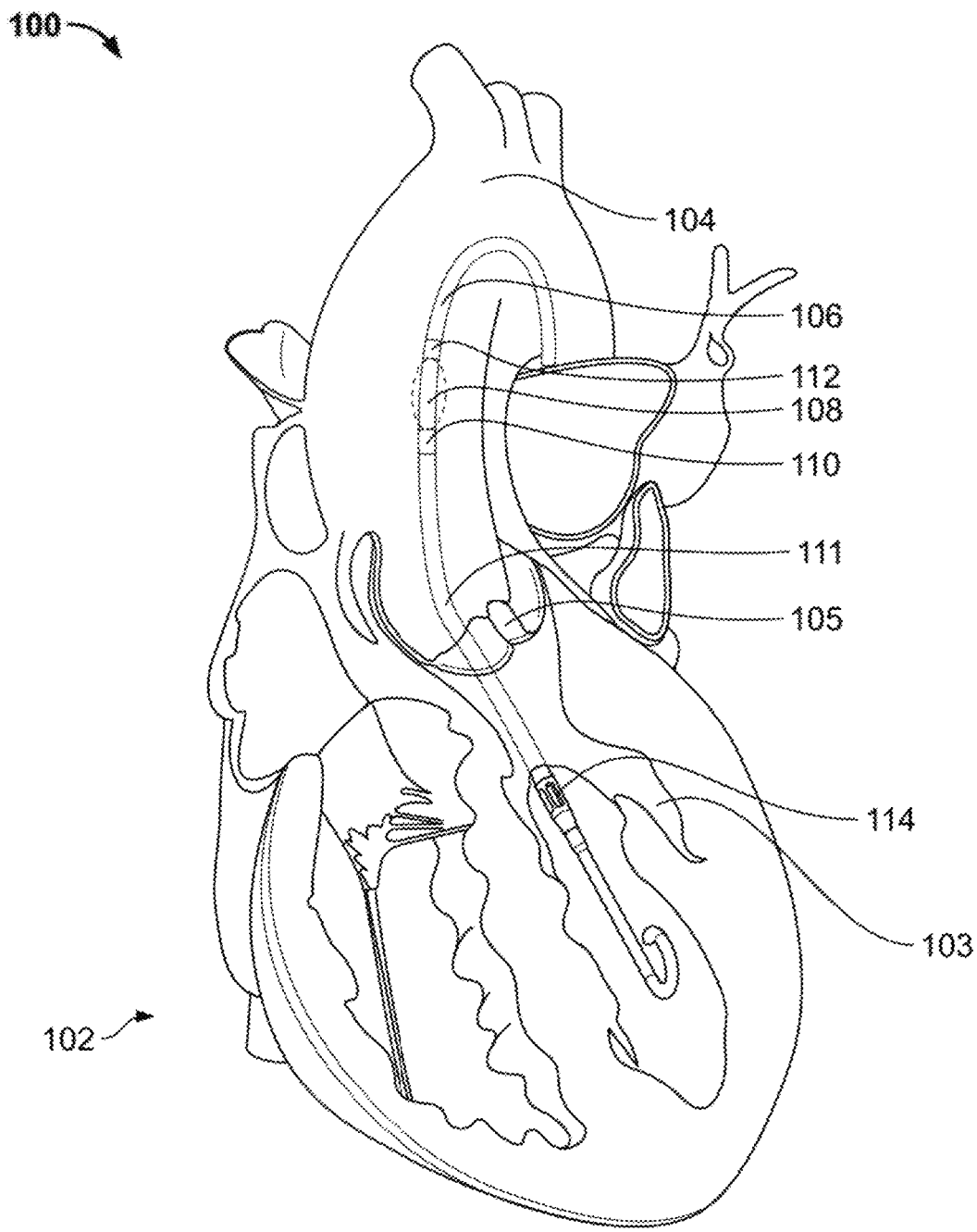
FIG. 1 shows a prior art catheter-based intravascular heart pump system located in a heart.

To provide an overall understanding of the systems, method, and devices describe herein, certain illustrative embodiments will be described. Although the embodiments and features described herein are specifically described for use in connection with a percutaneous heart pump system, it will be understood that all the components and other features outlined below may be combined with one another in any suitable manner and may be adapted and applied to other types of cardiac therapy and cardiac assist devices, including cardiac assist devices implanted using a surgical incision, and the like.

The systems, devices, and methods described herein enable a support device residing completely or partially within an organ to assess that organ's function. In particular, the systems, devices, and methods enable cardiac assist devices, such as percutaneous ventricular assist devices, to be used to assess the function of the heart. For example, a cardiac state can be measured or monitored by tracking the electro-mechanical controller values of a ventricular assist device positioned in the heart of a patient. Because the device maintains a constant rotor speed by varying the motor current to respond to changes in the pressure in the chambers of the heart, a continuous measurement of a motor parameter and a pressure, for example the motor current and the aortic pressure, provides continuous, real-time, and precise determination of cardiac function, for example a left ventricular pressure. Assessing the function of the heart using a cardiac assist device can alert health professionals of changes in cardiac function and allow the degree of/level of support provided by the assist device (i.e., flow rate of blood pumped by the device) to be tailored to a particular patient's needs. For example, the degree of support can be increased when a patient's heart function is deteriorating, or the degree of support can be decreased when a patient's heart function is recovering and returning to a baseline of normal heart function. This can allow the device to dynamically respond to changes in heart function to promote heart recovery and can allow the patient to be gradually weaned off of the therapy. Furthermore, assessment of the heart function can indicate when it is appropriate to terminate use of the cardiac assist device. Although some embodiments presented herein are directed to cardiac assist devices implanted across the aortic valve and residing partially in the left ventricle, the concepts can be applied to devices in other regions of the heart, the cardiovascular system, or the body.

Moreover, the cardiac assist devices herein can continuously or nearly continuously monitor and assess cardiac function while the device is in the patient. This can be advantageous over methods that can only estimate cardiac function at specific intervals of time. For example, continuous monitoring may allow more rapid detection of cardiac deterioration. Additionally, if the cardiac assist device is already in the patient, the cardiac function can be measured without having to introduce an additional catheter into a patient.

Assessment of cardiac function by the cardiac assist devices presented herein is enabled, at least in part, by the minimally-invasive nature of the cardiac assist devices. Unlike some invasive cardiac assist devices which shunt blood out of the heart, the cardiac assist devices presented herein reside within the heart and work in parallel with native ventricular function. This allows the cardiac assist devices presented herein to be sensitive enough to detect native ventricular function unlike some more invasive devices. Thus, the systems, devices, and methods enable the use of cardiac assist devices not only as support devices, but also as diagnostic and prognostic tools. The cardiac assist devices can essentially function as active catheters that extract information about cardiac function by hydraulically coupling with the heart. In some implementations, the cardiac assist devices operate at a constant level (e.g., constant rotational speed of a rotor), while power delivered to the assist device is measured. In certain implementations, the speed of the rotor of the cardiac assist device may be varied (e.g., as a delta, step, or ramp function) to further probe the native heart function.

Heart function parameters indicative of native heart function can be determined from measurements of intravascular and/or ventricular pressure and pump parameters/signals (a "parameter" can represent a signal and/or operating state of the heart pump). For example, the heart parameters can be determined from aortic pressure and pump motor current. This determination can be made using a model of the combined heart and heart pump system. In one method of cardiac function determination, the model includes accessing predetermined curves. This model may be a look-up table or a predetermined/normalized pump performance curve or calibration curve or any other suitable model. A look-up table may include a set of curves showing the power required to maintain a rotational speed and pressure head are determined as a function of pump flow, and a set of curves relating the pressure head and the flow characteristics of the heart are also determined. For example, a look-up table may indicate that a particular aortic pressure and motor current corresponds to a particular left ventricular end diastolic pressure (LVEDP). In another method of cardiac function determination, the performance of the pump is represented by showing the pressure head as a function of the pump's motor current draw, the current draw acting as a surrogate for the power or load on the pump. The relationship between the motor current draw and the pressure head during the cardiac cycle describes a hysteresis curve or loop. Cardiac state and functions, including LVP and LVEDP can be extracted from the relationship between the motor current draw and pressure head. Besides or in addition to LVEDP, cardiac function can be quantified in several different ways using the cardiac assist devices presented herein. For example, heart function can be expressed as contractility, stroke volume, ejection fraction, chamber pressure, stroke work, cardiac output, cardiac power output, LVEDP, preload state, afterload state, heart rate, and/or heart recovery.

To accurately determine these heart parameters, hysteresis between the pressure measurements (e.g., difference between aortic pressure and left ventricular pressure, or the aortic pressure alone) and the motor current measurements may be taken into account. This hysteresis can be accounted for by detecting the phase of the cardiac cycle corresponding to a given pair of pressure and current measurements. This can be done using at least two methods that differentiate diastolic filling from the other phases of the cardiac cycle. Both methods identify critical points which indicate the beginning and end of diastolic filling. The first method uses the aortic pressure waveform and identifies key characteristics in the curve, such as the dicrotic notch, to indicate the beginning of diastolic filling. This method can also use the beginning of aortic filling to indicate the end of diastolic ventricular filling. The second method uses ECG data timed with the pressure tracings to identify two key characteristics that demarcate diastolic filling. These characteristics are preferably the beginning of the QRS complex and the end of the T-wave. If there is noise in the signal, it can be more reliable to detect the peak of the QRS complex (the R-wave) and the peak of the T-wave. Furthermore, in some implementations, the hysteresis between the pressure and motor parameter measurements can itself be used to determine the phase of the cardiac cycle.

The systems, devices, and methods presented herein also account for variations in heart rate. If unaccounted for, changes in heart rate may affect the resolution of the waveforms and hence the accuracy of the heart parameter estimations. For example, a higher heart rate at a given sampling frequency results in fewer samples per cardiac cycle. The number of samples per cardiac cycle is critical for capturing key features used to account for hysteresis, such as the dicrotic notch, as well as key points in the pressure waveform such as the LVEDP. If the sampling number is too low, these features can be missed since the number of samples in the region of interest decrease. However, the sensitivity to heart rate can be reduced or eliminated in some implementations by not performing waveform analysis over a fixed time period instead of cycle by cycle. For example, in some implementations, calculations are performed over 10-30 seconds and averaged to reduce the impact of artifacts. Such averaging is possible for some metrics, such as LVEDP, because they do not have very high beat-to-beat variability, at least within short time periods (e.g., ~1 minute). Using multiple cycles allows the number of samples in the region of interest to be independent of heart rate. Moreover, conglomerating multiple measurements can improve the resolution of phases of the cardiac cycle. Furthermore, effects of insufficient sampling can be further negated by increasing the sampling period.

The systems, devices, and methods presented herein also detect suction events, which occur when a pump inlet is fully or partially occluded. Conventional suction detection systems are insufficiently sensitivity to detect minor suction events. In contrast, the systems, devices, and methods presented herein can detect minor suction and when during the cardiac cycle the suction is occurring. These determinations may be based on hysteresis of the motor current-aortic pressure curve. This improved method can detect suction sooner and provide the user with information on how to prevent or decrease continued or worsening suction. Furthermore, in some implementations, the systems, methods, and devices can predict suction events by detecting an unfavorable cardiac cycle flow state which could lead to suction events.

FIG. 1 shows an exemplary prior art cardiac assist device located in a heart 102. The heart 102 includes a left ventricle 103, aorta 104, and aortic valve 105. The intravascular heart pump system includes a catheter 106, a motor 108, a pump outlet 110, a cannula 111, a pump inlet 114, and a pressure sensor 112. The motor 108 is coupled at its proximal end to the catheter 106 and at its distal end to the cannula 111. The motor 108 also drives a rotor (not visible in figure) which rotates to pump blood from the pump inlet 114 through the cannula 111 to the pump outlet 110. The cannula 111 is positioned across the aortic valve 105 such that the pump inlet 114 is located within the left ventricle 103 and the pump outlet 110 is located within the aorta 104. This configuration allows the intravascular heart pump system 100 to pump blood from the left ventricle 103 into the aorta 104 to support cardiac output.

The intravascular heart pump system 100 pumps blood from the left ventricle into the aorta in parallel with the native cardiac output of the heart 102. The blood flow through a healthy heart averages about 5 liters/minute, and the blood flow through the intravascular heart pump system 100 can be a similar or different flow rate. For example, the flow rate through the intravascular heart pump system 100 can be 0.5 liters/minute, 1 liter/minute, 1.5 liters per minute, 2 liters/minute, 2.5 liters/minute, 3 liters/minute, 3.5 liters/minute, 4 liters/minute, 4.5 liters/minute, 5 liters/minute, greater than 5 liters/minute or any other suitable flow rate.

The motor 108 of the intravascular heart pump system 100 can vary in any number of ways. For example, the motor 108 can be an electric motor. The rotor 108 can be operated at a constant rotational velocity to pump blood from the left ventricle 103 to the aorta 104. Operating the motor 108 to maintain a constant rotor speed generally requires supplying the motor 108 with varying amounts of current because the load on the motor 108 varies during the different stages of the cardiac cycle of the heart 102. For example, when the mass flow rate of blood into the aorta 104 increases (e.g., during systole), the current required to operate the motor 108 increases. This change in motor current can thus be used to help characterize cardiac function as will be discussed further in relation to the following figures. An electric motor current may be measured, or alternatively a magnetic field current may be measured. Detection of mass flow rate using motor current may be facilitated by the position of the motor 108, which is aligned with the natural direction of blood flow from the left ventricle 103 into the aorta 104. Detection of mass flow rate using motor current may also be facilitated by the small size and/or low torque of the motor 108. The motor 108 of FIG. 1 has a diameter of about 4 mm, but any suitable motor diameter may be used provided that the rotor-motor mass is small enough to be influenced by the inertia of pulsatile blood. The rotor-motor mass may be influenced by the pulsatile mass flow of blood to produce a discernable and characterizable effect on the motor parameter. In some implementations, the diameter of the motor 108 is less than 4 mm.

In certain implementations, one or more motor parameters other than current, such as power delivered to the motor 108, speed of the motor 108, or electro-magnetic field are measured. In some implementations, the motor 108 in FIG. 1 operates at a constant velocity. In some implementations, the motor 108 may be external to the patient and may drive the rotor by an elongate mechanical transmission element, such as a flexible drive shaft, drive cable, or a fluidic coupling.

The pressure sensor 112 of the intravascular heart pump system 100 can be an integrated component (as opposed to separate diagnostic catheter) and can be configured to detect pressure at various locations of the system 100 such as adjacent to a proximal end of the motor 108. In certain implementations, the pressure sensor 112 of the intravascular heart pump system 100 can be disposed on the cannula 111, on the catheter 106, on a portion of the system 100 external to the patient's body, or in any other suitable location. The pressure sensor 112 can detect blood pressure in the aorta 104 when the intravascular heart pump system 100 is properly positioned in the heart 102, or for right heart support devices can detect pressure in the inferior vena cava (IVC) or the pulmonary artery. The blood pressure information can be used to properly place the intravascular heart pump system 100 in the heart 102. For example, the pressure sensor 112 can be used to detect whether the pump outlet has passed through the aortic valve 105 into the left ventricle 103 which would only circulate blood within the left ventricle 103 rather than transport blood from the left ventricle 103 to the aorta 104. The pressure sensor in FIG. 1 detects the absolute pressure at a certain point in the patient's vasculature, for example, in the aorta. In other embodiments, the pressure sensor detects absolute pressure in the pulmonary artery or venous system. In other embodiments, the pressure sensor detects the pressure head or the delta pressure in the system, which can be equal to the aortic pressure less the left-ventricular pressure.

In addition to aiding placement of the intravascular heart pump system 100, one or more algorithms can be applied to the data obtained by the pressure sensor 112 in order to detect the cardiac phase of the heart 102. For example, the data obtained by the pressure sensor 112 can be analyzed to detect a dicrotic notch that indicates the beginning of diastolic filling. The dicrotic notch is a small downward deflection in the arterial pulse or pressure contour immediately following the closure of the semilunar valves. This feature can be used as a marker for the end of systole or the ejection period. Because the measured pressure head often contains more noise features than the measured motor current, the motor current can be used to 'gate' a period of time in which the dicrotic notch is likely to be identified, and the corresponding time period of the measured pressure head can then be identified and analyzed. Other features may also be detected as indicative of the LVEDP, for example, a change in the motor speed, the presence of an R-peak in ECG data, or changes in curvature or local slope of a parameter over time.

The intravascular heart pump system 100 can be inserted in various ways, such as by percutaneous insertion into the heart 102. For example, the intravascular heart pump system can be inserted through a femoral artery (not shown), through an axillary artery (not shown), through the aorta 104, across the aortic valve 105, and into the left ventricle 103. In certain implementations, the intravascular heart pump system 100 is surgically inserted into the heart 102. In some implementations, the intravascular heart pump system 100, or a similar system adapted for the right heart, is inserted into the right heart. For example, a right heart pump similar to the intravascular heart pump system 100 can be inserted through the inferior vena cava, bypassing the right atrium and right ventricle, and extending into the pulmonary artery. In certain implementations, the intravascular heart pump system 100 may be positioned for operation in the vascular system outside of the heart 102 (e.g., in the aorta 104). By residing minimally invasively within the vascular system, the intravascular heart pump system 100 is sufficiently sensitive to allow characterization of native cardiac function. Additionally, surgically implanted devices described below such as LVAD's would be sensitive to change in native cardiac function, although less sensitive that the intravascular heart pump 100.

Figure 2:
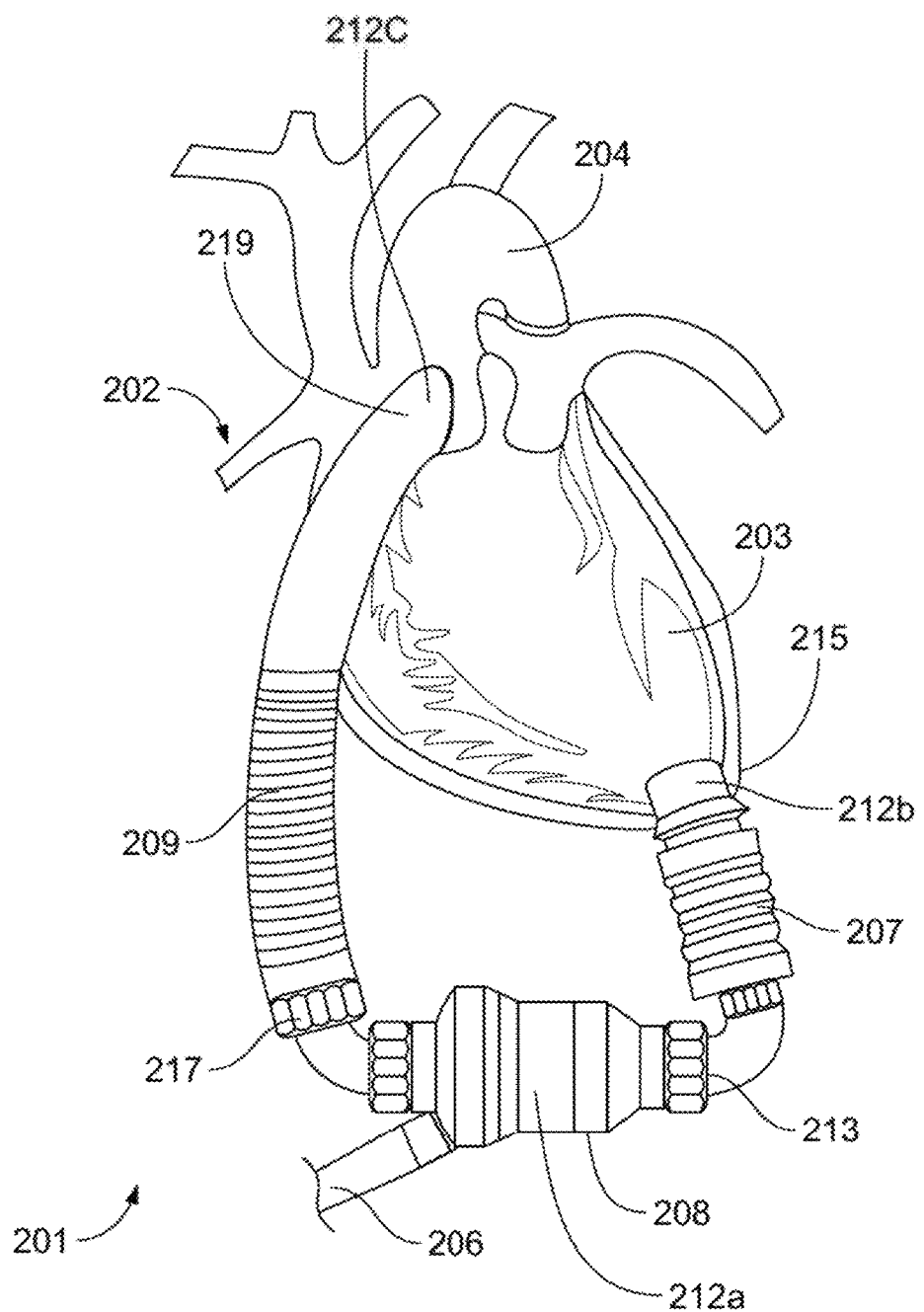
FIG. 2 shows a prior art LVAD heart pump system located in the heart.

FIG. 2 shows an exemplary prior art heart assist device 201 located outside a heart 202. The heart 202 includes a left ventricle 203 and an aorta 204. The heart assist device 201 includes a motor 208, an inflow conduit 207, an outflow conduit 209, a first sensor 212a, a second sensor 212b, a third sensor 212c, and a catheter 206. The inflow conduit 207 is coupled at a first end 213 to a first side of the motor 208 and at a second end 215 to an apex of the left ventricle 203. The outflow conduit 209 is coupled at a first end 217 to a second side of the motor 208 and at a second end 219 to the ascending aorta 204. The motor 208 also drives a rotor (not visible in the figure) which rotates to pump blood from the apex of the left ventricle 203 through the inflow conduit 207 into the outflow conduit 209 and to expel the blood into the aorta 204. The heart assist device 201 is configured to pump blood from the left ventricle 203 to the ascending aorta 204 to support cardiac output.

The heart assist device 201 pumps blood from the left ventricle 203 into the aorta 204 bypassing the aortic valve (not visible in figure) and transporting the blood through the inflow conduit 207 and the outflow conduit 209 around the heart 202, rather than within the heart 202. The blood flow through the heart assist device 201 can deliver a similar or greater flow rate than the flow rate of the prior art intravascular heart pump system 100 of FIG. 1. The heart assist device 201 can be surgically implanted in a patient such that the second end 219 of the outflow conduit 209 and the second end 215 of the inflow conduit 207 are surgically grafted to the heart 202 at the ascending aorta 204 and the left ventricle 203, respectively. The motor 208 can be connected by a drive line (not shown) through a catheter 206 to a console (not shown) located outside the patient's body. The rotor (not shown) can run at a constant, or substantially constant, speed. The power supplied to the motor 208 may be monitored at the console to determine a pump flow rate or other characteristics of the pump performance.

The first sensor 212a, second sensor 212b, and third sensor 212c may be similar to the pressure sensor 112 in FIG. 1. The sensors 212a-c can be pressure sensors used to determine blood pressure in the aorta 204 or blood pressure in the left ventricle 203, or may be placed to determine the blood pressure and blood flow through the inflow conduit 207 and outflow conduit 209. The blood pressure in the aorta 204 or the left ventricle 203 can be displayed to a user and/or can be used to determine operating parameters of the heart assist device 201. The blood flow or pressure within the inflow conduit 207 and outflow conduit 209 can also be displayed to a user and used to monitor the heart assist device 201. The first sensor 212a can also be a sensor of the pump motor 208 power which can be used to determine a pump flow through the heart assist device 201.

Figure 3:
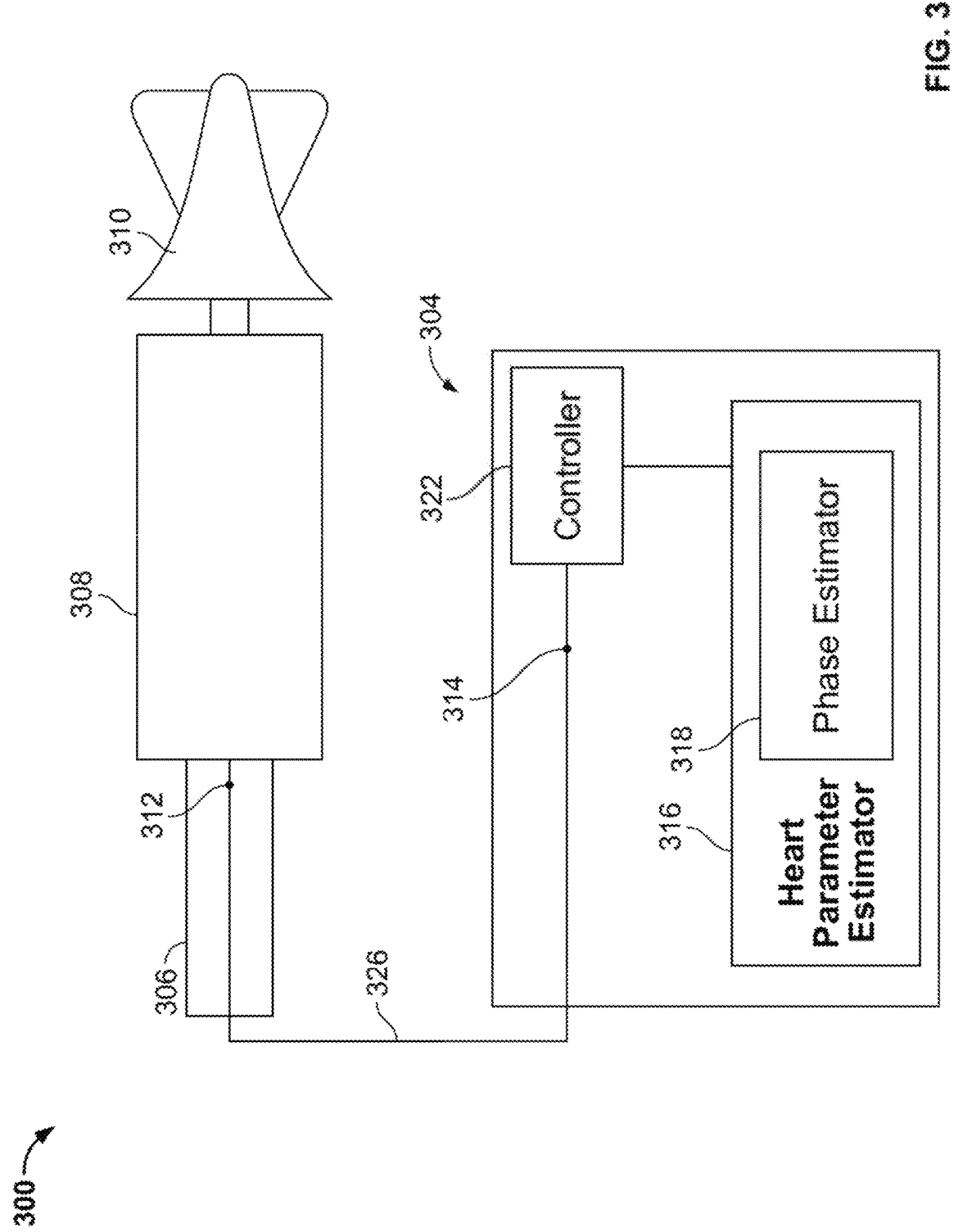
FIG. 3 shows an illustrative heart pump system configured to estimate cardiovascular parameters according to certain implementations.

FIG. 3 shows an illustrative heart pump system 300, according to certain implementations, configured to estimate heart parameters indicative of cardiac function. The heart pump system 300 may be similar to or the same as the intravascular heart pump system 100 of FIG. 1 or the heart assist system 201 of FIG. 2. The heart pump system 300 may operate within a heart, partially within the heart, outside the heart, partially outside the heart, partially outside the vascular system, or in any other suitable location in a patient's vascular system. The heart pump system 300 includes a heart pump 302 and a control system 304. All or part of the control system 304 may be in a controller unit separate/remote from the heart pump 302. In some implementations, the control system 304 is internal to the heart pump 302. The control system 304 and the heart pump 302 are not shown to scale.

The heart pump 302 can include a catheter 306, a motor 308, a rotor 310, and a pressure sensor 312. The motor 308 can be coupled to a distal region of the catheter 306, and as mentioned previously, can alternatively be located outside of the patient's body and can communicate with the motor 308 via a drive shaft, drive cable, or fluidic connection. The motor 308 is also coupled to the rotor 310 such that operation of the motor 308 causes the rotor 310 to rotate and pump blood. The pressure sensor 312 can be positioned along the catheter in any number of locations inserted into the patient's cardiovascular system such that that pressure sensor 312 can detect blood pressure when the heart pump 302 is inserted into a patient's vascular system. In implementations in which the heart pump 302 is an intravascular heart pump 302, such as the intravascular heart pump system 100 of FIG. 1, the heart pump 302 can be delivered to the left ventricle, and the pressure sensor 312 can sense aortic pressure when the intravascular heart pump 302 is properly positioned in the left ventricle. In some implementations, the pressure sensor 312 is positioned in a chamber or vessel separated by a valve from a chamber of interest. For example, the pressure sensor 312 may be positioned in the aorta when the rotor 310 is positioned in the aorta, or the pressure sensor 312 may be positioned in the inferior or superior vena cava with the rotor 310 while the outlet of the pump is in the pulmonary artery. In some implementations, the heart system is configured such that the rotor 310 is positioned in the aorta when an inlet of the pump is placed in the left ventricle.

The control system 304 can include a controller 322, a current sensor 314, and a heart parameter estimator 316. The controller 322 supplies current to the motor 308 by an electrical connection 326 such as through one or more electrical wires. The current supplied to the motor 308 via the electrical connection 326 is measured by the current sensor 314. The load that the motor 308 of a mechanical pump experiences is pressure head, or the difference between the aortic and left ventricular pressure. The heart pump 302 experiences a nominal load during steady state operation for a given pressure head, and variations from this nominal load are a result of changing external load conditions, for example the dynamics of left ventricular contraction. Changes to the dynamic load conditions alter the motor current required to operate the rotor 310 at a constant, or substantially constant, speed. The motor may operate at a speed required to maintain the rotor 310 at a set speed. As a result, the motor current drawn by the motor to maintain the rotor speed can be monitored and used to understand the underlying cardiac state. The cardiac state can be even more precisely quantified and understood by simultaneously monitoring the pressure head during the cardiac cycle using a pressure sensor 312 with regard to the motor current to generate a hysteresis loop of quantitative pump performance that may be visually assessed to determine changes in the cardiac state and function. The heart parameter estimator 316 receives current signals from the current sensor 314 as well as pressure signals from the pressure sensor 312. The heart parameter estimator 316 uses these current and pressure signals to characterize the heart's function. The heart parameter estimator 316 may access stored look-up tables to obtain additional information to characterize the heart's function based on the pressure and current signals. For example, the heart parameter estimator 316 may receive an aortic pressure from the pressure sensor 312, and using look-up tables, may use the aortic pressure to determine a delta pressure.

The controller 322 can store the current signals from the current sensor 314 and the pressure signals from the pressure sensor 312 in a database in a memory or server (not shown). The database and memory can be external to the controller 322 or included within the controller 322. The controller 322 can store the signals as arrays in the database having particular associated addresses, and may also record time with the signals. The controller 322 can also store determined cardiac parameters, such as LVEDP, in the memory for comparison to previously stored cardiac parameters. The controller 322 accesses the hysteresis curve by accessing an address of a database in the memory. Based on the address, the controller 322 selects a first array in which are stored a plurality of data points corresponding the measured motor parameter over time. The controller 322 also selects a second array in which are stored a plurality of data points corresponding to the measured pressure or other physiological parameter over time. The controller 322 associates the first data points corresponding to the motor parameter with the second data points corresponding to the physiological parameter at each point in time that a measurement was taken. The controller 322 may then display the matched data points to a user on a screen or other display as a hysteresis curve. Alternatively, the controller 322 can iterated through the matched data points to calculate a cardiac parameter.

The heart parameter estimator 316 can characterize cardiac function and determine cardiac parameters according to two distinct methods. In a first method, the heart parameter estimator 316 utilizes predetermined pressure-current curves to extract information about cardiac function and heart parameters. Using this method, the heart parameter estimator 316 compares the power required to maintain a rotational speed of the pump rotor 310 and the pressure head, defined as the pressure gradient across the pump, to predetermined performance curves which illustrate the power and pressure head as a function of the pump flow and to predetermined system curves relating the pressure head and motor current (predetermined pressure-current curves). Using the performance and system curves, the heart parameter estimator 316 characterizes the pump behavior in order to extract information about heart parameters and cardiac function.

In a second method, the heart parameter estimator 316 uses a best fit algorithm to determine heart parameters related to cardiac function. The heart parameter estimator 316 accesses a modified representation of pump performance from the pressure head as a function of the motor current draw. The motor current draw acts as a surrogate for the power or load on the pump. The load on the pump at a given rotor RPM is determined by the fluid motor torque described by the equation $\tau = H \cdot d$, where the torque, $\tau$, is determined by the pressure head, H, and volumetric displacement per revolution, d. Torque is directly related to the power requirements of the pump by the equation:

$$P_{electrical} = V * I = \frac{\tau * \omega}{\eta}$$

where the electrical power requirement ($P_{electrical}$) is a product of the voltage (V) and current (I), and is related to the pump torque ($\tau$), rotational speed ($\omega$), and combined electrical and mechanical efficiency ($\eta$). Because the motor speed and efficiency are relatively constant and are known, the fluid motor torque can be determined from the electrical power of the pump. The relation between the power and motor current may vary according to pump design, but motor current is an operationally measured value for most pumps. The motor current is typically directly related to the torque, and therefore to the load on the pump.

The pressure head is the load that the mechanical pump feels, and the pressure head is the difference between the aortic and left ventricular pressure, which changes throughout the cardiac cycle with the addition of the external flow of blood generated by cardiac contraction. Pump operation in the pulsatile environment of the heart alternates between a steady state ventricular filling and a ventricular ejection. The motor current required to generate a specific RPM of the rotor is dependent on both the pressure head and the cardiac state, and this results in a hysteresis loop as the motor experiences active cardiac contraction followed by ventricular filling during relaxation. The resulting motor current hysteresis is a complete representation of the mechanical pump performance curve as it integrates the effects of external flow and pressure changes.

Classically, methods of measuring LVEDP have been indirect and discontinuous. One common method of measuring LVEDP is by using a Swan-Ganz catheter, in which the LVEDP is inferred through this catheter by wedging an inflated balloon into the pulmonary artery and using the pulmonary vasculature and the left atrium as a fluid column to obtain pressures in the left ventricle during diastole. This measurement is indirect and often includes significant measurement error, noise, and lack of reliability. Further, because the balloon in the pulmonary artery cannot remain inflated, measurements are discontinuous. An alternative method that has historically been used to measure the LVEDP is to use a pressure transducer catheter that is inserted into the left ventricle of the heart. This captures the entire pulsatile pressure waveform through a few cardiac cycles; but the catheter cannot remain in the patient for extended periods or at the bedside. Other methods to non-invasively predict the LVEDP have been developed using Doppler echocardiogram or ultrasound. Unfortunately, they too are prone to the same issues and cannot provide continuous pressure estimations over extended periods of time.

The LVEDP can be determined from the motor current drawn and pressure head for a particular rotor speed. Assuming that the motor current variations corresponding to slight motor speed variations at end diastole are linear, these variations can be corrected by linear scaling according to the equation:

$$i_c = i_m * \frac{\omega_0}{\omega}$$

where the speed corrected motor current ($i_c$) is equal to the product of the measured motor current ($i_m$), and a ratio of the desired fixed motor speed ($\omega_0$) and real motor speed ($\omega$). This is a safe assumption as motor speed variation is minimal (±0.5%). The relationship between the motor current and the pressure head can be characterized, for example, by fitting an equation to the data. The speed corrected motor current ($i_c$) can be plotted against the measured pressure head and the relationship can then be fit to a high-order polynomial, for example by using an $R^2$ optimization to produce a fourth order polynomial with pressure head as a function of motor current. Alternatively, any best fit algorithm can be applied to the plot of the measured pressure head and the motor current in order to estimate the hysteresis loop. For example, the plot of the parameters can be fit to an ellipse or an angled or truncated ellipse to estimate the shape of the hysteresis loop. The equation determined by the best fit algorithm can then be used to extract information about the cardiac function, for example, the LVP can be extracted from an inflection point of the hysteresis curve, and the phases of filling, relaxation, and ejection can be identified. Other parameters can be determined from points on the hysteresis loop, the size or shape of the hysteresis loop, changes in the size and shape of the hysteresis loop, local slope change, curvature change, or the area within the hysteresis loop. Further, coefficients for the fit can then be used to predict LVEDP for a given corrected motor current at a given motor RPM setting. These parameters enable a healthcare professional to better understand a current cardiac function of a patient and to provide appropriate cardiac support.

Other heart parameters indicative of cardiac function can also be determined by the heart parameter estimator 318 based on a comparison of measured values to look-up tables or from the shape and values of hysteresis loops formed from the measured motor parameters and pressure during the cardiac cycle. For example, changes in contractility can be related to the variation in slope of the pressure during contraction of the heart (dP/dt). The cardiac output is determined based on the flow rate of the blood through and past the pump. The stroke volume is an index of left ventricular function which formula SV=CO/HR, where SV is the stroke volume, CO is the cardiac output, and HR is the heart rate. Stroke work is the work done by the ventricle to eject a volume of blood and can be calculated from the stroke volume according to the equation SW=SV*MAP, where SW is the stroke work, SV is the stroke volume, and MAP is the mean arterial pressure. Cardiac work is calculated by the product of stroke work and heart rate. Cardiac power output is a measure of the heart function in Watts calculated using the equation CPO=mAoP*CO/451, where CPO is the cardiac power output, mAoP is the mean aortic pressure, CO is the cardiac output, and 451 is a constant used to convert mmHG×L/min into Watts. The ejection fraction can be calculated by dividing the stroke volume by the volume of blood in the ventricle. Other parameters, such as chamber pressure, preload state, afterload state, heart recovery, flow load state, variable volume load state, and/or cardiac cycle flow state can be calculated from these values or determined by examination of the hysteresis loop.

An active catheter mounted heart pump within the left ventricle provides an avenue to direct and continuous LVEDP measurement during the most critical times, which is when the device would be in use. Without additional intervention, this diagnostic measurement can be obtained by leveraging parameters from the device. In addition, this device can obtain diagnostic metrics that incorporate more than a single point in the cardiac cycle. While useful, LVEDP remains only a single point of time out of the entire cardiac cycle. More holistic metrics comprising of information from the entire cardiac cycle can give more information about the state of the heart and be more representative of the actual state of the heart.

The predetermined pressure-current curves can be measured using a mock circulatory loop, animal data, or clinical data. For example, a mock circulatory loop (MCL) with varying contractile, preload, and afterload conditions may be used to define the bounds of pump performance, while an animal model may be used to delineate biological variability and pathology. Using an MCL for characterization and animal models for validation is an effective means for relating performance of the heart pump 302 to heart function. Although baseline motor current may vary between pumps, the current measurement from each pump can be normalized to generate a normalized current waveform. In some implementations, heart pumps are binned separately in 30 mA ranges based on their current responses to normalize calculations for approximate flow rate.

The heart phase information may significantly improve the accuracy of the heart parameter estimator 316 by accounting for the effect of hysteresis in the pressure-current curve. As will be discussed further below, the pressure-current curves may exhibit hysteresis due to the phases of the heart cycle. Therefore, to compare pressure and current data points accurately, the phase of the heart must be taken into account. Otherwise, pressure and current data collected during systole might be compared with non-analogous reference pressure and current data collected during diastole, for example, which may skew the estimate of the heart parameter.

The estimation of the heart parameter by the heart parameter estimator 316 can be continuous or nearly continuous while the heart pump 302 is implanted in the heart. This can be advantageous over conventional catheter-based methods that only allow sampling of cardiac function at specific times. For example, continuous monitoring may allow more rapid detection of cardiac deterioration. Additionally, if the cardiac assist device is already in the patient, the cardiac function can be measured without having to introduce an additional catheter into a patient.

After the heart parameter is estimated by the heart parameter estimator 316, the heart parameter is output to the controller 322. The controller 322, in turn, supplies a control signal for driving the motor 308. In some implementations, the controller 322 operates the motor 308 at a fixed set point. The set point may be a fixed rotational velocity or flow rate. For example, the controller may supply a varying voltage to hold a constant rotational velocity of the rotor 310 by the motor 308 independent of pre-load and/or afterload. The controller 322 may also allow a user to vary the rotational velocity of the rotor 310, and in some implementations, the motor 308. For example, the user may select a new set point (e.g., by setting a new desired flow rate or rotational speed) or may select a time-varying input signal (e.g., a delta, step, ramp function, or sinusoid). In some implementations, the fixed set point may be an amount of power delivered to the motor 308. In certain implementations, the heart parameter estimated by the heart parameter estimator 316 is displayed to a physician and the physician manually adjusts the set point of the motor at the controller 322.

The controller 322 can adjust the set point sent to the controller 322 based on the heart parameter estimated by the heart parameter estimator 316. For example, the degree/level of support (i.e., speed of the rotor and thus volumetric flow rate of blood delivered by the device) can be increased when heart function is deteriorating or the degree of support can be decreased when heart function is recovering. This can allow the device to dynamically respond to changes in heart function to promote heart recovery and to gradually wean a patient off of the therapy.

Figure 4:
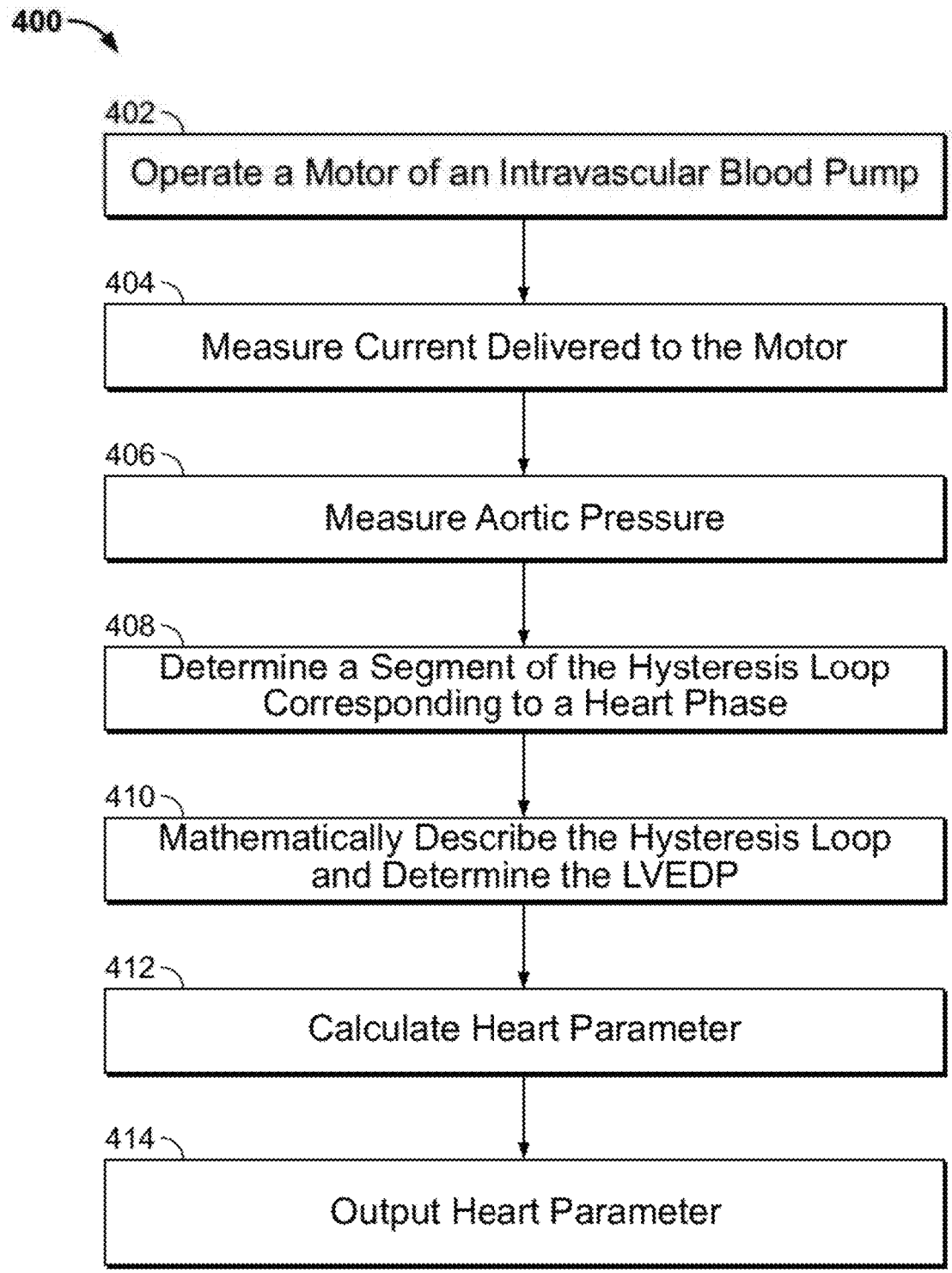
FIG. 4 shows a process for determining a heart parameter indicative of heart function according to certain implementations.

FIG. 4 shows a process 400 for determining a heart parameter indicative of heart function. The process 400 can be performed using the intravascular heart pump system 100 of FIG. 1, the heart assist device 201 of FIG. 2, the heart pump system 300 of FIG. 3, or any other suitable heart pump. In step 402, the motor of a heart pump is operated. The motor may be operated at a rotational speed necessary to maintain a constant or substantially constant rotational speed of the rotor. In step 404, the current delivered to the motor is measured and the motor speed is measured. The current may be measured using a current sensor (e.g., current sensor 314) or by any other suitable means. In step 406, the aortic pressure is measured. The aortic pressure may be measured by a pressure sensor coupled to the heart pump, by a separate catheter, by a noninvasive pressure sensor, or by any other suitable sensor. The pressure sensor may be an optical pressure sensor, an electrical pressure sensor, a MEMS sensor, or any other suitable pressure sensor. In some implementations, ventricular pressure is measured in addition to or in alternative to measuring aortic pressure.

In some implementations, additional steps may be performed after measuring the current delivered to the motor and the aortic pressure. For example, in some implementations, the aortic pressure may be scaled by a factor determined from a look-up table in order to find the differential pressure over time. In some implementations, the measured current and pressure data is smoothed in order to provide a less noisy signal.

In step 408, a segment of the hysteresis loop formed by the measured current delivered to the motor and measured aortic pressure is determined, corresponding to a phase of the heart. The segmentation and phase estimation can act as a filter for the pressure and current signals because it can allow pressure and current signals to be compared to pressure and current signals that occurred during corresponding stages of the cardiac cycle. The segmentation and phase estimation may be based on the pressure information received in step 406 and may involve locating fiducial points in the pressure information indicative of the heart phase. In some implementations, the dicrotic notch in the pressure signal is detected to indicate the beginning of diastolic filling. The dicrotic notch is a small downward deflection in the arterial pulse or pressure contour immediately following the closure of the semilunar valves. This dicrotic notch can be used as a marker for the end of systole and hence approximately the beginning of diastole.

In some implementations, the segmentation or phase estimation is entirely or partially based on ECG data. Such ECG data may be timed with the pressure tracings. The characteristic in the ECG used to estimate the heart phase may be the beginning of the QRS complex and the end of the T-wave. If there is noise in the ECG signal, it may be more reliable to detect the peak of the QRS complex (e.g., the R-wave) and the peak of the T-wave. The R-peak of the QRS waveform may also be used to identify timing of various parameters, such as the time period in which the LVEDP will be found, as the R-peak corresponds to the end cycle of the diastole. In phase estimation methods using either pressure signals or ECG signals, an offset from the detected feature may be used to more accurately identify filling phases since actual filling occurs slightly before or after these identified landmarks. A combination of both pressure signal-based and ECG-based methods can allow more reliable identification of the heart phase. The weighting between the two methods can be optimized using datasets having known filling time parameters, known left ventricular pressures, and high signal to noise ratios.

In addition to ECG data, the segmentation and heart phase estimation can also be entirely or partially based on the motor parameter or a motor speed, aortic pressure slope, respiratory variation, or any other suitable physiological or device parameter. In some implementations, the segmentation and heart phase estimation is determined based on any single one of these parameters or on a combination of any number of them.

In step 410, the hysteresis loop is mathematically described and the LVEDP is determined based on the mathematical description. The hysteresis loop can be characterized by fitting an equation to the data, for example describing the loop by a polynomial function based on Euler's equation describing an ellipse, and the elliptical fit can be used to calculate the LVEDP. Mathematical fitting of the hysteresis loop additionally enables the comparison of the size, shape and area of the loop or of segments of the loop over time, as well as analysis of changes in local slope or curvature of segments of the loop to measure changes in cardiac parameters.

In some implementations, a look-up table is referenced to determine a heart parameter indicative of cardiac function based on the motor parameter, the pressure, and the heart phase. In some implementations, the table may embody predetermined pressure-current curves.

At step 412, a heart parameter is calculated. Determining the heart parameter can involve determining a point on the hysteresis loop based on the mathematical fit, integrating the area of a section of the hysteresis loop, or mapping the measured current and pressure to heart parameters using look-up tables. The section of the hysteresis loop can be segmented based on the Euler's equation elliptical fit and the bilateral line as will be described further with regard to FIG. 13, such that the ellipse consists of multiple segments each having at least one straight edge. The segments can be translated and rotated, before being integrated by Riemann sums.

The heart phase information extracted from the hysteresis loop may be binary (e.g., diastole or systole) or more fine-grained (e.g., systole, diastolic relaxation, and diastolic filling). The heart phase may be one of cardiac ejection, diastolic filling, and diastolic relaxation. The determined heart parameter can be contractility, stroke volume, ejection fraction, chamber pressure, stroke work, cardiac output, cardiac power output, left ventricular end diastolic pressure (LVEDP), preload state, afterload state, heart rate, heart recovery, flow load state, variable volume load state, cardiac cycle volume load state, and/or cardiac cycle flow state. Left ventricular end diastolic pressure (LVEDP) is a single point measurement that is often used by physicians to evaluate cardiac health. LVEDP is significantly elevated in many cases of heart failure, indicating ventricular overload. This is largely due to a shift in the Frank-Starling relationship because of a change in the end diastolic pressure volume ratio (EDPVR). As patients move closer to heart failure, the Frank-Starling curve shifts downward, such that a given pressure (preload) results in a lower stroke volume. Because of this shift, at a given cardiac output for a patient, the LVEDP can be indicative of the state of the heart given all other conditions remain relatively constant. Measuring these changes in LVEDP can be valuable for monitoring the progression of the patient either towards heart failure or towards recovery thus allowing clinicians to adjust the required therapy accordingly.

Alternatively, if a reference table is used, the look-up table may accept as its inputs pressure, motor current, and heart phase. The predetermined pressure-current curves can be measured using a mock circulatory loop, animal data, or clinical data. For example, a mock circulatory loop (MCL) with varying contractile, preload, and afterload conditions may be used to define the bounds of pump performance, while an animal model may be used to delineate biological variability and pathology. Using an MCL for characterization and animal models for validation is an effective means for relating performance of the heart pump to heart function. Although baseline motor current may vary between pumps, each pump can be normalized to generate a normalized current waveform.

The heart phase information from step 408 may significantly improve the accuracy of the heart parameter estimation by accounting for the effect of hysteresis in the pressure-current curve. The pressure-current curves exhibit hysteresis due to the phases of the heart cycle. Therefore, to compare pressure and current data points accurately, the phase of the heart must be taken into account. Otherwise, pressure and current data collected during systole might be compared with non-analogous reference pressure and current data collected during diastole, for example, which may skew the estimate of the heart parameter.

In step 414, the heart parameter is output. The output and/or the determination of the heart parameter can be continuous or nearly continuous while the heart pump is implanted in the heart. This can be advantageous over conventional catheter-based methods that only allow sampling of cardiac function at specific times during the cardiac cycle or at discrete points in time. For example, continuous monitoring of the heart parameter may allow more rapid detection of cardiac deterioration. Continuous monitoring of the heart parameter can illustrate changes in the heart condition over time, for example by outputting a continuous hysteresis parameter associated with the phases of the heart that may show differences as the condition of the heart changes. Additionally, if the cardiac assist device is already in the patient, the cardiac function can be measured without having to introduce an additional catheter into a patient. The heart parameter may be output using any suitable user interface or report, such as the user interfaces described below with regard to FIGS. 20A and 20B.

In some implementations, the power delivered to the motor is adjusted based on the heart parameter. The power delivered to the motor can be adjusted automatically by a controller (e.g., controller 322) or manually (e.g., by a healthcare professional). The degree of support can be increased when a patient's heart function is deteriorating or the degree of support can be decreased when a patient's heart function is recovering, thus allowing the patient to be gradually weaned off of the therapy. This can allow the device to dynamically respond to changes in heart function to promote heart recovery. It can also be used to intermittently modulate pump support and to diagnose how the heart reacts, e.g., if it can take over the pumping function from the heart pumping device.

Figure 5:
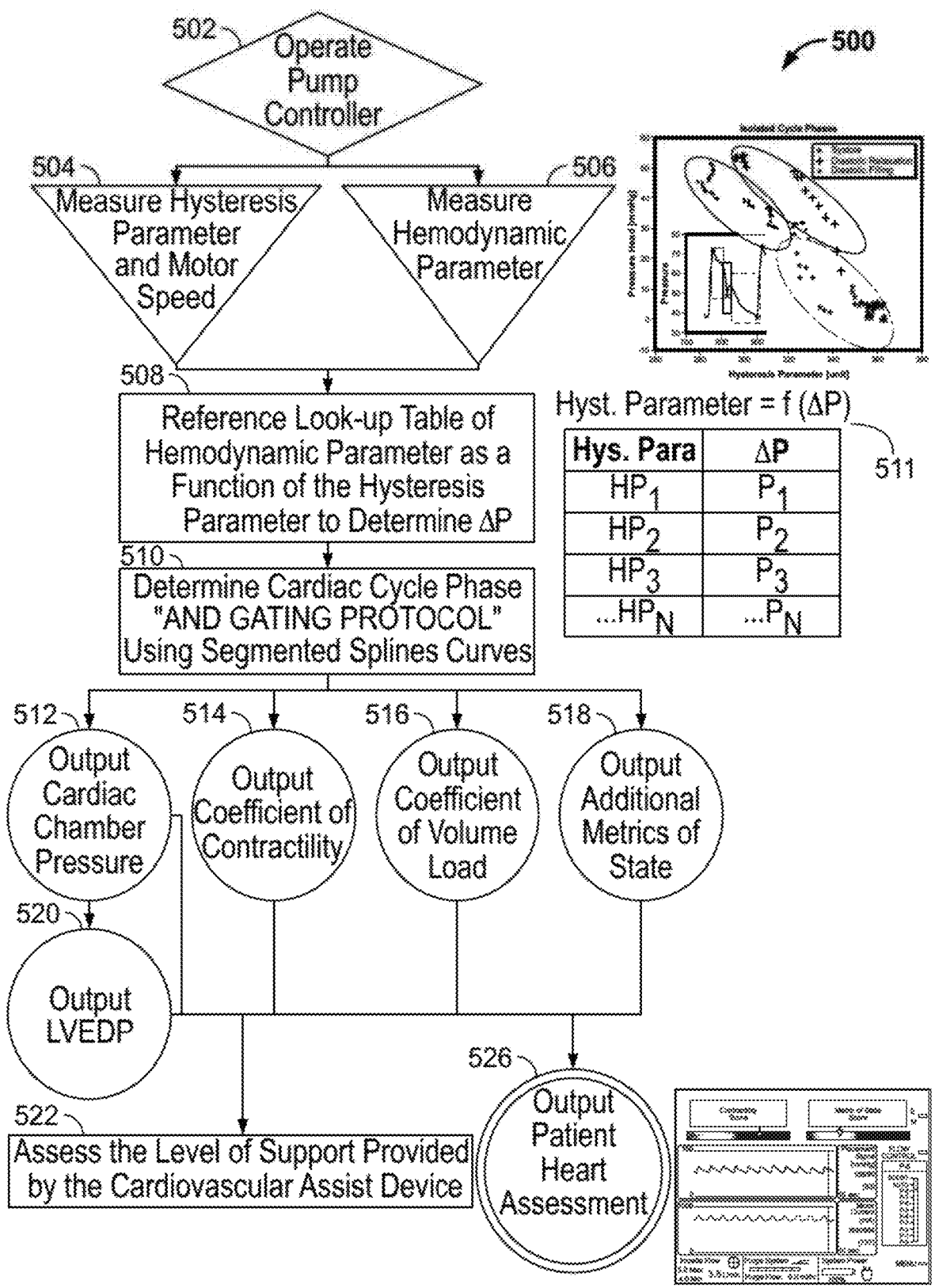
FIG. 5 shows a process for calculating metrics of heart function according to certain implementations.

FIG. 5 shows a process for calculating metrics of heart function and adjusting the level of support provided by a cardiovascular assist device. In step 502, a pump controller is operated. In step 504, a hysteresis parameter and the motor speed is measured. The hysteresis parameter may be a parameter of the heart pump's motor (e.g., motor current or motor power). In step 506, a hemodynamic parameter is measured. For example, in some implementations, the aortic pressure is measured. In step 508, a look-up table of hemodynamic parameters as a function of the hysteresis parameter is consulted or referenced in order to determine the ΔP or differential pressure. An example look-up table 2011 is show having a column "Hys. para" for stored values of the hysteresis parameter and a column "ΔP" for the pressure difference between the ventricle and the aorta. In some implementations, the table may be based on predetermined pressure-current curves. The heart parameter can be determined by mapping the measured current and pressure to heart parameters.

The predetermined pressure-current curves can be measured using a mock circulatory loop, animal data, or clinical data. For example, a mock circulatory loop (MCL) with varying contractile, preload, and afterload conditions may be used to define the bounds of pump performance, while an animal model may be used to delineate biological variability and pathology. Using an MCL for characterization and animal models for validation is an effective means for relating performance of the heart pump to heart function. Although baseline motor current may vary between pumps, each pump can be normalized to generate a normalized current waveform. In some implementations, heart pumps are binned separately in 30 mA ranges based on their current responses to normalize calculations for approximate flow rate.

At step 510, the cardiac cycle phase is determined. This determination of the cardiac cycle phase may be made using segmented spline curves. As will be discussed in relation to FIG. 13, segmented splines delineate the regions of the total hysteresis loop. The hysteresis loop can be segmented into a known number of curve fitting splines. Each spline fit to a curve of the hysteresis loop is indicative of a cardiac cycle phase. For example, in a hysteresis loop fit with three splines, a first spline may indicate a diastolic relaxation phase, a second spline may indicate a diastolic filling, and a third spline may indicate the systole. The meeting point of the second and third spline in this case is the LVEDP. The phase estimation can act as a filter for the pressure and current signals because it can allow pressure and current signals to be compared to pressure and current signals that occurred during corresponding stages of the cardiac cycle. The phase estimation may be based on the pressure information received in step 2006 and may involve locating fiducial points in the pressure information indicative of the heart phase. In some implementations, the dicrotic notch in the pressure signal is detected to indicate the beginning of diastolic filling. The dicrotic notch is a small downward deflection in the arterial pulse or pressure contour immediately following the closure of the semilunar valves. This dicrotic notch can be used as a marker for the end of systole and hence approximately the beginning of diastole.

The heart phase information from step 510 may significantly improve the accuracy of the heart parameter estimation by accounting for the effect of hysteresis in the pressure-current curve. Because the pressure-current curves exhibit hysteresis due to the phases of the heart cycle, to compare pressure and current data points accurately the phase of the heart must be taken into account. Otherwise, pressure and current data collected during systole might be compared with non-analogous reference pressure and current data collected during diastole, for example, which may skew the estimate of the heart parameter.

In step 512, a cardiac chamber pressure is output. In some implementations, the cardiac chamber pressure measured is the pressure of the left ventricle. In certain implementations, the cardiac chamber pressure measured is the pressure of the right ventricle. In step 514, a coefficient of contractility is output. The contractility score provides an indication of cardiac function. More specifically, the contractility score represents the inherent strength and vigor of the heart's contraction during systole. The stroke volume of the heart will be greater if the contractility of the heart is greater. For example, medium contractility may occur when the stroke volume of the heart is about 65 mL. High contractility may occur when the stroke volume of the heart is over 100 mL. Low contractility may occur when the stroke volume of the heart is less than 30 mL. The contractility score may be expressed numerically and/or graphically. The contractility score may be non-dimensional. In step 516, the coefficient of volume load is output. In step 518, additional metrics of state are output.

In step 520, the cardiac chamber pressure determine in step 512 is used to determine left ventricular end diastolic pressure (LVEDP). This calculation may be made by determining the left ventricular pressure from step 512 corresponding to the end of diastole. LVEDP tends to be significantly elevated in almost all cases of acute myocardial infarction, especially with patients in heart failure. This is largely due to a shift in the Frank-Starling relationship because of a change in the end diastolic pressure volume ratio (EDPVR). As patients move closer to heart failure, the Frank-Starling curve shifts downward, such that a given pressure results in a lower stroke volume. Because of this, at a given cardiac output for a patient, the LVEDP can be indicative of the state of the heart given all other conditions remain relatively constant. Measuring these changes in LVEDP can be valuable for monitoring the progression of the patient either towards heart failure or towards recovery thus allowing clinicians to adjust the required therapy accordingly.

In step 522, the level of support provided by the assist device is assessed. In some implementations, this assessment is automatic. In certain implementations, this assessment is at least partially performed by a healthcare professional. In some implementations, additional information regarding the hemodynamic parameters and the level of support are provided to allow a clinician to adjust the level of support to optimize patient outcomes. In some implementations, the level of support provided by the cardiovascular assist device is titrated by changing the power delivered to the motor, changing the motor speed, and/or changing the flow rate, or any other suitable change that results in a change to the level of support by the cardiovascular assist device. In step 526, a patient heart assessment is output. This patient heart assessment may be shown on a user interface, such as user interface 2000 of FIG. 20A or 2001 of FIG. 20B. In some implementations, the assessment is a report that may be sent to a healthcare professional. In some implementations, a recommendation for a level of support to be provided to the patient heart is output. In some implementations, the assessment is a report that may be sent to a healthcare professional. The recommendation of a level of support may be optimized to provide hemodynamic support. The recommendation of a level of support may be based on internal algorithms or tables. The recommendation of a level of support may include directions to attain the recommended level of support, including changing the volume flow delivery provided by the pump, changing the level (magnitude and/or frequency) of automated pulsation based on quick speed changes, and/or changing the level of pump speed (e.g., rotational speed of the motor or rotational speed of the rotor) in short or long bursts to provide augmented flow. In some implementations, the process 500 of FIG. 5 may be repeated automatically such that the process 500 provides closed loop control for the cardiac assist device. By titrating therapy to the patient's degree of need, the recovery of the heart can be promoted. If the assessment in step 526 indicates that the heart has sufficiently recovered, the therapy may be terminated or a healthcare professional may be prompted to consider terminating therapy.

Figure 6:
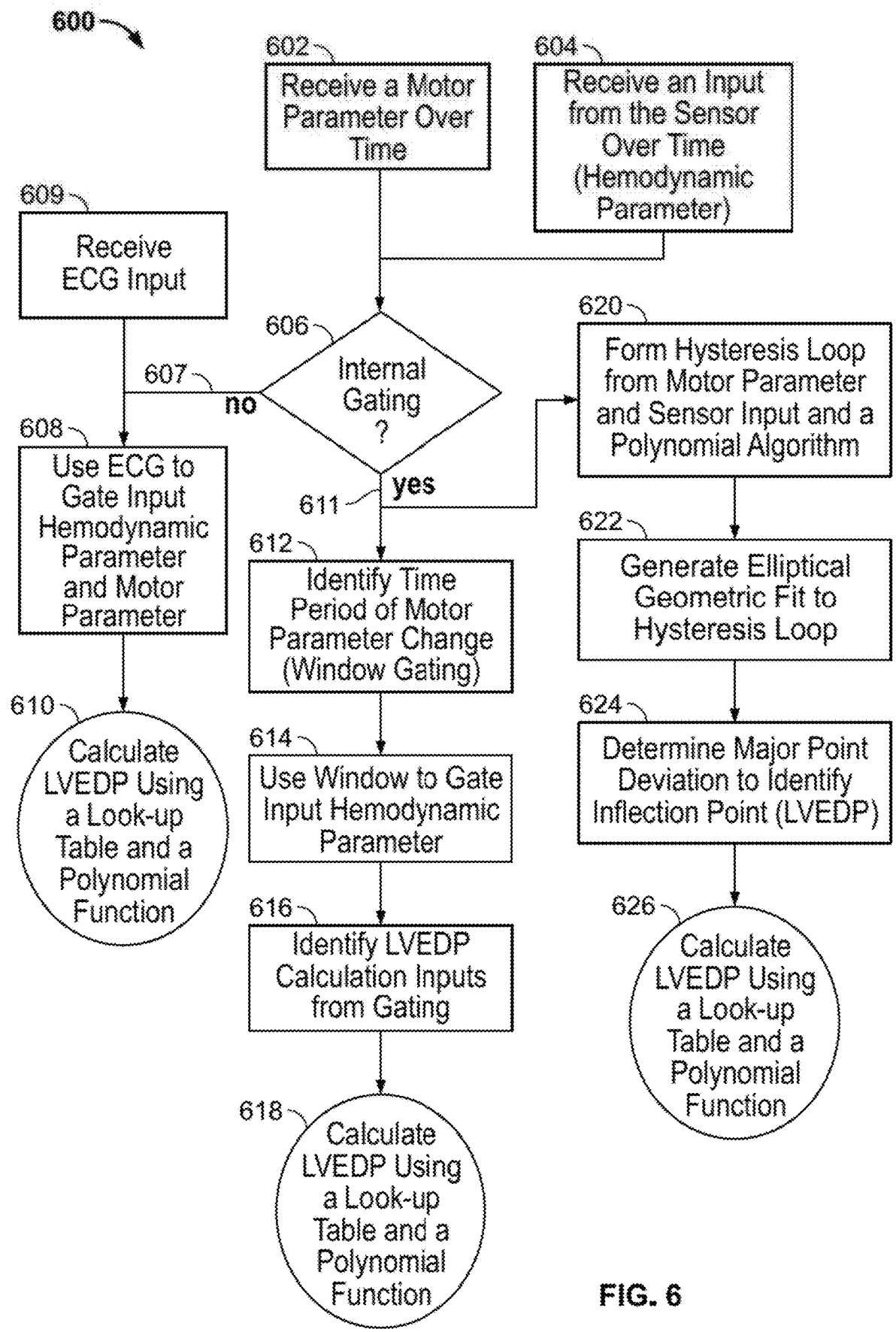
FIG. 6 shows a process of determining LVEDP from a measured motor parameter signal and a sensor signal using various gating processes, according to certain implementations.

FIG. 6 shows a process 600 of determining LVEDP from a measured motor parameter signal and a sensor signal. The LVEDP can be calculated according to one of several procedures. At step 602 a motor parameter is received over a period of time. As described herein, the measurement of a motor parameter can include motor current, power, speed of the motor, or torque. At step 604, an input signal from the sensor is received over a period of time. The signal from the sensor may be any hemodynamic parameter, such as an aortic pressure. At step 606, a decision is made as to whether to use an internal gating method.

If the decision is no, the process 600 follows path 607 to step 608 at which received ECG input 609 is used to gate the input hemodynamic parameter and motor parameter. The ECG input from step 609 is analyzed and a time period of the ECG data is identified in which the presence of an inflection point that indicates an end cycle of diastole, or an R-peak in the QRS waveform, indicates that the LVEDP will be found in the time period. The hemodynamic parameter measured in the corresponding time period is then analyzed to find the point corresponding to the LVEDP. At step 610, the LVEDP is calculated from the identified point using a look-up table and the relationship between the hemodynamic parameter and the motor parameter is characterized by determining a polynomial function fit to the hemodynamic parameter and motor parameter.

If the decision at step 606 is that internal gating will be used, the process 600 follows path 611 to either step 612 or step 620 based on the desired information from the data. Either pathway may be used to determine the LVEDP, but additional cardiac parameters can also be determined from the pathway beginning from step 620.

At step 612, a time period of the motor parameter is identified in which there is a change in the motor parameter. This time period is considered a gating window, and the change in the motor parameter is indicative of the change in heart phase associated with LVEDP. In some implementations, the change in the motor parameter may be a decrease in motor speed due to a change in load, an increase in motor current due to the change in load, or any other characteristic change in a motor parameter as a result of cardiac changes. At step 614 the identified time period, or gating window is used to identify the corresponding time period of the hemodynamic parameter in which the LVEDP is found. At step 616, the LVEDP calculation inputs are identified in the hemodynamic parameter by analyzing the hemodynamic parameter data in the identified time period and identifying a change in the hemodynamic parameter. At step 618, the LVEDP is calculated using a look-up table and a polynomial function.

At step 620, a hysteresis loop is formed from the motor parameter and sensor input and a polynomial algorithm which enables missing data points to be approximated. The data collected from the motor parameter and sensor input describe the phases of the heart in a hysteresis loop. For example, if the motor parameter is a motor current and the sensor input is an aortic pressure, the polynomial algorithm allows the pressure head to be determined from the measured motor current and aortic pressure, such that a hysteresis loop can be created from the measure motor current and the calculated pressure head. At step 622, an elliptical geometric fit to the hysteresis loop is generated, for example using Euler's equation to fit the hysteresis loop to an ellipse. At step 624, the data forming the hysteresis loop is analyzed with regard to the elliptical fit to determine major point deviation indicative of an inflection point observed at the LVEDP value. At step 626, the LVEDP point is calculated from the determined inflection point using a look-up table and a polynomial function. For example, the inflection point may be determined by analysis of the hysteresis loop formed from motor current and pressure head, and the LVEDP can be calculated from the pressure head data at the inflection point. The LVEDP can then be output to a user, and additional heart metrics may be determined to aid in the understanding of the patient's cardiac function.

Figure 7:
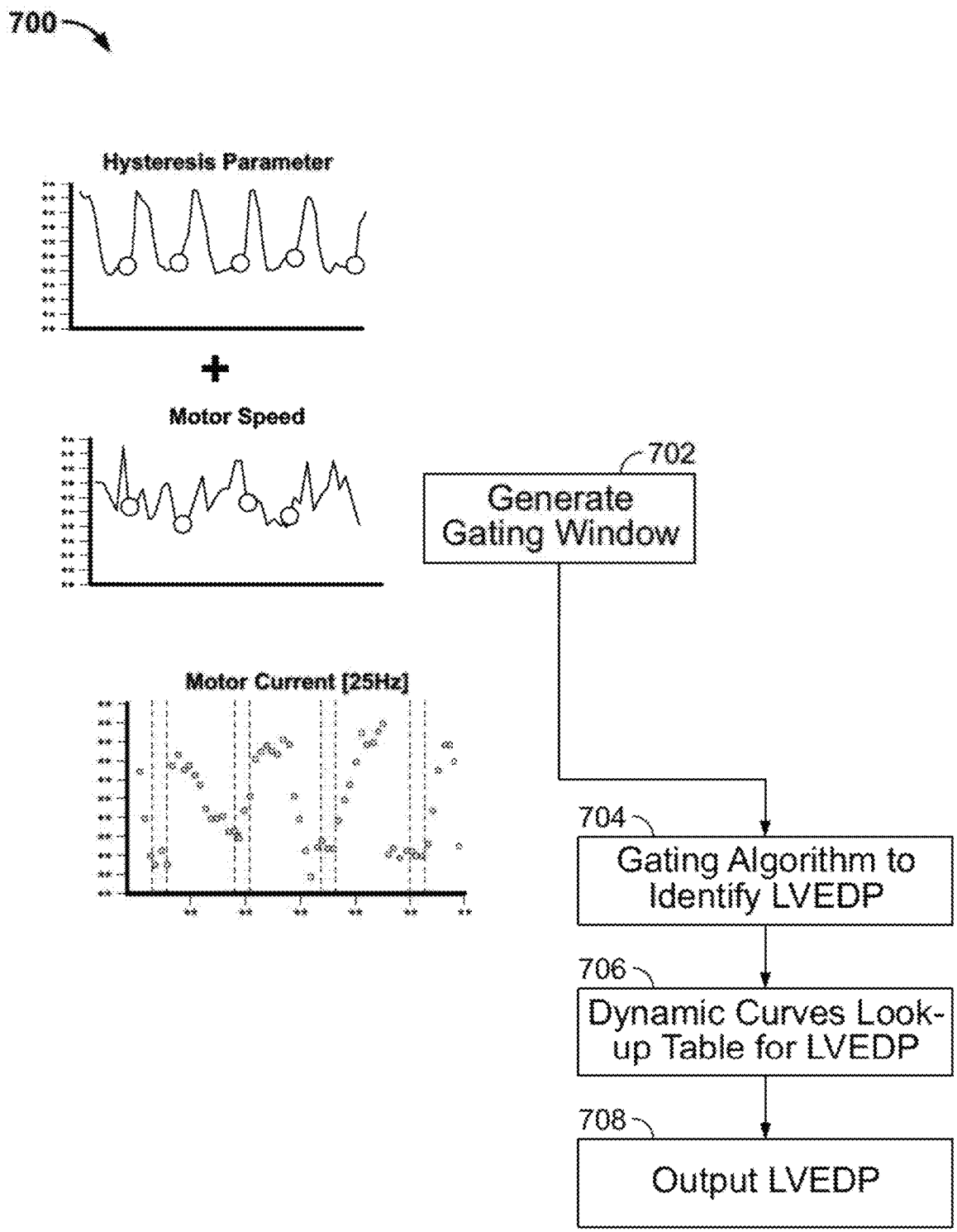
FIG. 7 shows a process of applying a gating algorithm to determine the LVEDP.

Gating algorithms as described above are applied to hemodynamic parameter data and pump or motor parameters in order to determine the LVEDP, cardiac cycle phase, and other parameters. In each of the above pathways to the calculation of LVEDP, whether gating is internal or external, hemodynamic parameter data points identified using the gating technique can be used with a look-up table, to look up the dynamic LVEDP curve, and an LVEDP value may be outputted which may be used in the determination of other cardiac metrics. FIG. 7 shows a process for applying a gating algorithm to determine LVEDP. The depicted process shows in greater detail the determination of the gating window and application of the gating algorithm to determine LVEDP, as described with regard to FIG. 6. Gating is used to determine or isolate the cardiac phases and/or left ventricular pressure (such as LVEDP). The gating can be completed by examining the device parameter and physiological parameters to locate local minima or maxima.

The controller measures a hysteresis parameter associated with the cardiac cycles and measures a device or motor parameter. The hysteresis parameter may be any cardiac hysteresis parameter discussed herein, and the device parameter may be any device parameter which varies with time and pulse. At step 702, the controller uses the input hysteresis parameter and device parameter to generate a gating window. The gating algorithm includes a method of means and standard deviations to identify the data points which are relevant local minima by gating the data. The local minima for the device parameter and the physiological parameter are determined independently, and the corresponding local minima data points are returned by the algorithm.

At step 704, the gating algorithm is applied to identify the LVEDP. The controller inputs the local minima data points of the device parameter and the physiological parameter into a function which describes the relationship between the hysteresis device parameter (for example, motor current) and the physiological parameter (for example, aortic pressure). The function is used to determine a point of the data associated with the LVEDP.

At step 706, the calculated LVEDP point is used in a dynamic curve look-up table to determine the LVEDP, and at step 708 the LVEDP is output from the system. The dynamic curve look-up table may translate the aortic pressure measurement at a certain cardiac cycle to a differential pressure in order to find the LVEDP value. Although FIG. 7 shows LVEDP as the output of the gating algorithm, the gating algorithm may be used with any metric calculation as described herein.

Figure 8:
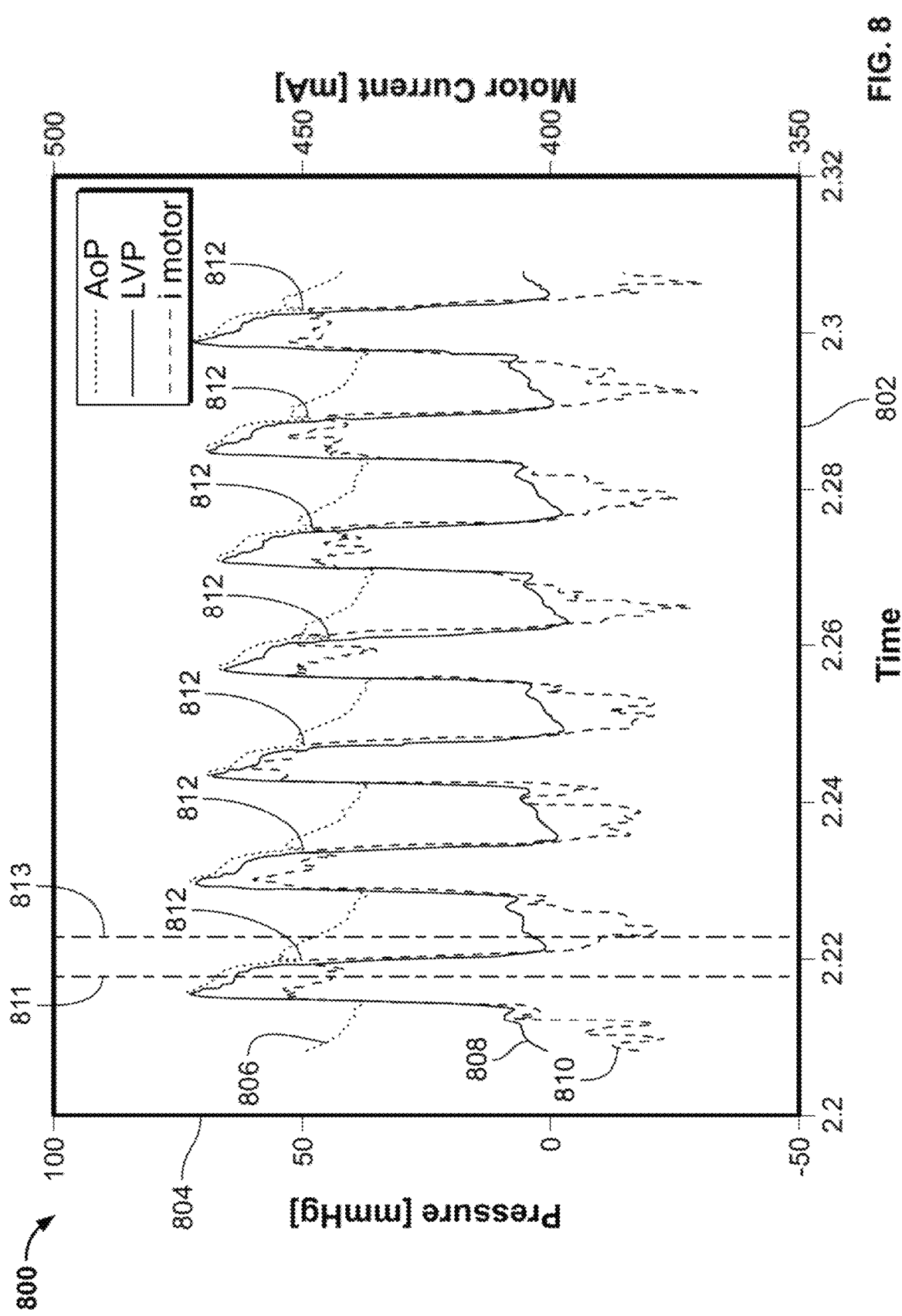
FIG. 8 shows a plot of aortic pressure, left ventricular pressure, and motor current over time.

FIG. 8 shows a plot 800 of aortic pressure, left ventricular pressure, and motor current over time. The data from the plot of FIG. 8 can be used to generate pressure-current curves for estimation of a heart parameter (e.g., left ventricular pressure) from pressure and current. The plot 800 has an x-axis 802 in units of time and a y-axis 804 in units of either pressure in mmHg or motor current in mA. The plot 800 also includes an aortic pressure signal 806, a left ventricular pressure signal 808, and a motor current signal 810. The aortic pressure signal 806 can be measured by the pressure sensor 312 of FIG. 3, the pressure sensor 112 of FIG. 1, or any other suitable pressure sensor. The aortic pressure signal includes dicrotic notches 812 which can be used to mark the beginning of diastolic filling. The motor current signal 810 can be generated from the current sensor 314 of FIG. 3 or any other suitable current sensor. The left ventricular pressure signal 808 can be generated using a dedicated catheter placed in the left ventricle, a pressure sensor mounted on the inlet side of the pump, or an estimation based on the pressure-current. The signals 806, 808, and 810 in plot 800 can be generated from data collected in an animal model or in a human patient. The signals 806, 808, and 810 in the plot 800 were generated from data collected in a pig heart while the pump motor was operating at 33,000 rpm.

As shown in the plot 800, the motor current signal 810 varies with the cardiac phase. The load on the pump, and hence the motor current signal 810, increases as the blood flow rate through the heart increases. The motor current signal 810 increases at the same time as the left ventricular pressure signal 808 and the aortic pressure signal 806 increases. This may seem counterintuitive since the pressure difference across the aortic valve is decreasing, but in this pump configuration, the prime determinant of the increasing current is increasing load on the motor due to a higher mass flow rate. Higher mass flow rates occur during systole, which leads to higher motor current during systole. This increase in motor current is not apparent in the Bernoulli relation as conventionally expressed since the Bernoulli relation is often mass or rate normalized for describing a steady ohmic system. Unlike typical pumping environments, the heart generates a phasic and dynamic load via a variable mass flow to which the heart pump (e.g., heat pump 302) responds. This causes phasic components in the motor current signal that dominates effects from changes in the pressure described by Bernoulli. As a result, the motor current waveform is representative of the cardiac cycle dynamics and can be used to extract cardiac energetics. Although the motor driver may use a control algorithm that adjusts motor current immediately after a change in the heart phase, the effect of such a control algorithm on motor current can be predicted so that variations in motor current can still be used as indicators of variations in the heart's contractile ability and stroke volume.

The motor current signal 810 can be used to extract the LVEDP from the left ventricular pressure signal 808. Using an algorithm, the motor current signal 810 is analyzed to determine the time period in which the motor current signal 810 changes. For example, the motor current signal 810 falls precipitously between first time 811 and second time 813. The left ventricular pressure signal 808 can be analyzed at the corresponding time period in order to accurately extract the LVEDP. By gating the left ventricular pressure signal 808 based on the motor current signal 810, the amount of data which needs to be analyzed to find the LVEDP is cut down and noise is diminished. This gating technique utilizing a change in the motor parameter can be used with a variety of motor parameters. For example, an increase in the motor current indicating an increased load can indicate a time period in which the LVEDP may be identified. Additionally, a decrease in the motor speed in response to an increased load can also indicate the time period in which the LVEDP may be identified.

Figure 9:
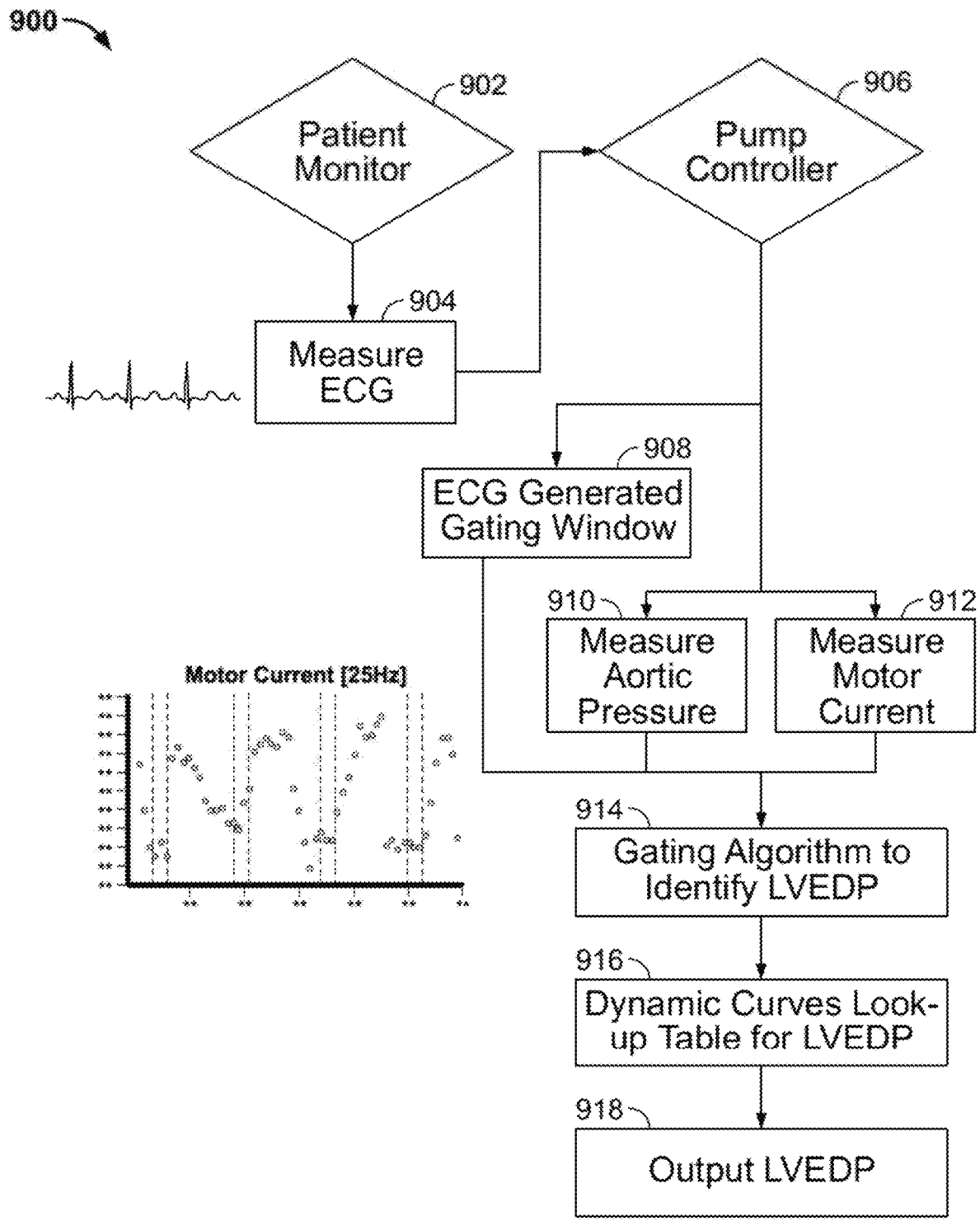
FIG. 9 shows a process of applying a gating algorithm based on ECG data to determine the LVEDP.

FIG. 9 shows a process 900 for applying an ECG-based gating algorithm to determine LVEDP. The depicted process shows in greater detail the determination of the gating window using ECG data and application of the gating algorithm to determine LVEDP, as described with regard to FIG. 6.

Process 900 begins with a patient monitor 902 which measures and records ECG data at step 904. The patient monitoring system 902 may be external to the pump system or may be integrated within the pump system. The measured ECG data is transmitted to pump controller 906, where the ECG data can be used ECG data to determine a gating window for identifying LVEDP. At step 908, the pump controller generates an ECG-based gating window by identifying the segment of ECG data in which the R-peak of the QRS waveform, or end cycle of the diastole is located. This may be accomplished by fitting the data to a periodic equation and determining data points that deviate from the equation, or by identifying points in the data which correspond to the R-peak. The gated window is a time period in which the R-peak or end cycle of the diastole is found in the ECG data, though the time period does not need to be expressed in absolute time.

At step 910, the pump controller measures the aortic pressure and at step 912, the pump controller measures the motor current. The ECG gating window identified at step 908, and the measured aortic pressure and motor current are used by the pump controller at step 914 to identify an LVEDP from the aortic pressure data. The controller analyzes the aortic pressure data points in the segment of the aortic pressure data that corresponds to the ECG gating window to determine the aortic pressure value at which the LVEDP is expressed. By gating the data, the LVEDP point may be more quickly determined and less data needs to be analyzed, decreasing the amount of processing time required.

At step 916, the pump controller accesses a dynamic curves look-up table to convert the determined aortic pressure point to an actual LVEDP. The actual LVEDP can be output from the gating algorithm for use by health care professionals. For example, health care professionals may make adjustments to the pump speed by increasing or decreasing the pump speed based on the reported LVEDP value.

In some implementations, cardiac cycle phase estimation is also determined entirely or partially based on ECG data. Such ECG data may be timed with the pressure tracings. The characteristic in the ECG used to estimate the heart phase may be the beginning of the QRS complex and the end of the T-wave. If there is noise in the ECG signal, it may be more reliable to detect the peak of the QRS complex (e.g., the R-wave) and the peak of the T-wave. In phase estimation methods using either pressure signals or ECG signals, an offset from the detected feature may be used to more accurately identify filling phases since actual filling occurs slightly before or after these identified landmarks. The R-peak of the QRS waveform may also be used to identify a period in which a particular cardiac parameter can be identified, such as the LVEDP, as the R-peak corresponds to the end cycle of the diastole. A combination of both pressure signal-based and ECG-based methods can allow more reliable identification. The weighting between the two methods can be optimized using datasets having known filling time parameters, known left ventricular pressures, and high signal to noise ratios. In some implementations, the phase estimation from a cardiac hysteresis loop corresponds to one of cardiac ejection, diastolic filling, and diastolic relaxation.

Figure 10:
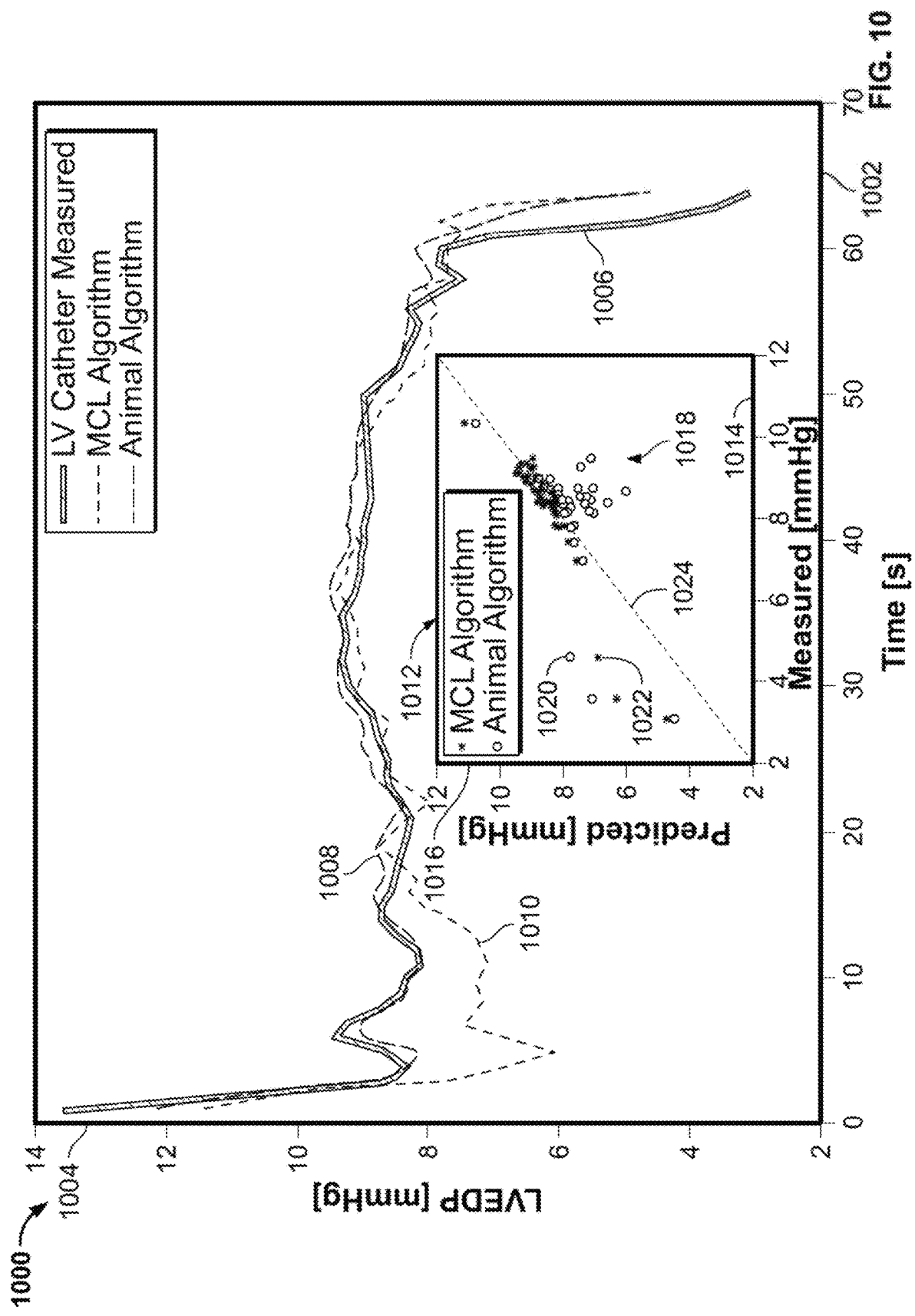
FIG. 10 shows a plot of LVEDP as measured and as calculated by algorithms over time.

FIG. 10 shows a plot 1000 of LVEDP as measured and as predicted by MCL and animal models over time. The plot 1000 has an x-axis 1002 showing time in units of seconds and a y-axis showing LVEDP in units of mmHg. The plot 1000 includes a first waveform 406, a second waveform 1008, and a third waveform 1010. The first waveform 1006 represents the LVEDP over time as measured by a catheter in the left ventricle. The second waveform 1008 represents the LVEDP over time as predicted by an algorithm developed to characterize performance of a pump in a mock circulatory loop (MCL). The third waveform 1010 represents the LVEDP over time as predicted by an algorithm developed to characterize performance of a pump in a porcine animal model. The inset plot 1012 shows the correlation of the LVEDP as measured in the left ventricle and as predicted by the MCL and animal models for each measurement. The inset plot 1012 has an x-axis 1014 showing the measured LVEDP in units of mmHg and a y-axis 1016 showing the predicted LVEDP in units of mmHg. The inset plot 1012 also includes a plurality of data points 1018 representing measured-predicted pairs. The data points 1018 in plot 1012 include unfilled points (for example 1020) representing pairs including LVEDP as predicted by an animal-based algorithm, and star-shaped points (for example 1022) representing pairs including LVEDP as predicted by a MCL-based algorithm. The correlation line 1024 is provided to guide the eye and represents a 1 to 1 correlation, that is, predicted LVEDP equal to measured LVEDP.

Pump characterization was performed in both a MCL and in a porcine animal model undergoing interventions to simulate disease. LVEDP was successfully tracked during IVC occlusion in the animal and MCL models. The RMS error for the animal model was 0.90 mmHG. The RMS error for the MCL model was 0.35 mmHG. This suggests that the pump characterization using a MCL may be superior due to the presence of unidirectional variance versus bidirectional variance. Thus, using an MCL for characterization and animal models for validation can be an effective means for relating performance of the heart pump to heart function. Data from MCL models and animal models may be used to develop predictive algorithms and to develop predetermined pressure-current curves.

Figure 11:
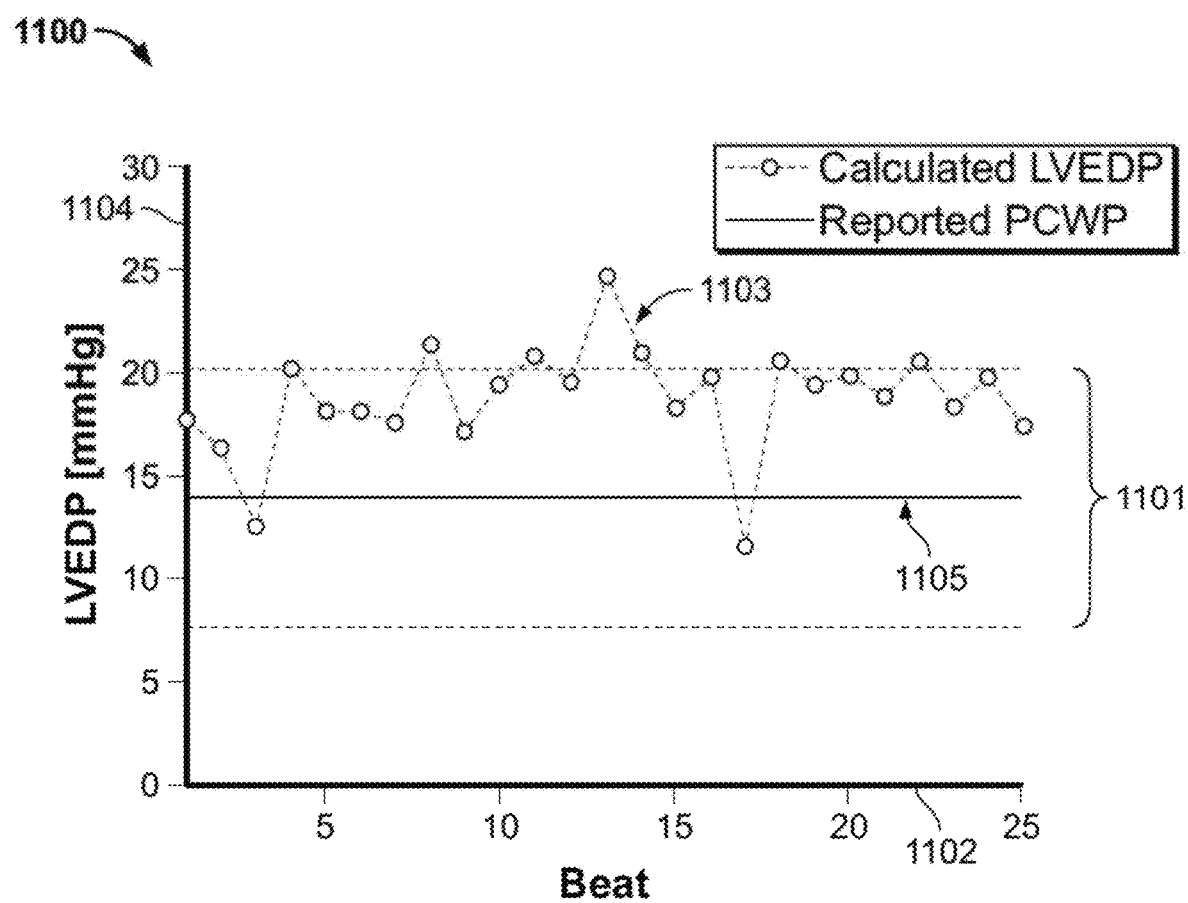
FIG. 11 shows a plot of the LVEDP calculated from patient data illustrating the accuracy of the determined LVEDP using a gating method.

FIG. 11 shows a plot of the LVEDP calculated from patient data illustrating the accuracy of the determined LVEDP using the gating method. The plot 1100 includes an x-axis 1102 representing a number of beats of the heart and a y-axis 1104 representing the calculated LVEDP based on the motor and physiological parameters. The plot 1100 includes a scatter plot 1103 of the calculated LVEDP at each beat of the heart, a line 1102 showing the reported pulmonary capillary wedge pressure (PCWP), and standard error lines 1101 for the reported PCWP line 1102.

The plot 1100 shows the PCWP 1102 actually recorded in a patient as well as the LVEDP 1103 calculated by retrospectively applying the algorithms to the patient data. The plot 1100 shows that the calculated LVEDP 1103 is within the standard error lines 1101 for the reported PWCP line 1102. The PWCP is traditionally measured by wedging a pulmonary catheter and balloon into an arterial branch of the pulmonary artery. The calculated LVEDP 1103 is closest to the reported PWCP 1102 at the data points taken at expiration of the patient, which is the same point at which the wedge pressure is taken in a patient. The calculated LVEDP 1103 as shown in FIG. 11 is comparable or better than the industry standard PWCP 1102 when applied to patient data.

Figure 12:
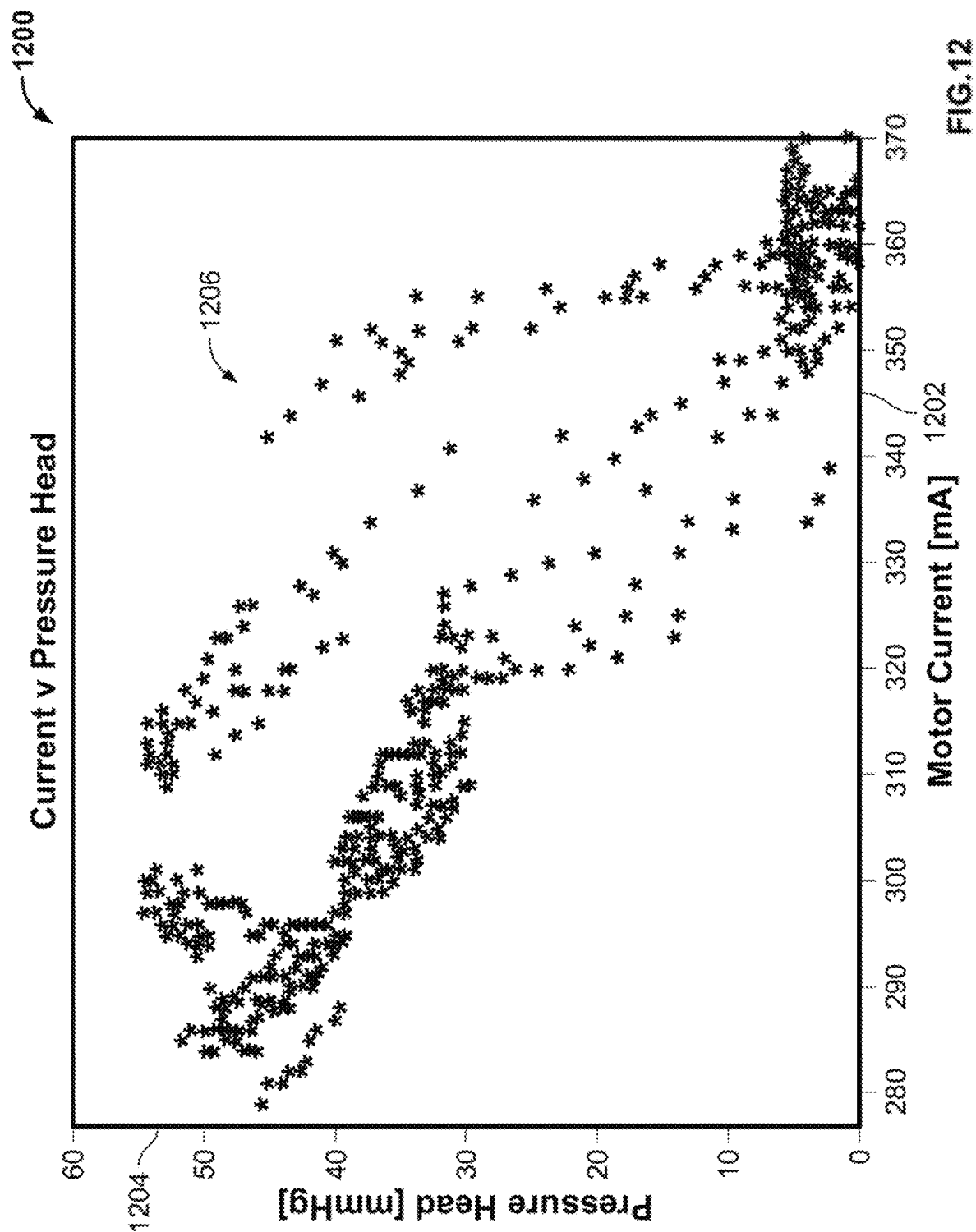
FIG. 12 shows a plot of pressure head as a function of motor current based on data from a porcine animal model.

FIG. 12 shows a scatter plot 1200 of pressure head as a function of motor current. The plot 1200 demonstrates the effect of hysteresis on the pressure-current curve. The plot 1200 has an x-axis 1202 showing current in units of mA and a y-axis 1204 showing pressure head between the left ventricle and the aorta in units of mmHg. The plot 1200 also includes a plurality of data points 1206 representing current-pressure pairs gathered from a porcine animal model. The data points in plot 1200 were generated while the motor was operating at 30,000 rpm. The data points 1206 roughly form a hysteresis loop. The shape of the scatter plot 1200 shows that the relationship between current and pressure head between the left ventricle and the aorta varies throughout the cardiac cycle. Because of the hysteresis in the pressure-current curve, a method to gate measurements based on cardiac phase can help improve accuracy of estimates of heart parameters by ensuring that sample data points are compared with reference data points that occurred in the same heart phase (e.g., systole or diastole).

Figure 13:
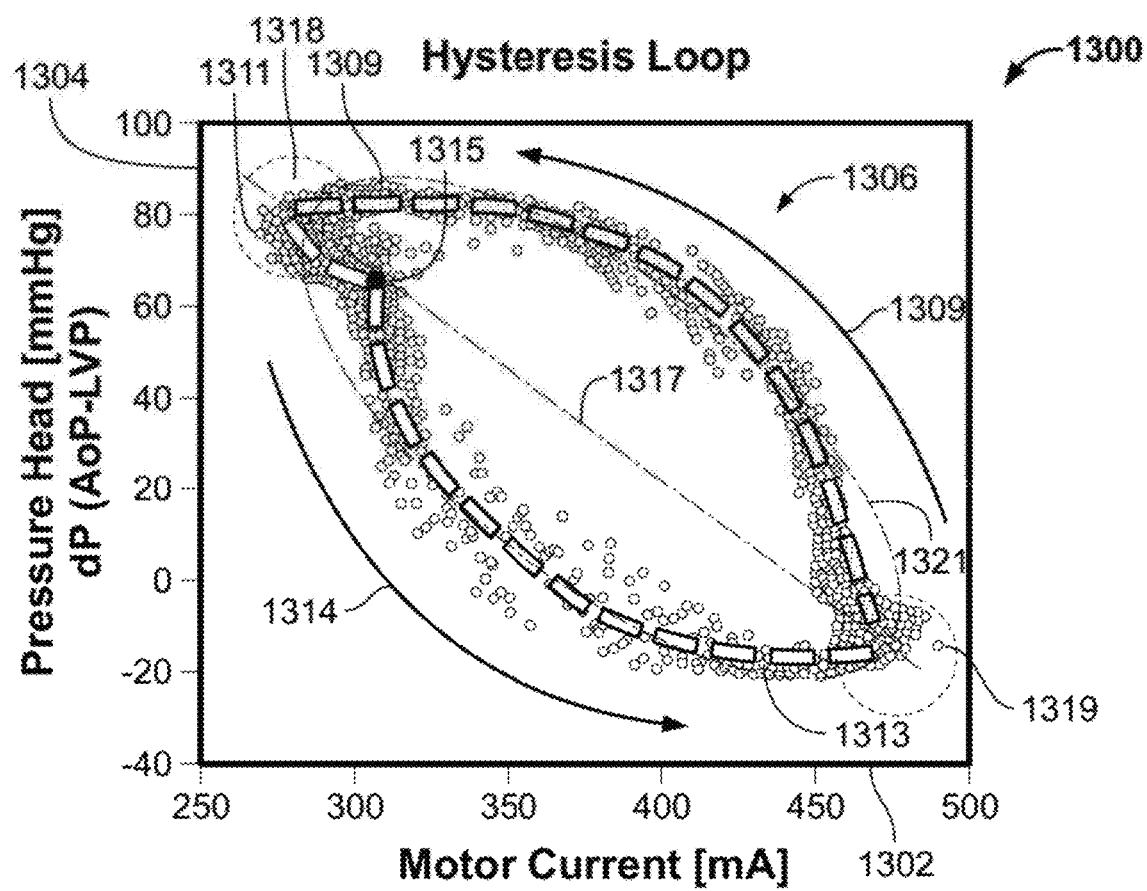
FIG. 13 shows a plot of pressure head as a function of motor current from a porcine animal model with spline curves fit to the regions of the hysteresis loop.

FIG. 13 shows a scatter plot 1300 of pressure head as a function of motor current. The plot 1300 has an x-axis 1302 showing current in units of mA and a y-axis 1304 showing pressure head between the left ventricle and the aorta in units of mmHg. The plot 1300 also includes a plurality of data points 1306 representing current-pressure pairs. The data points 1306 form a hysteresis loop and include segmented spline curves fit to the hysteresis loop showing the determination of the phases of the cardiac cycle. The hysteresis loop is segmented into three curve fitting splines, 1309, 1311 and 1313. Each of the splines is representative of a cardiac cycle phase. The first spline 1309 is indicative of a section of the hysteresis loop recorded during diastolic relaxation (isovolumetric relaxation). The second spline 1311 is indicative of a section of the hysteresis loop recorded during diastolic filling. The third spline 1313 is indicative of a section of the hysteresis loop recorded during systole (ventricular contraction). The point at which the second spline 1311 and the third spline 1313 meet is the LVEDP 1315. The characteristic notch observed at the meeting of the second spline 1311 and the third spline 1313 enables the identification of the LVEDP 1315 point. The arrows 1307 and 1314 show the direction in which the cardiac cycles progress.

A characteristic notch can be observed at the time point at which LVEDP occurs in the hysteresis loop, allowing for visual recognition of the point in the cardiac cycle, as well as algorithmic identification of the LVEDP as an inflection point in the pressure head and motor current hysteresis loop. At the LVEDP inflection point, the motor current changes as the left ventricle goes from undergoing diastolic filling to actively contracting. Determination of the LVEDP inflection point from the hysteresis loop is dependent on the sampling rate for collection of motor and pressure parameters, and the calculation must take into account sampling rate or extrapolate the data to accurately determine the LVEDP inflection point. The phase estimation can act as a filter for the pressure and current signals because it can allow pressure and current signals to be compared to pressure and current signals that occurred during corresponding stages of the cardiac cycle.

The LVEDP 1315 point can also be calculated from the plot 1300 using best fit algorithms. The LVEDP 1315 point can be calculated from the hysteresis loop using polynomial equations and a best fit algorithm describing the hysteresis data as an ellipse. The hysteresis loop can be estimated using an equation based on Euler's equation for steady fluid motion. The coefficients of the equation are calculated using multiple regression analysis from the equation:

$$H = A*i + B*\frac{di}{dt} + C\omega^2 + D*\frac{d^2i}{d^2t}$$

where the coefficients are A, B, C, and D, i is the motor current, di/dt is a derivative of the motor current in time, $\omega$ is the thermodynamic work, and $d^2i/d^2t$ is a second derivative of the motor current in time. The final term in the equation is optional, as this term is very small. The final calculated equation describes the hysteresis loop and can be used to track changes in size and shape of the loop over time, or changes in curvature or local slope over time, as well as used to extract metrics of heart function including the LVEDP.

According to the equation, an ellipse 1321 is fit to the hysteresis loop using geometric methods, and the LVEDP 1315 point can be detected based on the relationship of the data points to the described ellipse. The distance between each point and foci on the ellipse 1321 can be used to determine outlier data points from the elliptical fit according to the equation:

$$r_1 + r_2 = 2a$$

where r values are a distance from a point on the ellipse 1321 to each foci and a is the length of the short axis of the ellipse 1321. The values of data points which are outside of the ellipse 1321 are evaluated for the location, and the most clustered location of data points is determined by iterating through the data. A cluster can be defined in a variety of ways, for example a cluster can be defined as at least 3 points which are within 2 mA and 1.5 mmHg of each other.

A bisecting line 1317 can be drawn through the ellipse 1321 describing the hysteresis loop by algorithmically determining the clusters of the data points 1306 forming the two ends of the hysteresis loop. Because the heart spends the largest amount of time in these two phases and only travels transiently between them, the majority of the measured data points 1306 are in these two locations. A first cluster 1318 corresponding to peak relaxation and a second cluster 1319 corresponding to peak ejection are detected and a line 1317 is drawn between the means of the two clusters 1318 and 1319. The line 1317 generally divides the ellipse 1321 and the hysteresis data in half, into a top section including the first spline 1309 (diastolic relaxation) and corresponding generally higher pressure, and a bottom half generally corresponding to a higher pressure. The bottom section of the ellipse 1321 below the line 1317 includes the second spline 1311 (diastolic filling) and the third spline 1313 (systole or ventricular contraction). The LVEDP 1315 point can be estimated from the elliptical fit of the data below the line 1317 and determining the point which has the highest deviation from the circle or ellipse 1321 fitted to the data. Additionally, other heart metrics can be extracted from the data by segmenting the ellipse according to the cardiac phases and each segment can be numerically integrated with a Riemann sum. Alternatively, the hysteresis loop can also be estimated using any other appropriate best fit algorithm.

Left ventricular diastolic pressure and left ventricular end diastolic pressure (LVEDP) can be used to determine the overall state of the heart function. LVEDP is the pressure in the left ventricle at the end of ventricular filling and immediately before ventricular contraction. LVEDP tends to be significantly elevated in almost all cases of acute myocardial infarction, especially with patients in heart failure. This is largely due to a shift in the Frank-Starling relationship which describes the relationship between the contractile state of the heart and the LVEDP because of a change in the end diastolic pressure volume ratio (EDPVR). As patients move closer to heart failure, the Frank-Starling curve shifts downward, such that a given pressure results in a lower stroke volume. Because of this shift, at a given cardiac output for a patient, the LVEDP can be indicative of the state of the heart given all other conditions remain relatively constant. Measuring these changes in LVEDP can be valuable for monitoring the progression of the patient either towards heart failure or towards recovery, thus allowing clinicians to adjust the required therapy accordingly.

After the LVEDP point has been determined based on the elliptical fit, the actual LVEDP can be determined by accessing a look-up table. Predetermined pressure-current curves may be embodied in a look-up table that accepts as its inputs pressure, motor current, and heart phase. The heart phase information may be binary (e.g., diastole or systole) or more fine-grained (e.g., systole, diastolic relaxation, and diastolic filling). The output of the look-up table can be other parameters besides LVEDP, such as contractility, stroke volume, ejection fraction, chamber pressure, stroke work, cardiac output, cardiac power output, left ventricular end diastolic pressure (LVEDP), preload state, afterload state, heart rate, heart recovery, flow load state, variable volume load state, cardiac cycle volume load state, and/or cardiac cycle flow state or any other suitable heart parameter, though the calculation of these parameters may require additional inputs.

While FIG. 13 shows a hysteresis curve formed from the data points 1306 and a bisecting line 1317, this is to illustrate the principles of the algorithm applied to the data. It is not necessary to actually create or depict the hysteresis loop in order to extract the LVEDP data. The controller can extract the LVEDP data by accessing and manipulating arrays of stored data stored in the memory. The controller can store the measured data in the memory and can characterize a relationship between the measured aortic pressure and motor parameter, for example, by fitting the data with an equation that describes one parameter in relation to the other such as an elliptical fit, Euler's equation, or a polynomial expression. The equation that characterizes the relationship between the data points is then used to extract information about the LVEDP point, and in some implementations may also be used to extract information about additional cardiac parameters related to heart function.

Further, it is not necessary to record or measure motor and hemodynamic parameters for an entire cardiac cycle in order to extract the LVEDP data. Enough data points at the transition from the diastolic filling stage to the ventricular contraction phase of the cardiac cycle must be collected that the points can be fit to a portion of an elliptical curve and the LVEDP point which deviates from the elliptical fit can be determined. Alternatively, one or more cardiac cycles can be recorded in order to accurately capture this portion of the curve.

In some implementations, it may be beneficial to display the hysteresis loop formed by relating the measured motor parameter and hemodynamic parameter to each other. The shape and size of the hysteresis loop, or the changes in local slope or curvature, may provide important details about the heart function of a patient. These can be used, for example, by a health care professional to make decisions related to patient care, such as whether to increase or decrease pump support by altering the speed of the pump.

Figure 14:
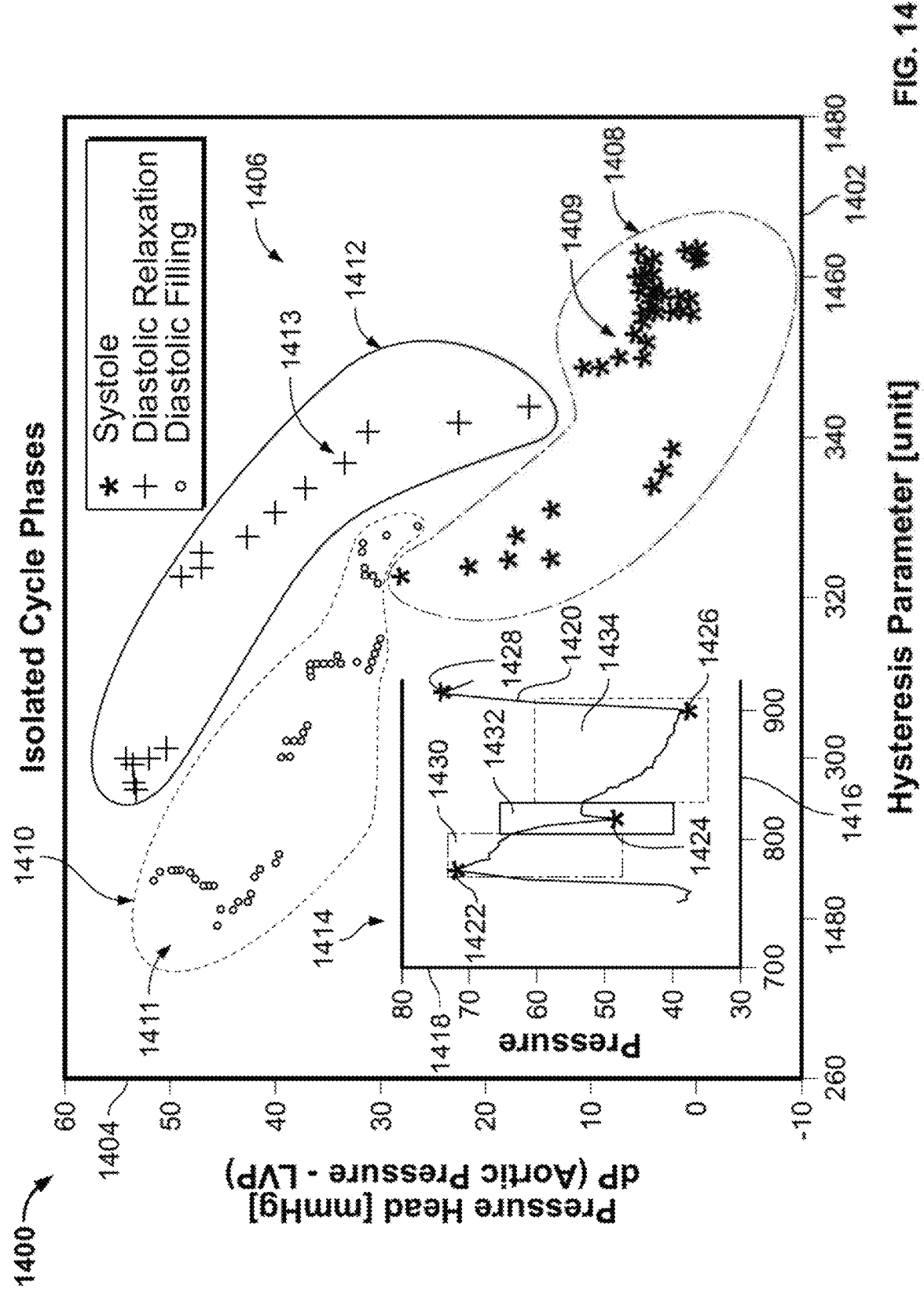
FIG. 14 shows a plot of pressure head as a function of a hysteresis parameter after a hysteresis gate has been applied to segment the data gathered from a porcine animal model.

FIG. 14 shows a scatter plot 1400 of pressure head as a function of a hysteresis parameter after a hysteresis gate has been applied to segment the data. The plot 1400 has an x-axis 1402 which represents a hysteresis parameter and a y-axis 1404 that represents a pressure difference between the left ventricle and the aorta in units of mmHg. The data in the plot 14 was gathered from a porcine animal model. The hysteresis parameter may be a motor parameter such as motor current expressed in mA. The hysteresis parameter may be a non-dimensional or normalized parameter. The plot 1400 includes data points 1406 which have been segments into three groups: a systole region 1408, a diastolic filling region 1410, and a diastolic relaxation region 1412. The region 1408 corresponds to systole and includes data points 1409 that occurred during systole. The region 1410 corresponds to diastolic filling and includes data points 1411 that occurred during diastolic filling. The region 1412 corresponds to diastolic relaxation and includes data points 1413 that occurred during diastolic relaxation. The data points 1406 may be grouped into the systole region 1408, the diastolic filling region 1410, and the diastolic relaxation region 1412 using a heart phase estimator such as the heart phase estimator 318 of FIG. 3.

The plot 1400 also includes a subplot 1414 which has an x-axis 1416 representing time and a y-axis 1418 representing aortic pressure. The subplot 1414 shows an aortic pressure signal 1420 having various fiducial points 1422, 1424, 1426, and 1428 identified. The fiducial points 1422, 1424, and 1426, and 1428 can be used to segment the aortic pressure signal 1420 into phases of the cardiac cycle as indicated by a systole region 1430, a diastolic relaxation region 1432, and a diastolic filling region 1434. The segmentation of the aortic pressure signal into the regions 1430, 1432, and 1434 can be used to segment the data points 1406 into the corresponding systole region 1408, diastolic relaxation region 1412, and diastolic filling region 1410. Segmenting the data 1406 into these regions allows like measurements to be compared so that comparisons are not biased due to misalignment of cardiac phases between a sample measurement and a reference measurement. This can allow the estimation of the heart parameter to be robust to system hysteresis.

Figure 15:
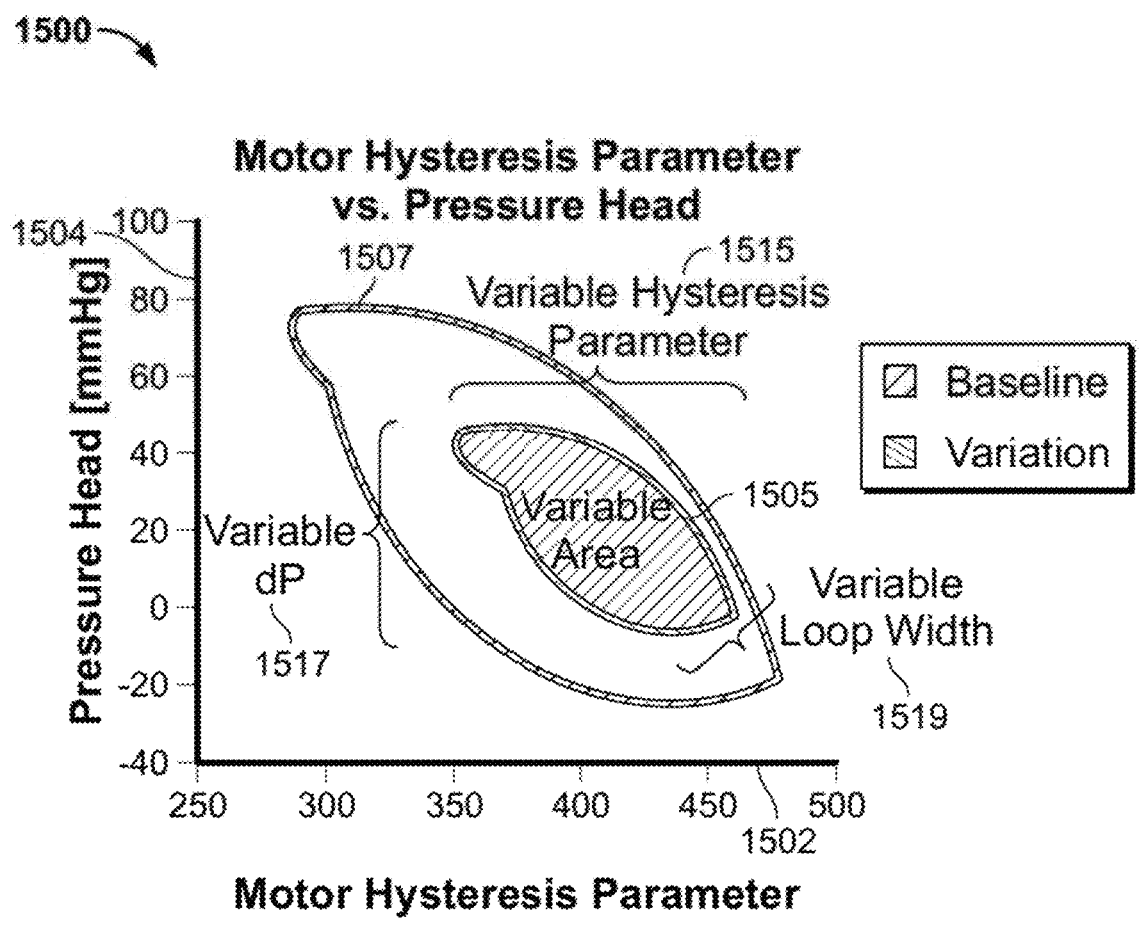
FIG. 15 shows a plot of pressure head as a function of a motor hysteresis parameter.

FIG. 15 shows a scatter plot 1500 of pressure head as a function of motor current. The plot 1500 has an x-axis 1502 showing a motor hysteresis parameter and a y-axis 1504 showing pressure head between the left ventricle and the aorta in units of mmHg. The plot 1500 includes a first hysteresis loop 1507 representing a baseline hysteresis and a second hysteresis loop 1505 representing an example variation of the first hysteresis loop 1507. The second hysteresis loop 1505 includes measurable parameters determined from the plot 1500, including a variable hysteresis parameter 1515, a variable pressure head parameter 1517, and a variable loop width parameter 1519. The variation in the second hysteresis loop 1505 may be caused by changes in the performance of the heart in response to a medical event or in response to external stimuli. The variable hysteresis parameter 1515, variable pressure head parameter 1517, and variable loop width parameter 1519 can describe changes between a first hysteresis loop 1507 and a second hysteresis loop 1505. The variable hysteresis parameter 1515 is measured along the x-axis 1502. The variable pressure head parameter 1517 is measured along the y-axis. The variable loop width parameter 1519 is a measure of the widest portion of the hysteresis loop.

Figure 16:
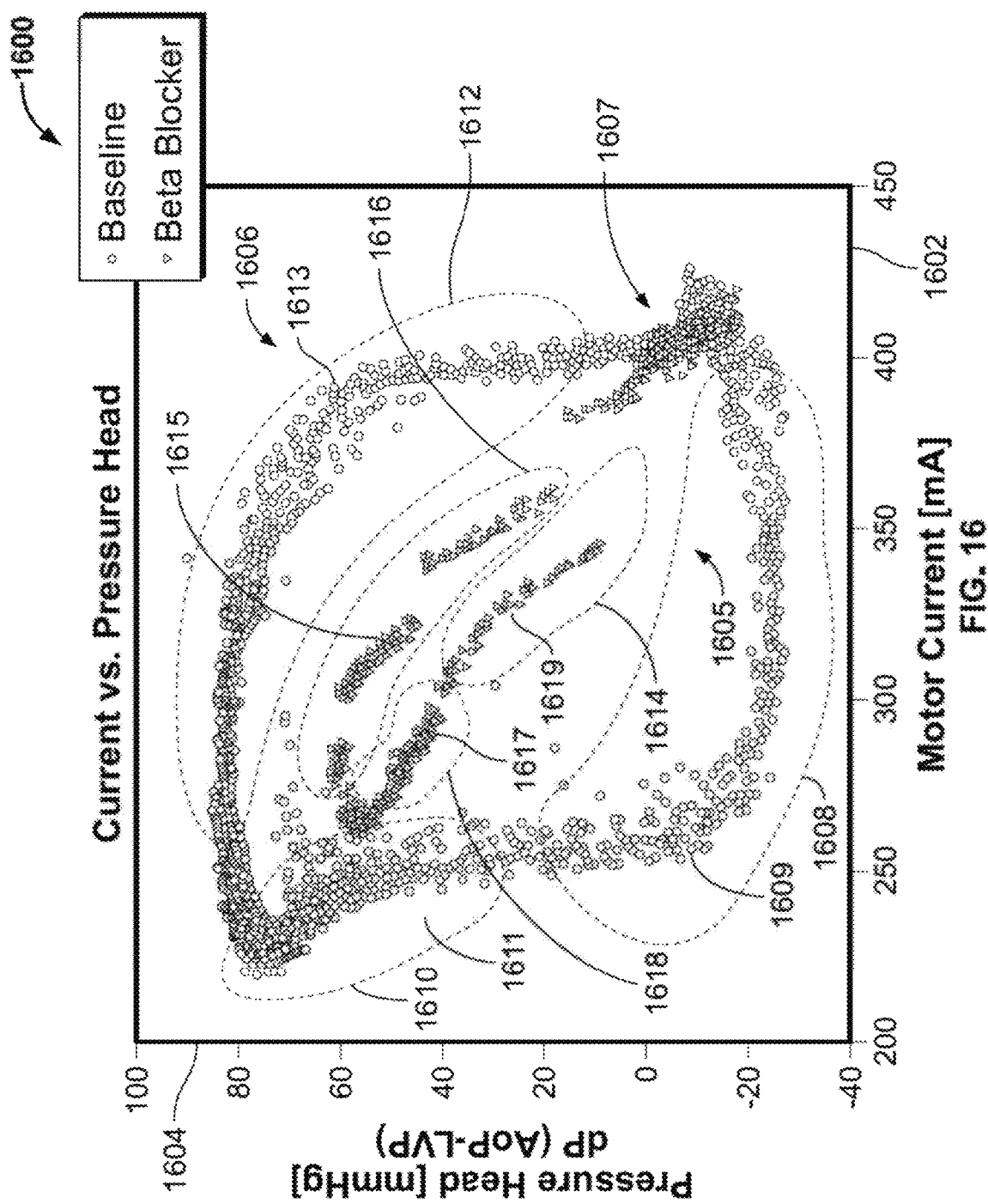
FIG. 16 shows a plot of pressure head as a function of motor current before and after administration of a beta-blocker in a porcine animal model.

FIG. 16 shows a scatter plot 1600 of pressure head as a function of motor current before and after administration of a beta-blocker in a porcine animal model. The plot 1600 has an x-axis 1602 showing current in units of mA and a y-axis 1604 showing pressure head between the left ventricle and the aorta in units of mmHg. The plot 1600 also includes a plurality of data points 1606 representing current-pressure pairs. The data points in plot 1600 were generated in a pig heart while the motor was operating at 30,000 rpm. The data points 1606 roughly form a first hysteresis loop 1607 and a second hysteresis loop 1605. The first hysteresis loop 1607 has three regions, 1612, 1610, and 1608. The first region 1612 includes data points 1613 and is indicative of the diastolic relaxation. The second region 1610 includes data points 1611 and is indicative of the diastolic filling. The third region 1608 includes data points 1609 and is indicative of systole. The first hysteresis loop 1607 was generated during normal function of a heart. The second hysteresis loop 1605 was generated after administration of a beta-blocker. The second hysteresis loop 1605 includes three regions 1616, 1618, and 1614. The first region 1616 includes data points 1615 and is indicative of the diastolic relaxation. The second region 1618 includes data points 1617 and is indicative of the diastolic filling. The third region 1614 includes data points 1619 and is indicative of systole. The shape of the scatter plot 1600 shows that the relationship between current and pressure head between the left ventricle and the aorta varies throughout the cardiac cycle and during normal function (as in hysteresis loop 1607) and after administration of beta-blockers (as in hysteresis loop 1605). The second hysteresis loop 1605 has a lower maximum differential pressure than the first hysteresis loop 1607. Additionally, the shape of the second hysteresis loop 1605 is different than the shape of the first hysteresis loop 1607. In particular, the first region 1616 of the second hysteresis loop 1605 is shifted downward and has a less defined curve than the corresponding first region 1612 of the first hysteresis loop 1607. The third region 1614 of the second hysteresis loop 1605 is also shifted up relative to the corresponding third region 1608 of the first hysteresis loop 1607. Further, the area enclosed by the first hysteresis loop 1607 is larger than the area enclosed by the second hysteresis loop 1605. The administration of beta-blockers results in a change in the contractility of the heart. A trained physician can use the shape of the data points 1606 during a number of heart cycles, and the area of the hysteresis loop that the data points form, to determine morphological changes in the heart as a result of the administration of beta-blockers, or to determine the level of heart failure.

Figure 17:
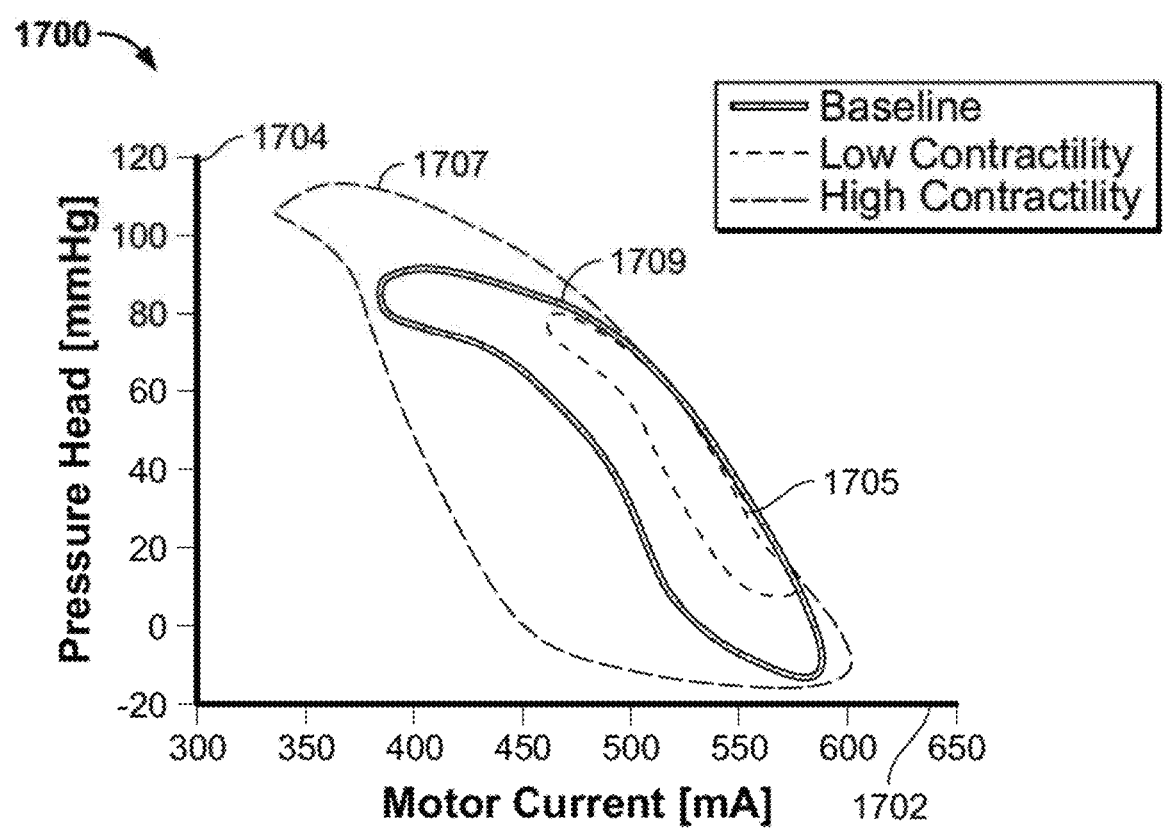
FIG. 17 shows a smoothed curve of a plot of pressure head as a function of motor current.

FIG. 17 shows a smooth curve derived from the scatter plot of FIG. 16. Like the scatter plot 1600 in FIG. 16, the plot 1701 has an x-axis 1702 showing current in units of mA and a y-axis 1704 showing pressure head between the left ventricle and the aorta in units of mmHg. The plot 1701 shows three curves, a baseline curve 1709, a curve showing low contractility 1705, and a curve showing high contractility 1707. The smooth curves of FIG. 17 allow a healthcare professional to visualize the changes in the behavior of the heart, for example after the administration of beta-blockers, as in the low contractility state, and can be used to extract meaningful cardiac parameters and changes in heart health. While FIGS. 16 and 17 include the hysteresis curves shown on an x-axis 1602 and 1702 of motor current in units of mA, the hysteresis curves may be plotted with any motor parameter which varies with time and pulse on the x-axis.

Figure 18A:
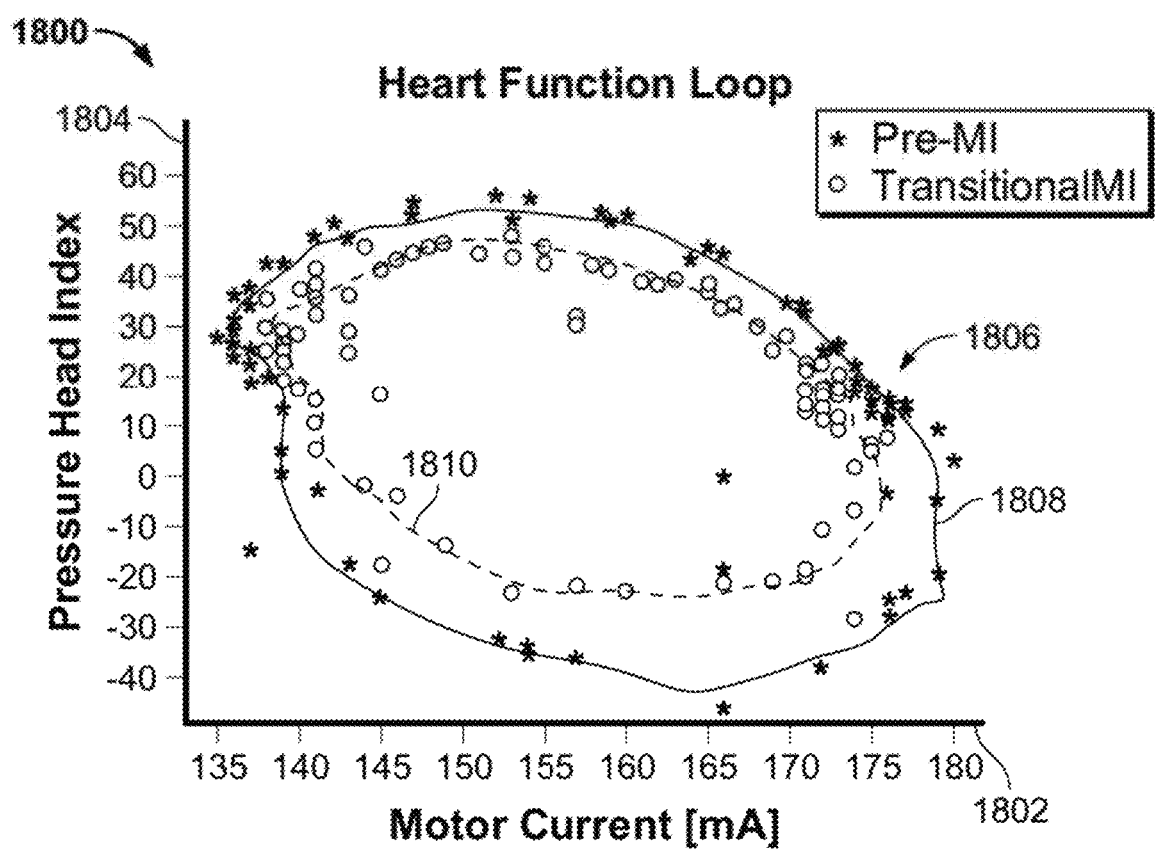
FIG. 18a shows a plot of pressure head as a function of motor current before and during transitioning of a myocardial infarction.

FIG. 18A shows a scatter plot 1800 of pressure head as a function of motor current. The plot 1800 has an x-axis 1802 showing current in units of mA and a y-axis 1804 showing pressure head between the left ventricle and the aorta in units of mmHg. The plot 1800 also includes a plurality of data points 1806 representing current-pressure pairs. The data points 1806 form a first hysteresis loop 1808 and a second hysteresis loop 1810. The shape of the scatter plot 1800 shows that the relationship between current and pressure head between the left ventricle and the aorta varies throughout the cardiac cycle and during normal function (as in hysteresis loop 1808), and during transitioning of a myocardial infarction (as in hysteresis loop 1810). The first hysteresis loop 1808 is indicative of cycles of a heart prior to a myocardial infarction. The second hysteresis loop 1810 is indicative of cycles of a heart during a transitioning myocardial infarction. The area enclosed by the second hysteresis loop 1810 during the myocardial infarction is smaller than the area enclosed by the first hysteresis loop 1808. A trained physician can use the shape of the data points 1806 during a number of heart cycles to determine morphological changes in the heart during or after a myocardial infarction.

Figure 18B:
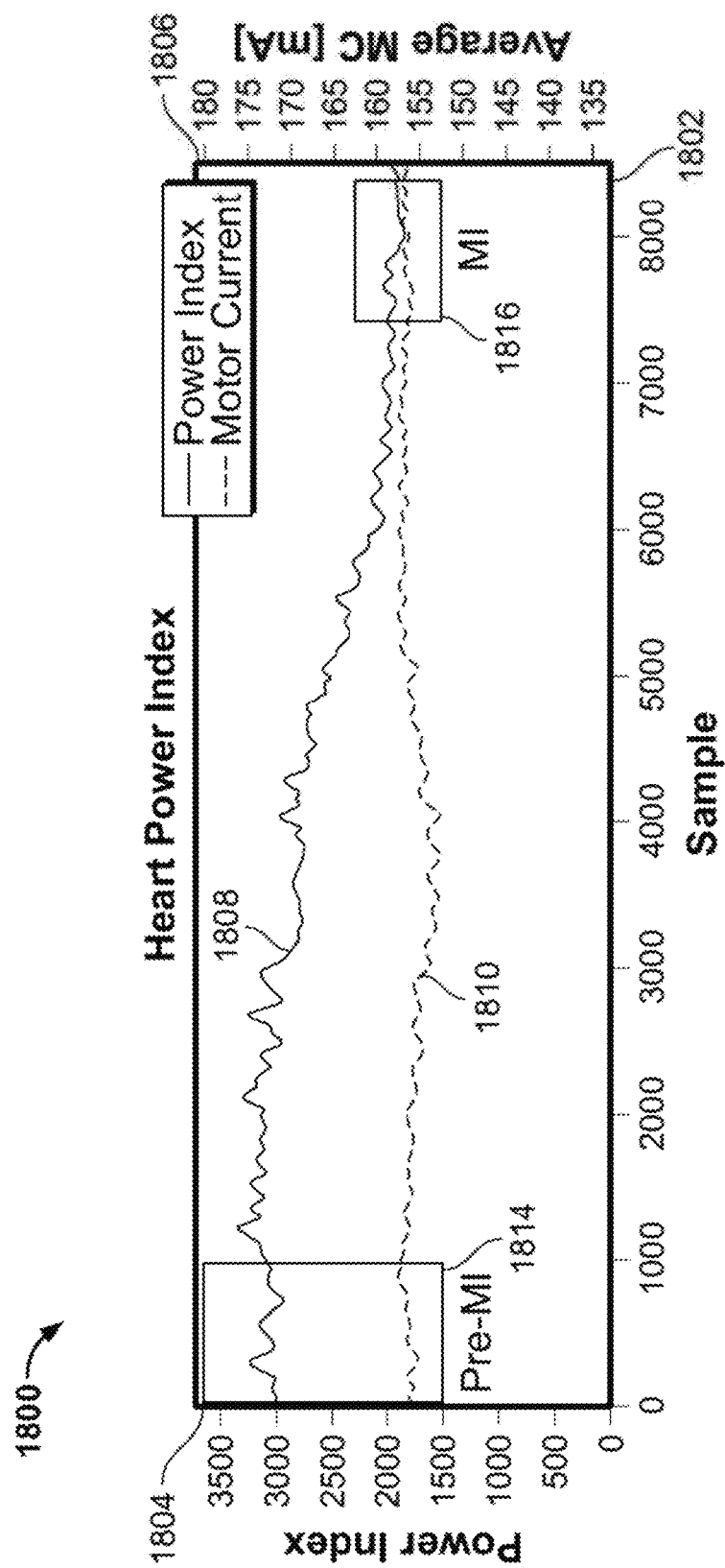
FIG. 18b shows a plot of heart power index and motor current as a function of samples measured over time before and during a myocardial infarction.

FIG. 18B shows a plot 1801 of the heart power index and the motor current over a period of time. The plot 1801 has an x-axis 1803 showing a number of samples taken, a first y-axis 1805 showing the power index of the heart, and a second y-axis 1807 showing an average motor current in units of mA. The plot includes a first tracing 1812 of the heart power index measured over the number of samples and a second tracing 1810 of the motor current over the same samples. Heart power index is a new measure calculated from the hysteresis loop and is intended to give physicians information regarding cardiac performance. In the plot 1801, the motor current 1810 remains largely constant over the measured samples. The heart power index 1808 is shown at low samples during normal cycles of the heart, labeled "pre-MI" 1814. At sample number 500, the heart power index 1812 decreases from about 3000 to about 2000 during a myocardial infarction (labeled "MI"), indicating decreased pumping performance of the heart. The heart power index is an indicator than can be used by trained physicians to monitor the performance of the heart during normal heart cycles and during and after events such as myocardial infarction.

FIG. 19 shows examples of various cardiac parameters over time illustrating the diagnostic capabilities afforded by visualizing the parameters. Each of the plots shows data generated from an animal model showing changes in the area index, contractility, flow load state, and mean aortic pressure over time. Plot I 1900 includes an x-axis 1903 representing time in seconds, a first y-axis 1904 representing the normalized index as a percent and a second y-axis 1905 representing mean pressure in mmHg. Plot I includes tracings of the area index 1910 (indicative of overall heart function), contractility index 1908, flow load state 1912, and mean aortic pressure 1906 during a balloon occlusion of the inferior vena cava.

Plot II 1901 includes an x-axis 1913 representing time in seconds, a first y-axis 1914 representing the normalized index as a percent, and a second y-axis 1915 representing mean pressure in mmHg. Plot II includes tracings of the area index 1920, contractility index 1918, flow load state 1922, and mean aortic pressure 1916 following the use of a beta blocker.

Plot III 1902 includes an x-axis 1923 representing time in seconds, a first y-axis 1924 representing the normalized index as a percent, and a second y-axis 1925 representing mean pressure in mmHg. Plot III includes tracings of the area index 1930, contractility index 1928, flow load state 1932, and mean aortic pressure 1926 following use of an inotrope.

The plots I-III of FIG. 19 illustrate the different responses in the various measurable cardiac parameters in response to various cardiac events. For example, the decrease in heart function illustrated by the decrease in the area index 1910 in plot I is preceded by a decrease in the flow load state index 1912, indicating that there is a problem with the volume of blood pumped by the heart. The decrease in the area index 1920 in plot II coincides with the decrease of the contractility index 1918, indicating that the beta blocker administered to the animal model has affected contractility of the heart. The cardiac parameters displayed in plots I-III can be calculated from hysteresis loops and displayed to illustrate changes in the contractility state, flow load state, and overall cardiac function, and to determine the cause of such changes.

Understanding the trends in the various cardiac parameters for a patient allows a trained medical professional to better address a patient's cardiac needs. The state of a patient's heart can be determined by a health care professional through the changes and trends in the various calculated cardiac parameters.

Figure 20A:
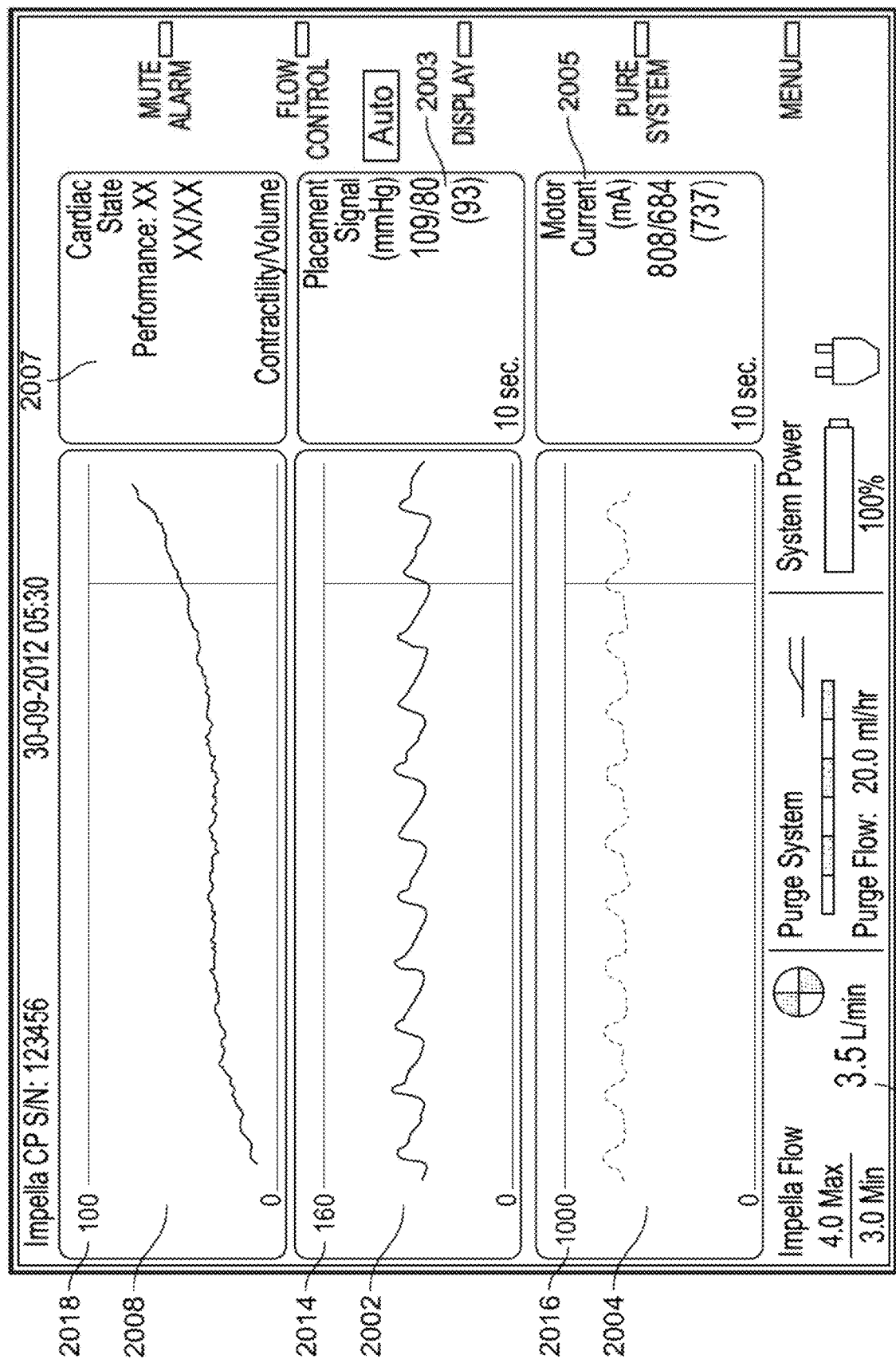
FIG. 20a shows an exemplary user interface for a heart pump controller displaying measurements over time.

FIG. 20A shows an example user interface for a heart pump controller that includes a waveform of a metric of cardiac function over time. The user interface 2000 may be used to control the intravascular heart pump system 100 of FIG. 1, the heart assist device 201 of FIG. 2, the heart pump system 300 of FIG. 3, or any other suitable heart pump. The user interface 2000 includes a pressure signal waveform 2002, a motor current waveform 2004, a cardiac state waveform 2008, and a flow rate 2006. The pressure signal waveform 2002 indicates the pressure measured by the blood pump's pressure sensor (e.g., pressure sensor 312). The pressure signal waveform 2002 can be used by a healthcare professional to properly place an intravascular heart pump (such as intravascular heart pump 100 in FIG. 1) in the heart. The pressure signal waveform 2002 is used to verify the position of the intravascular heart pump by evaluating whether the waveform 2002 is an aortic or ventricular waveform. An aortic waveform indicates that the intravascular heart pump motor is in the aorta. A ventricular waveform indicates that the intravascular heart pump motor has been inserted into the ventricle which is the incorrect location. A scale 2014 for the placement signal waveform is displayed to the left of the waveform. The default scaling is 0-160 mmHg. It can be adjusted in 20 mmHg increments. To the right of the waveform is a display 2003 that labels the waveform, provides the units of measurement, and shows the maximum and minimum values and the average value from the samples received.

The motor current waveform 2004 is a measure of the energy intake of the heart pump's motor. The energy intake varies with the motor speed and the pressure difference between the inlet and outlet areas of the cannula resulting in a variable volume load on the rotor. When used with an intravascular heart pump (such as intravascular heart pump 100 in FIG. 1), the motor current provides information about the catheter position relative to the aortic valve. When the intravascular heart pump is positioned correctly, with the inlet area in the ventricle and the outlet area in the aorta, the motor current is pulsatile because the mass flow rate through the heart pump changes with the cardiac cycle. When the inlet and outlet areas are on the same side of the aortic valve, the motor current will be dampened or flat because the inlet and outlet of the pump are located in the same chamber and there is no variability in differential pressure resulting in a constant mass flow rate, and subsequently constant motor current. A scale 2016 for the motor current waveform is displayed to the left of the waveform. The default scaling is 0-1000 mA. The scaling may be adjustable in 100 mA increments. To the right of the waveform is a display 2005 that labels the waveform, provides the units of measurement, and shows the maximum and minimum values and the average value from the samples received. Though the pressure sensor and motor current sensor may not be required for positioning of surgically implanted pumps, such as heart assist device 201 of FIG. 2, the sensors can be used in such devices to determine additional characteristics of native heart function to monitor therapy.

The cardiac state waveform 2008 is a display of the recorded cardiac state over a period of time. The cardiac state may be displayed as a ratio of the contractility of the heart divided by the volume of blood pumped. The cardiac state may be calculated at discrete time points or continuously and displayed in the cardiac state waveform 2008 as a trend in order to provide a physician with an indicator of the current performance of the heart relative to the performance at other points in time in the patient's treatment. A scale 2018 for the cardiac state waveform 2008 is displayed to the left of the cardiac state trend line. The default scaling is from 1-100 (unitless). The scaling may be adjusted to best show the cardiac state trend. To the right of the cardiac state waveform 2008 is a display 2007 that labels the trend line, provides additional information about the cardiac performance at the current time, and shows the current values of contractility and volume received from the pump. The display of this information as a trend line allows a physician to view the historical cardiac state of a patient and to make decisions based on the trend of the cardiac state. For example, a physician may observe from the cardiac state trend line a decline or an increase in the cardiac state over time and determine to alter or continue treatment based on this observation.

The flow rate 2006 can be a target blood flow rate set by the user or an estimated actual flow rate. In some modes of the controller, the controller will automatically adjust the motor speed in response to changes in afterload to maintain a target flow rate. In some implementations, if flow calculation is not possible, the controller will allow a user to set a fixed motor speed as indicated by speed indicator 2008.

Figure 20B:
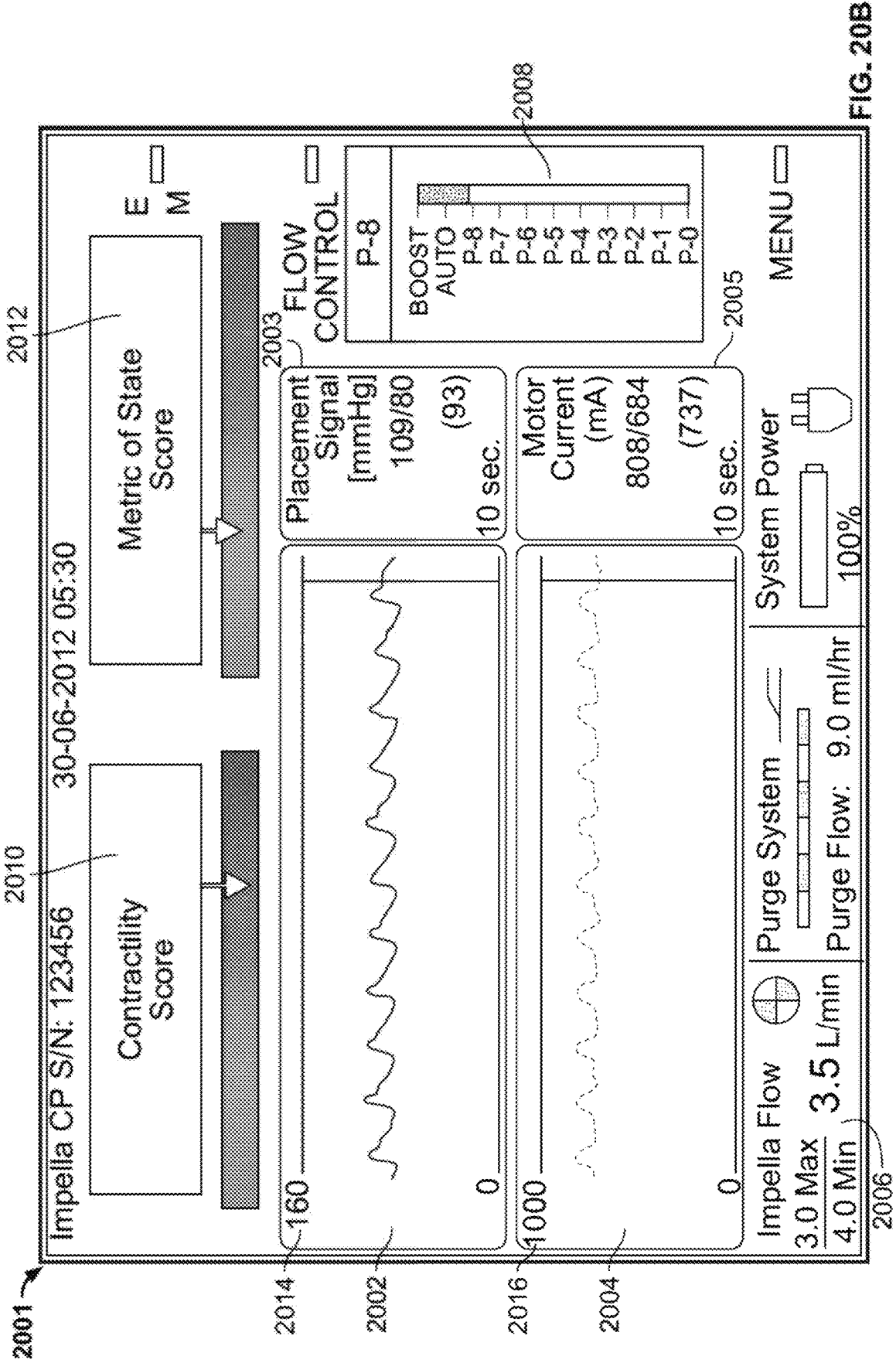
FIG. 20b shows an exemplary user interface for a heart pump controller according to certain implementations.

FIG. 20B shows an example user interface 2001 for a heart pump controller according to certain implementations. The user interface 2001 may be used to control the intravascular heart pump system 100 of FIG. 1, the heart assist device 201 of FIG. 2, the heart pump system 300 of FIG. 3, or any other suitable heart pump. The user interface 2001 includes a pressure signal waveform 2022, a motor current waveform 2024, a flow rate 2026, a speed indicator 2028, a contractility score 2030 and a metric of state score 2032. The pressure signal waveform 2022 indicates the pressure measured by the blood pump's pressure sensor (e.g., pressure sensor 312). The pressure signal waveform 2022 can be used by a healthcare professional to properly place an intravascular heart pump (such as intravascular heart pump 100 in FIG. 1) in the heart. The pressure signal waveform 2022 is used to verify the position of the intravascular heart pump by evaluating whether the waveform 2022 is an aortic or ventricular waveform. An aortic waveform indicates that the intravascular heart pump motor is in the aorta. A ventricular waveform indicates that the intravascular heart pump motor has been inserted into the ventricle, which is the incorrect location. A scale 2034 for the placement signal waveform is displayed to the left of the waveform. The default scaling is 0-160 mmHg. It can be adjusted in 20 mmHg increments. To the right of the waveform is a display 2033 that labels the waveform, provides the units of measurement, and shows the maximum and minimum values and the average value from the samples received.

The motor current waveform 2024 is a measure of the energy intake of the heart pump's motor. The energy intake varies with the motor speed and the pressure difference between the inlet and outlet areas of the cannula resulting in a variable volume load on the rotor. When used with an intravascular heart pump (such as intravascular heart pump 100 in FIG. 1), the motor current provides information about the catheter position relative to the aortic valve. When the intravascular heart pump is positioned correctly, with the inlet area in the ventricle and the outlet area in the aorta, the motor current is pulsatile because the mass flow rate through the heart pump changes with the cardiac cycle. When the inlet and outlet areas are on the same side of the aortic valve, the motor current will be dampened or flat because the inlet and outlet of the pump are located in the same chamber and there is no variability in differential pressure resulting in a constant mass flow rate, and subsequently constant motor current. A scale 2036 for the motor current waveform is displayed to the left of the waveform. The default scaling is 0-1000 mA. The scaling may be adjustable in 100 mA increments. To the right of the waveform is a display 2025 that labels the waveform, provides the units of measurement, and shows the maximum and minimum values and the average value from the samples received. Though the pressure sensor and motor current sensor may not be required for positioning of surgically implanted pumps, such as heart assist device 201 of FIG. 2, the sensors can be used in such devices to determine additional characteristics of native heart function to monitor therapy.

The flow rate 2026 can be a target flow rate set by the user or an estimated actual flow rate. In some modes of the controller, the controller will automatically adjust the motor speed in response to changes in afterload to maintain a target flow rate. In some implementations, if flow calculation is not possible, the controller will allow a user to set a fixed motor speed as indicated by speed indicator 2028.

The contractility score 2030 provides an indication of cardiac function. More specifically, the contractility score represents the inherent strength and vigor of the heart's contraction during systole. The stroke volume of the heart will be greater if the contractility of the heart is greater. For example, medium contractility may occur when the stroke volume of the heart is about 65 mL. High contractility may occur when the stroke volume of the heart is over 100 mL. Low contractility may occur when the stroke volume of the heart is less than 30 mL. The contractility score may be expressed numerically and/or graphically. The contractility score may be non-dimensional. Changes in contractility can be determined from the variation in slope of pressure during cardiac contraction (dP/dt). The metric of state score 2032 also provides an indication of cardiac function. The metric of state score may be an indication of volume load, the pressure of a cardiac pressure, or another metric of cardiac function.

The position, depictions of the metrics on the controller, and the identification and number of metrics and recommendations in FIGS. 20A and 20B are meant to be illustrative. The number of metrics and indicators, position of same metrics and indicators on the console and the metrics displayed may be varied from those shown here. The metrics displayed to a user can be contractility, stroke volume, ejection fraction, chamber pressure, stroke work, cardiac output, cardiac power output, LVEDP, preload state, afterload state, flow load state, variable volume load state, cardiac cycle volume load state, cardiac cycle flow state, heart rate, and/or heart recovery as defined by any or all of the prior heart related parameters, the trends over time, and specific thresholds, or any other suitable metric derived from a hysteresis parameter associated with a cardiac assist device placed in or partially in an organ of a patient.

Figure 21:
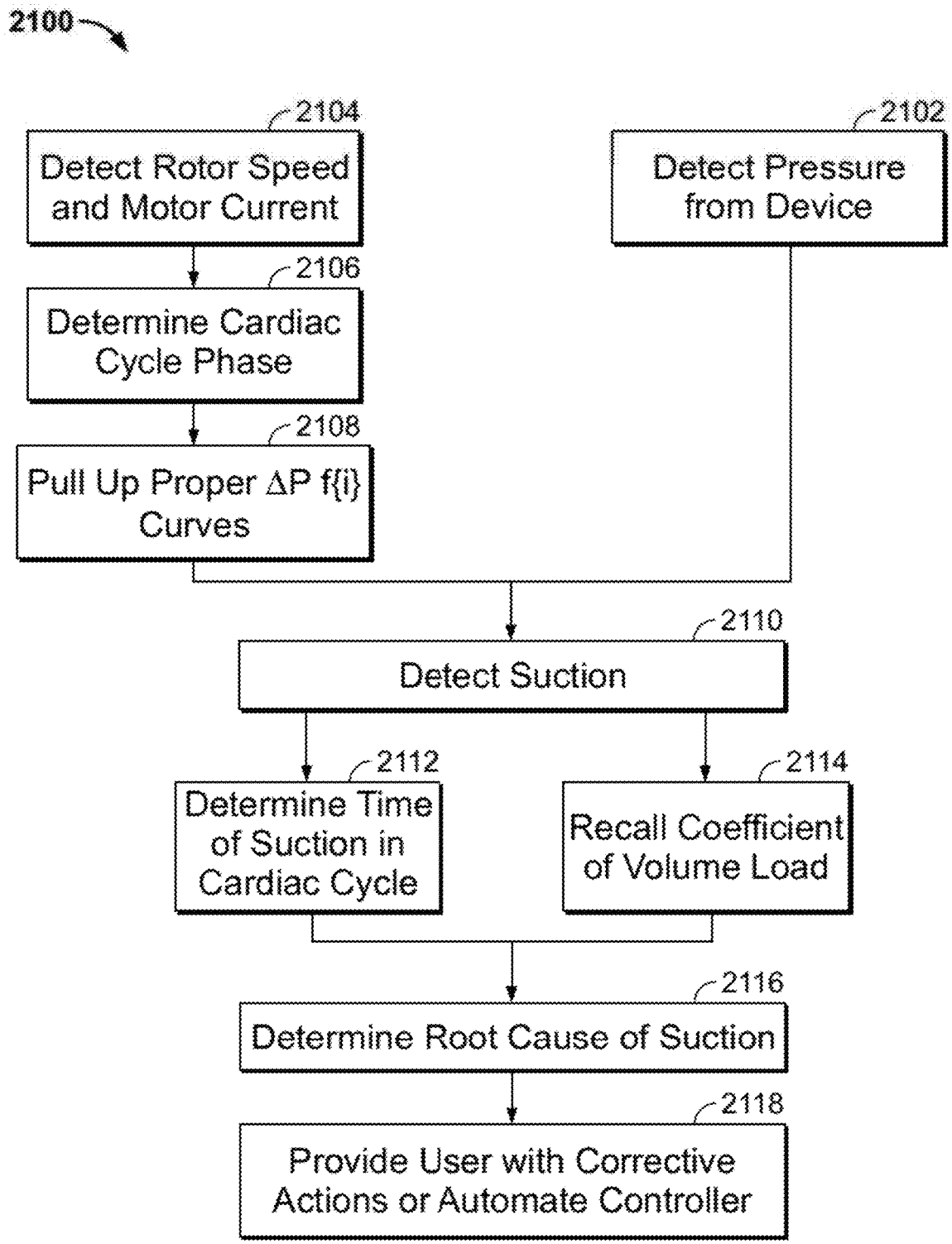
FIG. 21 shows a process for detecting suction in an intravascular heart pump and determining the cause of the suction according to certain implementations.

FIG. 21 shows a process for detecting suction in an intravascular heart pump and determining the cause of the suction. Suction occurs when an inlet of the cardiac assist device is occluded (e.g., by a valve leaflet or other anatomical structure) or when blood volume or preload to the ventricle is reduced and less than the output of the selected pump speed. Preventing suction can allow intravascular cardiac assist devices to operate safely at higher flow rates. Conventional suction detection technology is insufficiently sensitive to detect minor suction, to detect when the suction is occurring during the cardiac cycle, and to detect an unfavorable cardiac cycle flow state which could lead to suction events. The process 2100 may detect suction sooner than conventional methods and can provide the user information on how to prevent continued or worsening suction.

In step 2102, pressure is detected from the cardiac assist device. In step 2104, rotor speed and motor current are detected. In step 2106, the cardiac cycle phase is determined. The phase estimation can act as a filter for the pressure and current signals because it can allow pressure and current signals to be compared to pressure and current signals that occurred during corresponding stages of the cardiac cycle. The phase estimation may be based on the pressure information received in step 2102 and may involve locating fiducial points in the pressure information indicative of the heart phase. In some implementations, the dicrotic notch in the pressure signal is detected to indicate the beginning of diastolic filling. The dicrotic notch is a small downward deflection in the arterial pulse or pressure contour immediately following the closure of the semilunar valves. This dicrotic notch can be used as a marker for the end of systole and hence approximately the beginning of diastole.

In some implementations, the phase estimation is entirely or partially based on ECG data. Such ECG data may be timed with the pressure tracings. The characteristic in the ECG used to estimate the heart phase may be the beginning of the QRS complex and the end of the T-wave. If there is noise in the ECG signal, it may be more reliable to detect the peak of the QRS complex (e.g., the R-wave) and the peak of the T-wave. In phase estimation methods using either pressure signals or ECG signals, an offset from the detected feature may be used to more accurately identify filling phases since actual filling occurs slightly before or after these identified landmarks. A combination of both pressure signal-based and ECG-based methods can allow more reliable identification. The weighting between the two methods can be optimized using datasets having known filling time parameters, known left ventricular pressures, and high signal to noise ratios.

In step 2108, predetermined pressure curves are referenced to determine a heart parameter indicative of suction. In some implementations, the table may be based on predetermined pressure-current curves. Heart parameters can be determined by mapping the measured current and pressure to heart parameters. The reference table may be a look-up table that accepts as its inputs: pressure, motor current, and heart phase. The heart phase information may be binary (e.g., diastole or systole) or more fine-grained (e.g., systole, diastolic relaxation, and diastolic filling). In step 2110, a suction event is detected. The suction event can be detected by determining a deviation from the normal predetermined pressure-current curves. The deviation may indicate a mass flow rate that is atypically low for the corresponding aortic pressure and heart phase. In some implementations, the suction event is detected by a change in a hysteresis loop of a motor parameter and a pressure head. An early indication of a suction event is the collapse of the hysteresis loop. The loop collapses as the volume load decreases, indicating that a suction event has begun.

In step 2112, the time in the cardiac cycle during which the suction events occur is determined. For example, it may be determined whether suction events occur during systole or diastole. The method for stopping the suction event or events can depend on whether the suction event occurs during systole or diastole. In step 2114, the coefficient of volume load is determined. Based on the coefficient of volume load and the determination of when the suction occurs in the cardiac cycle, the root cause of suction is determined. For example, the root cause may be suction against a valve leaflet. In step 2118, a user is provided with corrective actions for addressing the suction event. For example, the user may be prompted to reposition the cardiac assist device within the heart. In some implementations, when onset of a suction event is detected an early detection warning of possible suction event is activated.

In some implementations, conditions leading to a suction event can be detected, for example, by detecting a reduction in the volume load experienced by the pump. The chamber blood volume of the pump may be detected using the hysteresis in the measurement of the motor parameter and pressure measurement at the pressure sensor and compared to a set level of pump support to determine if the chamber blood volume is critically reduced. Critical reduction of chamber blood volume can be present when a suction event is occurring, and detection of a reduction can provide an early warning or a prompt to action to prevent a suction event from continuing. In some implementations, the action is automated. In some implementations, the action is recommended. In some implementations, the automated or recommended action is to reduce support level provided by the pump (e.g., decrease rotor speed) to match the volume status.

Example Embodiment 1

An IMPELLA® percutaneous heart pump (Abiomed, Inc., Danvers, Mass.) was implanted in a mock circulatory loop (MCL) consisting of ventricle and aorta with pressures measured throughout. The IMPELLA® operated at various performance levels and MCL fluid dynamic profiles while motor current was recorded. An LVP prediction algorithm was generated using pump characterization. Performance was validated in an anesthetized pig with an implanted IMPELLA®. Ischemia-like or hemorrhagic shock-like events were induced by balloon-occluding the left anterior descending coronary artery or the inferior vena cava respectively. The IMPELLA® pump's motor current and pressure signals in the pulmonary artery, left ventricle, and aorta were recorded simultaneously.

At minimal ventricular support, ischemia and shock was followed within 4 minutes by profound changes. Instability and shock were reflected by changes in the motor current waveform. The left ventricular pressure (LVP) was predicted during hemorrhagic shock with characterization from both the MCL (RMS error ~0.3 mmHg) and the pig (RMS error ~0.9 mmHg). In contrast, at maximal ventricular support, there was no hemodynamic compromise and the motor current remained intact after >20 minutes of occlusion.

The results indicate coupling between heart and device function. Without adequate support, heart performance reduced and led to hemodynamic collapse, which was tracked by the LVP algorithm. Success of the algorithm is due to the use of the MCL and the porcine model during development. The MCL defined the bounds of pump performance, while the animal delineated biological variability and pathology. This unified approach can be an effective means of defining performance of any device: using MCL for characterization and animals as validation.

The foregoing is merely illustrative of the principles of the disclosure, and the apparatuses can be practiced by other than the described embodiments, which are presented for purposes of illustration and not of limitation. It is to be understood that the apparatuses disclosed herein, while shown for use in percutaneous insertion of heart pumps, may be applied to apparatuses in other applications.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

In general, embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices.

Examples of changes, substitutions, and alterations are ascertainable by one skilled in the art and could be made without departing from the scope of the information disclosed herein. All references cited herein are incorporated by reference in their entirety and made part of this application.

We claim:

1. A heart pump system comprising:
a motor;
a rotor operatively coupled to the motor;
a pump housing at least partially surrounding the rotor so that actuating the motor drives the rotor and pumps blood through the pump housing;
a sensor configured to detect an aortic pressure over time; and
a controller configured to:
    detect over time a motor parameter associated with the motor,
    receive, as an input from the sensor, the aortic pressure over time,
    determine a mathematical relationship between the aortic pressure and the motor parameter,
    determine a cardiac cycle phase from the mathematical relationship between the aortic pressure and the motor parameter,
    obtain a hysteresis curve based on the mathematical relationship between the aortic pressure and the motor parameter, and
    select a sample time on the hysteresis curve corresponding to the cardiac cycle phase.

2. The heart pump system of claim 1, wherein the motor parameter is at least one of: current delivered to the motor, power delivered to the motor, and motor speed.

3. The heart pump system of claim 1, wherein the controller is configured to determine at least one cardiovascular metric by extracting an inflection point, a local slope change, or a curvature change from the mathematical relationship between the aortic pressure and the motor parameter.

4. The heart pump system of claim 3, wherein the at least one cardiovascular metric is at least one of contractility, stroke volume, ejection fraction, chamber pressure, stroke work, cardiac output, cardiac power output, left ventricular end diastolic pressure (LVEDP), preload state, afterload state, heart rate, heart recovery, flow load state, variable volume load state, cardiac cycle volume load state, and cardiac cycle flow state.

5. The heart pump system of claim 4, wherein the at least one cardiovascular metric is the LVEDP.

6. The heart pump system of claim 1, comprising a catheter having a distal region, wherein the distal region is operationally coupled to the motor.

7. The heart pump system of claim 1, wherein the controller is configured to determine the mathematical relationship between the aortic pressure and the motor parameter using a polynomial best fit algorithm.

8. The heart pump system of claim 7, wherein the motor parameter includes a current delivered to the motor, and wherein determining the mathematical relationship includes fitting an equation to at least a portion of data representing the current and a pressure head calculated from the current and the aortic pressure.

9. The heart pump system of claim 8, where the controller is configured to:
determine an LVEDP point using the equation fitted to at least the portion of data representing the current and the pressure head; and
access a look-up table to determine an actual LVEDP value from the LVEDP point in the pressure head.

10. The heart pump system of claim 9, wherein determining an LVEDP point includes identifying a change in slope, a change in curvature or an inflection point in the equation fit to at least the portion of data representing the current and the pressure head.

11. The heart pump system of claim 1, wherein the controller is configured to detect the motor parameter and the sensor is configured to detect the aortic pressure over a portion of a cardiac cycle.

12. The heart pump system of claim 1, wherein the controller is configured to detect the motor parameter and the sensor is configured to detect the aortic pressure over one or more cardiac cycles.

13. The heart pump system of claim 1, wherein the motor is configured to maintain a substantially constant speed of the rotor during actuation of the rotor.

14. The heart pump system of claim 1, wherein the controller is further configured to store the at least one cardiovascular metric in a memory with a previously determined at least one cardiovascular metric.

15. The heart pump system of claim 1, wherein the controller is configured to adjust, based on the mathematical relationship, operation of the heart pump system to change a speed of the rotor.

16. The heart pump system of claim 1, wherein the controller is configured to:
   display an indicator of the mathematical relationship;
   receive a request for adjustment of operation of the heart pump system; and
   adjust, based on the request, operation of the motor to drive the heart pump system.

17. The heart pump system of claim 16, wherein the motor is an integrated motor sized and configured for insertion into a patient's vasculature by catheter.

18. The heart pump system of claim 1, wherein determining the cardiac cycle phase further comprises:
   detecting that the cardiac cycle phase is in diastolic relaxation when the sample time corresponds to a segment of the hysteresis curve corresponding to an increasing pressure head; or
   detecting that the cardiac cycle phase is in diastolic filling when the sample time corresponds to a segment of the hysteresis curve corresponding to a decreasing pressure head following diastolic relaxation to a point distinguished by a rapid change in slope or curvature, or identification of an inflection point; or
   detecting that the cardiac cycle phase is in systole when the sample time corresponds to a segment of the hysteresis curve having a decreasing pressure head from an inflection point to a minimum pressure head.

19. The heart pump system of claim 1, further comprising a pump inlet, and wherein the controller is further configured to determine, based on the hysteresis curve, a pump inlet occlusion.

* * * * *